(12) United States Patent
Dalton et al.

(10) Patent No.: US 9,730,908 B2
(45) Date of Patent: *Aug. 15, 2017

(54) SARMS AND METHOD OF USE THEREOF

(71) Applicant: University of Tennessee Research Foundation, Knoxville, TN (US)

(72) Inventors: James T. Dalton, Ann Arbor, MI (US); Duane D. Miller, Collierville, TN (US); Thamarai Ponnusamy, Memphis, TN (US); Ramesh Narayanan, Cordove, TN (US)

(73) Assignee: UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/963,054

(22) Filed: Dec. 8, 2015

(65) Prior Publication Data

US 2016/0158185 A1 Jun. 9, 2016

Related U.S. Application Data

(60) Continuation-in-part of application No. 14/168,993, filed on Jan. 30, 2014, now Pat. No. 9,278,914, which is a continuation of application No. 13/627,900, filed on Sep. 26, 2012, now Pat. No. 8,669,286, which is a continuation of application No. 12/730,094, filed on Mar. 23, 2010, now Pat. No. 8,309,603, said application No. 14/168,993 is a continuation-in-part of application No. 13/868,768, filed on Apr. 23, 2013, now Pat. No. 8,846,756, which is a continuation of application No. 13/302,988, filed on Nov. 22, 2011, now Pat. No. 8,426,465, which is a division of application No. 11/892,595, filed on Aug. 24, 2007, now Pat. No. 8,080,682.

(60) Provisional application No. 60/839,665, filed on Aug. 24, 2006, provisional application No. 60/907,749, filed on Apr. 16, 2007.

(51) Int. Cl.
| | | |
|---|---|---|
| *A61K 31/277* | (2006.01) | |
| *C07C 255/60* | (2006.01) | |
| *A23K 20/111* | (2016.01) | |
| *A23K 50/10* | (2016.01) | |
| *A23K 50/30* | (2016.01) | |
| *A23K 50/75* | (2016.01) | |
| *A23K 50/80* | (2016.01) | |

(52) U.S. Cl.
CPC .......... *A61K 31/277* (2013.01); *A23K 20/111* (2016.05); *A23K 50/10* (2016.05); *A23K 50/30* (2016.05); *A23K 50/75* (2016.05); *A23K 50/80* (2016.05); *C07C 255/60* (2013.01)

(58) Field of Classification Search
CPC ...... A61K 31/277; A23K 50/75; A23K 50/80; A23K 50/30; A23K 50/10; A23K 20/111; C07C 255/60
See application file for complete search history.

(56) References Cited

U.S. PATENT DOCUMENTS

| | | | |
|---|---|---|---|
| 3,239,345 A | 3/1966 | Hodge | |
| 3,875,229 A | 4/1975 | Gold | |
| 4,036,979 A | 7/1977 | Asato | |
| 4,139,638 A | 2/1979 | Neri et al. | |
| 4,191,775 A | 3/1980 | Glen | |
| 4,239,776 A | 12/1980 | Glen et al. | |
| 4,282,218 A | 8/1981 | Glen et al. | |
| 4,386,080 A | 5/1983 | Crossley et al. | |
| 4,411,890 A | 10/1983 | Momany et al. | |
| 4,465,507 A | 8/1984 | Konno et al. | |
| 4,636,505 A | 1/1987 | Tucker | |
| 4,880,839 A | 11/1989 | Tucker | |
| 5,162,504 A | 11/1992 | Horoszewicz | |
| 5,179,080 A | 1/1993 | Rothkopf et al. | |
| 5,609,849 A | 3/1997 | Kung | |
| 5,612,359 A | 3/1997 | Murugesan et al. | |
| 5,656,651 A | 8/1997 | Sovak et al. | |
| 6,019,957 A | 2/2000 | Miller et al. | |
| 6,043,265 A | 3/2000 | Murugesan et al. | |
| 6,071,957 A | 6/2000 | Miller et al. | |
| 6,160,011 A | 12/2000 | Miller et al. | |
| 6,482,861 B2 | 11/2002 | Miller et al. | |
| 6,492,554 B2 | 12/2002 | Dalton et al. | |
| 6,548,529 B1 | 4/2003 | Robl et al. | |
| 6,569,896 B2 | 5/2003 | Dalton et al. | |
| 6,777,427 B2 | 8/2004 | Miyakawa et al. | |
| 6,838,484 B2 | 1/2005 | Steiner et al. | |

(Continued)

FOREIGN PATENT DOCUMENTS

| | | |
|---|---|---|
| CA | 1305665 | 7/1992 |
| CA | 2149240 | 5/1994 |

(Continued)

OTHER PUBLICATIONS

West, Anthony R., Solid State Chemistry and its Applications, Wiley, New York, 1988, pp. 358 & 365.*

Abuchowski et al. "Immunosuppressive properties and circulating life of Achromobacter glutaminase-asparaginase covalently attached to polyethylene glycol in man" Cancer Treat Rep. 65(11-12):1077-81. Nov.-Dec. 1981.

Baird et al.; "Hormonal Contraception—Drug Therapy", The New England Journal of Medicine , May 27, 1993, pp. 1543-1549.

Belani, C. P. et al, "Development of docetaxel inadvanced non-small-cell lung cancer." Lung Cancer, 46, pp. S3-S11, 2004.

Berger et al., "Concepts and limitations in the application of radiolabeled antiandrogens, estrogens, or androgens as isotropic scanning agents for the prostate", Invest. Urol, (1975), 1391, 10-16.

(Continued)

*Primary Examiner* — Yong Chu
(74) *Attorney, Agent, or Firm* — Mark S. Cohen; Pearl Cohen Zedek Latzer Baratz LLP

(57) ABSTRACT

This invention is directed to substituted acylanilide compounds and uses thereof in treating a variety of diseases or conditions in a subject, including, inter alia, a muscle wasting disease and/or disorder such as Duchenne muscular dystrophy or Becker muscular dystrophy.

15 Claims, 35 Drawing Sheets

(56) References Cited

U.S. PATENT DOCUMENTS

| | | |
|---|---|---|
| 6,960,474 B2 | 11/2005 | Salvati et al. |
| 6,998,500 B2 | 2/2006 | Dalton et al. |
| 7,026,500 B2 | 4/2006 | Dalton et al. |
| 7,547,728 B2 | 6/2009 | Steiner et al. |
| 7,622,503 B2 | 11/2009 | Dalton et al. |
| 7,645,898 B2 | 1/2010 | Dalton et al. |
| 7,705,182 B2 | 4/2010 | Dalton et al. |
| 7,772,433 B2 * | 8/2010 | Dalton .................. A61K 38/35 558/414 |
| 7,803,970 B2 | 9/2010 | Dalton et al. |
| 7,825,229 B2 | 11/2010 | Itzhak et al. |
| 7,855,229 B2 | 12/2010 | Dalton et al. |
| 7,919,647 B2 | 4/2011 | Dalton et al. |
| 7,968,603 B2 | 6/2011 | Dalton et al. |
| 7,977,386 B2 | 7/2011 | Dalton et al. |
| 8,008,348 B2 | 8/2011 | Steinder et al. |
| 8,080,682 B2 * | 12/2011 | Dalton .................. C07C 255/60 558/414 |
| 8,563,606 B2 | 10/2013 | Dalton et al. |
| 8,846,756 B2 * | 9/2014 | Dalton .................. C07C 255/60 514/522 |
| 8,853,266 B2 | 10/2014 | Dalton et al. |
| 9,150,501 B2 | 10/2015 | Dalton et al. |
| 2001/0012839 A1 | 8/2001 | Miller et al. |
| 2002/0099036 A1 | 7/2002 | Dalton et al. |
| 2002/0099096 A1 | 7/2002 | Dalton et al. |
| 2002/0173445 A1 | 11/2002 | Salvati et al. |
| 2002/0173495 A1 | 11/2002 | Dalton et al. |
| 2003/0162761 A1 | 8/2003 | Steiner et al. |
| 2003/0225040 A1 | 12/2003 | Dalton et al. |
| 2003/0229099 A1 | 12/2003 | Zhu et al. |
| 2003/0232792 A1 | 12/2003 | Dalton et al. |
| 2003/0232882 A1 | 12/2003 | Miller et al. |
| 2004/0014975 A1 | 1/2004 | Dalton et al. |
| 2004/0029913 A1 | 2/2004 | Dalton et al. |
| 2004/0087557 A1 | 5/2004 | Steiner et al. |
| 2004/0087810 A1 | 5/2004 | Dalton et al. |
| 2004/0214790 A1 | 10/2004 | Borgens et al. |
| 2005/0038110 A1 | 2/2005 | Steiner et al. |
| 2006/0035965 A1 | 2/2006 | Dalton et al. |
| 2006/0111441 A1 | 5/2006 | Dalton et al. |
| 2006/0165744 A1 | 7/2006 | Jamil et al. |
| 2006/0183931 A1 | 8/2006 | Dalton et al. |
| 2006/0229362 A1 | 10/2006 | Dalton et al. |
| 2007/0066568 A1 | 3/2007 | Dalton et al. |
| 2007/0281906 A1 | 12/2007 | Dalton et al. |
| 2008/0076828 A1 | 3/2008 | Dalton et al. |
| 2008/0076829 A1 | 3/2008 | Dalton et al. |
| 2009/0270512 A1 | 10/2009 | Koh et al. |
| 2010/0249228 A1 | 9/2010 | Dalton et al. |
| 2013/0034562 A1 | 2/2013 | Dalton et al. |
| 2014/0011774 A1 | 1/2014 | Dalton et al. |
| 2014/0018433 A1 | 1/2014 | Dalton et al. |
| 2014/0080905 A1 | 3/2014 | Dalton et al. |
| 2014/0350102 A1 | 11/2014 | Dalton et al. |

FOREIGN PATENT DOCUMENTS

| | | |
|---|---|---|
| CA | 2247946 | 10/1997 |
| CA | 2281570 | 9/1998 |
| CA | 2313089 | 6/1999 |
| CA | 2344316 | 3/2000 |
| CA | 2413417 | 1/2002 |
| CA | 2420279 | 2/2002 |
| CA | 2459340 | 3/2003 |
| CA | 2469340 | 6/2003 |
| CA | 2536518 | 2/2005 |
| CA | 2543827 | 12/2005 |
| CN | 101299920 A | 11/2008 |
| CN | 1016778035 A | 3/2012 |
| EA | 200601110 A1 | 6/2006 |
| EP | 0040932 | 12/1981 |
| EP | 0100172 | 2/1984 |
| EP | 0002892 | 2/1985 |
| EP | 0253503 | 1/1988 |
| EP | 1221439 | 7/2002 |
| GB | 1360001 | 3/1970 |
| JP | 52-128329 | 10/1977 |
| JP | 54-63047 | 12/1980 |
| JP | 2004329110 A | 11/2004 |
| WO | WO 89/07110 | 8/1989 |
| WO | WO 89/07111 | 8/1989 |
| WO | WO 93/04081 | 3/1993 |
| WO | WO 95/19770 | 7/1995 |
| WO | WO 98/05962 | 2/1998 |
| WO | WO 98/53826 | 12/1998 |
| WO | WO 98/55153 | 12/1998 |
| WO | WO 01/27086 | 4/2001 |
| WO | WO 01/27622 | 4/2001 |
| WO | WO 01/28990 | 4/2001 |
| WO | WO 01/34563 | 5/2001 |
| WO | WO 01/68603 | 9/2001 |
| WO | WO 02/00617 | 1/2002 |
| WO | WO 02/16310 | 2/2002 |
| WO | WO 02/22585 | 3/2002 |
| WO | WO 03/039534 A1 | 5/2003 |
| WO | WO 03/049675 | 6/2003 |
| WO | WO 03/065992 A2 | 8/2003 |
| WO | WO 03/074449 A2 | 9/2003 |
| WO | WO 03/074471 A1 | 9/2003 |
| WO | WO 03/077919 | 9/2003 |
| WO | WO 2004/034978 | 4/2004 |
| WO | WO 2004/035736 | 4/2004 |
| WO | WO 2004/035739 | 4/2004 |
| WO | WO 2004/064747 | 8/2004 |
| WO | WO 2005/000794 | 1/2005 |
| WO | WO 2005/005606 | 1/2005 |
| WO | WO 2005/036980 | 4/2005 |
| WO | WO 2005/037201 A2 | 4/2005 |
| WO | WO 2005/037205 | 4/2005 |
| WO | WO 2005/037206 | 4/2005 |
| WO | WO 2005/060647 A2 | 7/2005 |
| WO | WO 2005/120483 | 12/2005 |
| WO | WO 2007/027582 A1 | 3/2007 |
| WO | WO 2007/099200 A1 | 9/2007 |
| WO | WO 2008/008433 | 1/2008 |
| WO | WO 2008/024456 | 7/2008 |
| WO | WO 2008/127717 | 10/2008 |

OTHER PUBLICATIONS

Buchwald et al. "Long-term, continuous intravenous heparin administration by an implantable infusion pump in ambulatory patients with recurrent venous thrombosis", Surgery. Oct. 1980;88(4):507-16.

Cabrespine et al. "Randomized Phase II study comparing paclitaxel and carboplatin versus mitoxantrone in patients with hormone-refractory prostate cancer", Urology. Feb. 2006;67(2):354-9.

Campfield et al., 1995, "Recombinant mouse OB protein: evidence for a peripheral signal linking adiposity and central neural networks" Science 269:546-549.

Considine et al., 1995, "Evidence against either a premature stop codon or the absence of obese gene mRNA in human obesity." J. Clin. Invest. 95:2986-2988.

Dalton et al.; "Discovery of Nonsteroidal Androgens", Biochem. Biophys. Res. Commun.,244(1):1-4, 1998.

Diebold et al.; "Innate antiviral responses by means of TLR7-mediated recognition of single-stranded RNA. Science", Mar. 5, 2004;303(5663):1529-31.

Djerassi et al., A New Look at Male Contraception, Nature, Jul. 7, 1994, pp. 11-12, vol. 370.

Edwards et al.; "New nonsteroidal androgen receptor modulators based on 4-(trifluoromethyl)-2-(1H)-Pyrololidino[3,2-g]quinolone", Bioorg. Med. Chem. Lett., 8: 745, 1998.

Edwards et al.; "Nonsteroidal androgen receptor agonists based on 4-(trifluoromethyl)-2H-pyrano[3,2-g]quinolin-2-one", Bioorg. Med. Chem. Lett., 9: 1003, 1999.

(56) References Cited

OTHER PUBLICATIONS

Eliason et al., "High Throughput Fluorescence Polarization-Based Screening Assays for the Identification of Novel Nuclear Receptor Ligands," Abstracts of Papers, 223rd ACS National Meeting, Orlando, FL, United States, (2002), Apr. 7, 2002.
European Search report for European Application No. 10075691.5 dated Dec. 10, 2012.
European Search report for European Application No. 14154215.9 dated Apr. 17, 2014.
Faulkner et al (1991) "Noninvasive measurements of bone mass, structure, and strength: current methods and experimental techniques." Am J Rosentgenology 157:1229-1237.
Francisco, et al., "Long-acting contraceptive agents: testosterone esters of unsaturated acids", Steroids, Jan. 1990, vol. 55, Butterworths.
Goodson, in Medical Applications of Controlled Release, supra, vol. 2, pp. 116-138 (1984).
Grundy et al. "Metabolic and health complications of obesity", Dis Mon. Dec. 1990;36(12):641-731.
Halaas et al., 1995, "Weight-reducing effects of the plasma protein encoded by the obese gene." Science 269:543-546.
Hamann et al.; "Discovery of a potent, orally active nonsteroidal androgen receptor agonist: 4-ethyl-1,2,3,4-tetrahydro-6-(trifluoromethyl)-8-pyridono[5,6-g]-quinoline (LG121071)", J. Med. Chem., 42: 210, 1999.
Hamilton et al., 1995, <<Increased obese mRNA expression in omental fat cells from massively obese humans. Nature Med. 1:953.
Hanada, et al (2003) "Bone anabolic effects of S-40503, a novel nonsteroidal selective androgen receptor modulator (SARM), in rat models of osteoporosis." Biol. Pharm. Bull. 26:1563-1569.
Handelsman, "Bridging the gender gap in contraception: another hurdle cleared" The Medical Journal of Australia, vol. 154, Feb. 18, 1996, pp. 230-233.
Heil et al.; "Species-specific recognition of single-stranded RNA via toll-like receptor 7 and 8", Science. Mar. 5, 2004;303(5663):1526-9.
Heitzman, Environ Qual Saf Suppl. 1976;(5):89-98.
Higuchi et al.; "4-Alkyl- and 3,4-diaklyl-1,2,3,4-tetrahydro-8-pyridono[5,6-g]quinolines: potent, nonsteroidal androgen receptor agonists", Bioorg. Med. Chem. Lett., 9:1335,1999.
Hoberman et al.; "The History of Synthetic Testosterone", Scientific American, Feb. 1995, pp. 76-81.
International Search Report for International Application No. PCT/US22/29336 dated Jul. 26, 2011.
International Search report for PCT/US07/15895 dated Jun. 24, 2008.
International Search report for PCT/US07/18686 dated Apr. 23, 2008.
International Search report for PCT/US05/19788 dated Jun. 16, 2006.
International Search report for PCT/US08/04816 dated Jul. 8, 2008.
International Search report for PCT/US12/32707 dated Jun. 21, 2012.
Kalu, (1991) "The ovariectomized rat model of postmenopausal bone loss", Bone Miner. 15 175-91.
Katre et al. "Chemical modification of recombinant interleukin 2 by polyethylene glycol increases its potency in the murine Meth A sarcoma model" Proc Natl Acad Sci U S A. 84(6):1487-91. Mar. 1987.
Kelly et al. "Dose escalation study of intravenous estramustine phosphate in combination with Paclitaxel and Carboplatin in patients with advanced prostate cancer", Clin Cancer Res. Jun. 2003;9(6):2098-107.
Kim et al.; "The Para Substituent of S-3-(Phenoxy)-2-hydroxy-2-methyl-N-(4-nitro-3-trifluoromethyl-phenyl)-propionamides Is a Major Structural Determinant of in Vivo Disposition and Activity of Selective Androgen Receptor Modulators", J Pharmacol Exp Ther. Oct. 2005; 315(1): 230-239.
Kirkovsky, et al., "[125I]-Radionated Bicalutamide Analogs as Potential Imaging Agents for Prostate Cancer", Poster Presentation MEDI 155, 214th ACS National Meeting, Las Vegas, NV, Sep. 7-11, 1997, Department of Pharmaceutical Sciences, University of Tennessee, Memphis, TN 38163.
Kirkovsky, et al., "Approaches to Irreversible non-steroidal chiral antiandrogens", Department of Pharmaceutical Sciences, University of Tennessee, 47th Southeast/51st Southwest Joint Regional Meeting of the American Chemical Society, Memphis, TN, Nov. 29-Dec. 1, 1995.
Kori et al. "Early Phase II Study of Combination Chemotherapy of Docetaxel and Carboplatin in Patients With Postoperative Recurrent Adenocarcinoma of the Lung", Apr. 20, 2002, Japanese Journal of Jung Cancer, vol. 42, No. 2, pp. 85-91.
Koski et al.; "Cutting edge: innate immune system discriminates between RNA containing bacterial versus eukaryotic structural features that prime for high-level IL-12 secretion by dendritic cells", J Immunol. Apr. 1, 2004;172(7):3989-93.
Laaksonen, D. E. et al, "Sex hormones, inflammation and the metabolic syndrome: a population-based study." European Journal of Endocrinology, 149(6), pp. 601-608, 2003.
Langer (1990) "New methods of drug delivery." Science 249:1527-1533.
Lonnquist et al. "Overexpression of the obese (ob) gene in adipose tissue of human obese subjects", Nat Med. Sep. 1995;1(9):950-3.
Lopez-Berestein, Treatment of Systemic Fungal Infections with Liposomal-Amphotericin B, Liposomes in the Therapy of Infectious Diseases and Cancer, 1989, pp. 317-327.
MacDonald et al.; "Understanding and managing cancer cachexia", J. American College of Surgeons, vol. 197, pp. 143-161, 2003.
Matsumoto, 1994, "Hormonal therapy of male hypogonadism" Endocrinol. Met. Clin. N. Am. 23:857-75.
McKillop, et al., "Enantioselective metabolism and pharmacokinetics of Casodex in the male rat", Xenobiotica, 1995, vol. 25, No. 6, 623-634.
Mohler et al., Informa Healthcare, Nonsteroidal Tissue Selective Androgen Receptor Modulators: A Promising Class of Clinical Candidates, Nov. 2005, vol. 15, pp. 1565-1585.
Monaco et al. "Cloning of the Duchenne/Becker muscular dystrophy locus", Adv Hum Genet. 1988;17:61-98.
Narayanan et al., Selective Androgen Receptor Modulators in Preclinical Development, The Open Access Journal of the Nuclear Receptor Signaling Atlas, 2008, pp. 1-26, vol. 6.
Narayanan et al., Steroidal Androgens and Nonsteroidal Tissue-Selective Androgen Receptor Function Through Distinct Genomic and Nongenomic Signaling Pathways, The Endocrine Society, 2008, pp. 2448-2465.
Negro-Vilar, (1999) "Selective androgen receptor modulators (SARMs): a novel approach to androgen therapy for the new illennium." J. Clin. Endocrin Metabol. 84: 3459-3462.
Office action for JP 2013-501372 dated Oct. 14, 2014.
Office Action for Japanese Application No. 2014-005551 mailed Jan. 27, 2015.
Pelleymounter et al., 1995, "Effects of the obese gene product on body weight regulation in ob/ob mice." Science 269:540-543.
Rosen et al.; "Intracellular receptors and signal transducers and activators of transcription superfamilies: novel targets for small-molecule drug discovery",J. Med. Chem., 38: 4855, 1995.
Rosen et al; "Novel, non-steroidal, selective androgen receptor modulators (SARMs) with anabolic activity in bone and muscle and improved safety profile", J Musculoskel Neuron Interact 2002; 2(3):222-224.
Saudek et al. "A preliminary trial of the programmable implantable medication system for insulin delivery", N Engl J Med. Aug. 31, 1989;321(9):574-9.
Sefton, 1987, "Implantable pumps." CRC Crit. Ref. Biomed. Eng. 14:201.
Silverman, "The Organic Chemistry of Drug Design and Drug Action", Academic Press, 1992, pp. 15-22.
Singh et al., 2003, "Androgens stimulate myogenic differentiation and inhibit adipogenesis in C3H 10T1/2 pluripotent cells through an androgen receptor-mediated pathway." Endocrinology, 144(11):5081-8.
Supplementary European Search report for European Application No. 05758756.0 dated Jun. 5, 2008.

(56) References Cited

OTHER PUBLICATIONS

Supplementary European Search report for European application No. 08742872.8 dated Jul. 13, 2010.
Supplementary European Search report for European Application No. 07796823.8 dated Dec. 1, 2010.
Supplementary European Search report for European Application No. 07837277.8 dated Dec. 1, 2010.
Treat et al., in Liposomes in the Therapy of Infectious Disease and Cancer, Lopez-Berestein and Fidler (eds.), Liss, New York, pp. 353-365 (1989).
Tucker et al.; J. Med Chem. 1988, 31, pp. 885-887, "Resolution of the Nonsteroidal Antiandrogen—4'-Cyano-3-[(4-fluorophenyl)sulfonyl]-2-hydroxy-2-methyl-3'-(trifluoromethyl)-propionanilide and the Determination of the Absolute Configuration of the Active Enantiomer".
Wahner, et al (1984) "Assessment of Bone Mineral Part 1 " J Nucl. Medicine, 1134-1141.
Wahner, et al (1985) "Bone Mineral Density of the Radius" J. Nucl Medicine 26 13-39.
World Health Organisation Task Force on Methods for the Regulation of Male Fertility, "Contraceptive efficacy of testosterone-induced azoospermia in normal men", The Lancet, vol. 336, Oct. 20, 1990, pp. 955-959and 1517-1518.
Wu, "Male Contraception: Current Status and Future Prospects", Clinical Endocrinology, (1988), 29, pp. 443-465.
Xiao et al., Effects of Ractopamine at Difference Dietary Protein Levels on Growth Performance and Carcass Characteristics in Finishing Pigs, Animal Feed Science and Technology, 1999, pp. 119-127.
Yepuru et al., An Androgen Receptor-b Specific Selective Estrogen Receptor Modulator (SERM) Inhibits the Growth of the Prostate Cancer Cells and Stromal-Epithilial Tumor Xenograft, The Endocrine Society, Jun. 2007, pp. 81-82.
Zhi et al.; "Switching androgen receptor antagonists to agonists by modifying C-ring substituents on piperidino[3,2-g]quinolone", Bioorg. Med. Chem. Lett., 9: 1009, 1999.
Zilbermint et al.; "Nonsteroidal selective androgen receptor modulator OstarineTM in cancer cachexia", Future Oncol., 2009, 5(8), pp. 1211-1220.
Narayanan, et al "Steroidal Androgens and Nonsteroidal, Tissue Selective Androgen Receptor Modulators (SARM) Regulate Androgen Receptor Function Through Distinct Genomic and Non-Genomic Signaling Pathways." The Endocrine Society—Programs and Abstracts—89th Annual Meeting—Paper P1-595. (2007).

\* cited by examiner

Synthetic Scheme for (S)-II Compound:

Synthetic Scheme for (S)-II (oxirane intermediate) Compound:

Synthetic Scheme for (R)-II (oxirane intermediate) Compound:

Synthetic Scheme for (R)-II Using Chiral Intermediate and Involving B-ring Addition Prior to A-ring Addition:

Synthetic Scheme for Racemic Compound II Involving Oxazolidinedione Intermediate:

Large-Scale Synthetic Scheme for (S)-II :

Compound of Formula S-II in castrated Rats

Synthetic Scheme for (S)-XXIII Compound

SARMS AND METHOD OF USE THEREOF

CROSS REFERENCE TO RELATED APPLICATIONS

This Application is a Continuation-in-Part application of U.S. patent application Ser. No. 14/168,993, filed Jan. 30, 2014, which is a Continuation Application of U.S. patent application Ser. No. 13/627,900 filed Sep. 26, 2012 now U.S. Pat. No. 8,669,286, which is a Continuation Application of U.S. patent application Ser. No. 12/730,094 filed Mar. 23, 2010, now U.S. Pat. No. 8,309,603; and U.S. patent application Ser. No. 14/168,993 is a Continuation in Part Application of U.S. patent application Ser. No. 13/868,768 filed Apr. 23, 2013, now U.S. Pat. No. 8,846,756, which is a Continuation Application from U.S. patent application Ser. No. 13/302,988 filed Nov. 22, 2011, now U.S. Pat. No. 8,426,465, which is a Divisional Application from U.S. patent application Ser. No. 11/892,595, filed Aug. 24, 2007 now U.S. Pat. No. 8,080,682, which claims the benefit of U.S. Provisional Application Ser. No. 60/839,665, filed Aug. 24, 2006, and U.S. Provisional Application Ser. No. 60/907,749, filed Apr. 16, 2007; all of which are hereby incorporated by reference in their entirety.

GOVERNMENT INTEREST STATEMENT

This invention was made in whole or in part with government support under grant number R01 DK598006, awarded by the National Institute of Health; under grant number R29 CA068096 awarded by the National Cancer Institute, National Institute of Health; under grant number R15 HD35329, awarded by the National Institute of Child Health and Human Development, National Institute of Health and under grant number R01 DK59800, awarded by the National Institute of Health. The government may have certain rights in the invention.

FIELD OF THE INVENTION

This invention provides substituted acylanilide compounds and uses thereof in treating a variety of diseases or conditions in a subject, including, inter alia, a muscle wasting disease and/or disorder such as muscular dystrophies including Duchenne muscular dystrophy and Becker muscular dystrophy.

BACKGROUND OF THE INVENTION

Muscle wasting refers to the progressive loss of muscle mass and/or to the progressive weakening and degeneration of muscles, including the skeletal or voluntary muscles, which control movement, cardiac muscles, which control the heart (cardiomyopathies), and smooth muscles. Chronic muscle wasting is a chronic condition (i.e. persisting over a long period of time) characterized by progressive loss of muscle mass, and weakening and degeneration of muscle.

The loss of muscle mass that occurs during muscle wasting can be characterized by muscle protein degradation by catabolism. Protein catabolism occurs because of an unusually high rate of protein degradation, an unusually low rate of protein synthesis, or a combination of both. Muscle protein catabolism, whether caused by a high degree of protein degradation or a low degree of protein synthesis, leads to a decrease in muscle mass and to muscle wasting.

Muscle wasting is associated with chronic, neurological, genetic or infectious pathologies, diseases, illnesses or conditions. These include muscular dystrophies such as Duchenne muscular dystrophy, Becker muscular dystrophy, limb-girdle disease, and myotonic dystrophy; muscle atrophies such as post-polio muscle atrophy (PPMA); cachexias such as cardiac cachexia, AIDS cachexia and cancer cachexia; and malnutrition, leprosy, diabetes, renal disease, chronic obstructive pulmonary disease (COPD), cancer, end stage renal failure, sarcopenia, emphysema, osteomalacia, HIV infection, AIDS, and cardiomyopathy.

In addition, other circumstances and conditions are linked to and can cause muscle wasting. These include chronic lower back pain, advanced age, central nervous system (CNS) injury, peripheral nerve injury, spinal cord injury, chemical injury, central nervous system (CNS) damage, peripheral nerve damage, spinal cord damage, chemical damage, burns, disuse deconditioning that occurs when a limb is immobilized, long term hospitalization due to illness or injury, and alcoholism.

An intact androgen receptor (AR) signaling pathway is crucial for appropriate development of skeletal muscles. Furthermore, an intact AR-signaling pathway increases lean muscle mass, muscle strength and muscle protein synthesis.

Muscle wasting, if left unabated, can have dire health consequences. For example, the changes that occur during muscle wasting can lead to a weakened physical state that is detrimental to an individual's health, resulting in increased susceptibility to bone fracture and poor physical performance status. In addition, muscle wasting is a strong predictor of morbidity and mortality in patients suffering from cachexia and AIDS.

Duchenne muscular dystrophy is the most common of nine muscular dystrophies and occurs in 1/3500 to 1/5000 males around the world. Duchenne muscular dystrophy patients experience difficulty with walking at 3-5 years of age, progressive worsening of symptoms, and death in the teens to $3^{rd}$ decade. Discovered in the 1860's, little was known about the pathogenesis of Duchenne muscular dystrophy until 1986 when the gene underlying this X-linked autosomal recessive disease was cloned and characterized. The gene was named dystrophin (DMD) and found to be part of a sarcolemma (i.e. myocte plasma membrane) protein complex (dystrophin-glycoprotein complex) which connects the myofibril (muscle cell) cytoskeleton to the extracellular matrix, thereby protecting the muscle cell membrane from physical trauma during muscle exertion and exercise. Duchenne muscular dystrophy is predominantly a disease in males and is associated with a variety of mutations of the DMD gene which leads to a wide variation of disease severities. Sarcolemma fragility produces progressive calcium permeability, protease activation, oxidative stress, and inflammation which causes progressive replacement of muscle cells by fibrous tissue and/or conversion to fat. Gross pathology includes weakness and degeneration of skeletal and voluntary muscle which is exacerbated by high impact exercise, muscle contractures that worsen mobility if not corrected, and scoliosis. Although braces and walkers provide some protection, declines in physical function result in loss of ambulation during childhood leading to wheelchair confinement, and eventually impaired cardiac (cardiomyopathy) or respiratory (diaphragm fibrosis) function leads to death. Average life expectancy has improved (and rare cases of men living into their $4^{th}$ or $5^{th}$ decade) as a result of better respiratory (glucocorticoids) and cardiac (ACE inhibitors, angiotensin receptor blockers, and beta-blockers) supportive care but no disease-modifying therapeutics exist. Anabolics (steroidal androgens, IGF-I, etc.) to slow the rate of physical function decline have been proposed and were shown to provide some benefit in small clinical trials, but no non-steroidal or tissue-selective androgen receptor modulator (SARM) has entered clinic testing for Duchenne muscular dystrophy. The loss of gene function etiology has attracted great interest toward gene therapy approaches to treat the disease; however, such treatments have not completely reversed the phenotype and suffer from difficulties inherent in nucleotide polymer based therapeutics which are exacerbated by the large and complex nature of the dystrophin gene. The above suggests that other therapeutic targets are urgently needed. Consequently, there is increasing interest in further improving the quality of life and length of life via symptom directed supportive care. Aryl propanamide SARMs have been shown to increase global anabolic tone in multiple clinical trials through increases in muscle mass (lean body mass by DEXA) and physical function (e.g., leg press, grip strength, stair climb power) suggesting that they may have therapeutic effects on dystrophic skeletal and specifically diaphragm muscle, cardiac, and smooth muscle, or may delay onset or improve symptoms of loss of mobility/autonomy, cardiomyopathy, or respiratory insufficiency in Duchenne muscular dystrophy or Becker muscular dystrophy and other muscular dystrophy patients.

Becker muscular dystrophy is a rarer and milder variation of Duchenne muscular dystrophy caused by DMD mutants that do not completely abrogate dystrophin glycoprotein complex function in males or more commonly it is observed in some female carriers (Duchenne muscular dystrophy is often asymptomatic in females). Becker muscular dystrophy has a phenotype with less functional impairment and longer life expectancy, but clinical cardiomyopathies and respiratory insufficiencies must be closely monitored.

Interest in drug design for Duchenne muscular dystrophy was hampered by the lack of good models of this disease, however several in vivo disease models now exist. These include the dystrophin gene deletion in mice (mdx mice; denoted by DMD (−/−)) which presents a phenotype representative of the early stages of the disease in humans however, is not progressive in symptomology and much less severe in the later stages of the disease. Double-knockout (knock-down) mice lacking dystrophin (DMD) and utrophin (UTRN, a protein that can partially compensate for lack of dystrophin) (i.e., DMD (−/−) UTRN (−/−)) present a phenotype more representative of the natural history of Duchenne muscular dystrophy in humans including progressive worsening of symptoms, loss of ambulation at ~12 weeks, and early death by ~20 weeks. [A severe phenotype can also be derived from the mdx model by forced treadmill running.] Golden retriever muscular dystrophy is another disease model that matches the human phenotype in some ways but suffers from a high level of interindividual variation even among littermates, complicating the interpretation of results. Although the pathogenesis of other muscular dystrophies is not related to Duchenne and Becker muscular dystrophies, the phenotypes therein suggest that activity in the mdx and double knockout models may be indicative of therapeutic efficacies in those disease states as well.

While there are many treatments and therapies for these conditions, none are ideal. Since the androgen receptor (AR) signaling pathway has been shown to increase lean muscle mass, muscle strength and muscle protein synthesis, and since hypogonadism accompanies these conditions, molecules targeting the AR signaling pathway may be useful in treating these diseases and/or conditions.

SUMMARY OF THE INVENTION

In one embodiment, the present invention is directed to a method of treating, reducing the severity, reducing the incidence, delaying the onset, or reducing the pathogenesis of Duchenne muscular dystrophy in a subject in need thereof, comprising the step of administering to said subject a selective androgen receptor modulator (SARM) compound represented by the structure of formula S-XXIII:

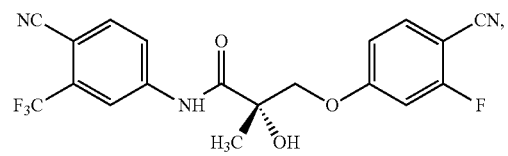

S-XXIII or its isomer, pharmaceutically acceptable salt, hydrate, N-oxide, or any combination thereof.

In one embodiment, the administering of the present invention comprises administering a pharmaceutical composition comprising said compound and/or its isomer, pharmaceutically acceptable salt, hydrate, N-oxide, or any combination thereof; and a pharmaceutically acceptable carrier.

In one embodiment, the present invention further increases the physical function of said subject.

In one embodiment, the present invention further increases the quality of life of said subject.

In one embodiment, the present invention increases the survival of said subject.

In one embodiment, the present invention delays onset or improves symptoms of cardiomyopathy and/or respiratory function.

In one embodiment, this invention is directed to a method of increasing the physical function of a subject suffering from Duchenne muscular dystrophy, comprising the step of administering to said subject a selective androgen receptor modulator (SARM) compound represented by the structure of formula S-XXIII:

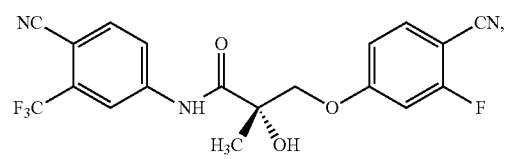

S-XXIII or its isomer, pharmaceutically acceptable salt, hydrate, N-oxide, or any combination thereof.

In one embodiment, this invention is directed to a method of increasing the quality of life of a subject suffering from Duchenne muscular dystrophy, comprising the step of administering to said subject a selective androgen receptor modulator (SARM) compound represented by the structure of formula S-XXIII:

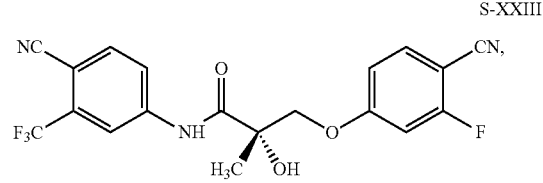 [SMILES: C[C@](O)(COc1ccc(C#N)c(F)c1)C(=O)Nc1ccc(C#N)c(C(F)(F)F)c1]

S-XXIII or its isomer, pharmaceutically acceptable salt, hydrate, N-oxide, or any combination thereof.

In one embodiment, this invention is directed to a method of increasing the survival of a subject suffering from Duchenne muscular dystrophy, comprising the step of administering to said subject a selective androgen receptor modulator (SARM) compound represented by the structure of formula S-XXIII:

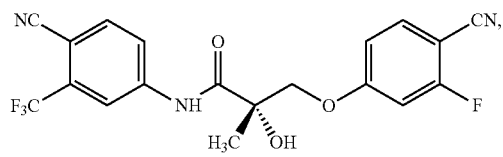

S-XXIII or its isomer, pharmaceutically acceptable salt, hydrate, N-oxide, or any combination thereof.

In one embodiment, the present invention is directed to a method of treating, reducing the severity, reducing the incidence, delaying the onset, or reducing the pathogenesis of cardiomyopathy in a subject suffering from Duchenne muscular dystrophy, comprising the step of administering to said subject a selective androgen receptor modulator (SARM) compound represented by the structure of formula S-XXIII:

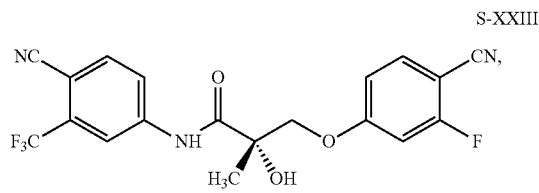 [SMILES: C[C@](O)(COc1ccc(C#N)c(F)c1)C(=O)Nc1ccc(C#N)c(C(F)(F)F)c1]

S-XXIII or its isomer, pharmaceutically acceptable salt, hydrate, N-oxide, or any combination thereof.

In one embodiment, the present invention is directed to a method of treating, reducing the severity, reducing the incidence, delaying the onset, or reducing the pathogenesis of respiratory failure in a subject suffering from Duchenne muscular dystrophy, comprising the step of administering to said subject a selective androgen receptor modulator (SARM) compound represented by the structure of formula S-XXIII:

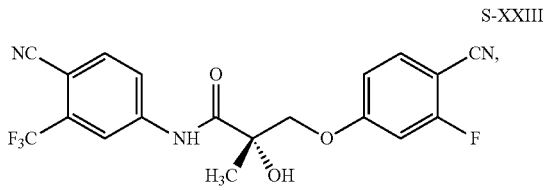 [SMILES: C[C@](O)(COc1ccc(C#N)c(F)c1)C(=O)Nc1ccc(C#N)c(C(F)(F)F)c1]

S-XXIII or its isomer, pharmaceutically acceptable salt, hydrate, N-oxide, or any combination thereof.

In one embodiment, this invention is directed to a method of treating, reducing the severity, reducing the incidence, delaying the onset, or reducing the pathogenesis of Becker muscular dystrophy or myotonic dystrophy in a subject in need thereof, comprising the step of administering to said subject a selective androgen receptor modulator (SARM) compound represented by the structure of formula S-XXIII:

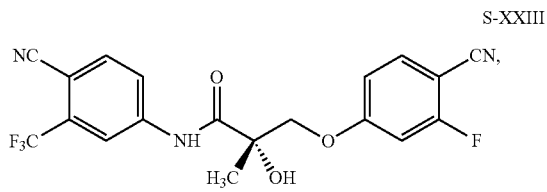

S-XXIII or its isomer, pharmaceutically acceptable salt, hydrate, N-oxide, or any combination thereof.

In one embodiment, this invention is directed to a method of treating, reducing the severity, reducing the incidence, delaying the onset, or reducing the pathogenesis of myotonic dystrophy, limb-girdle muscular dystrophy, facioscapulhumeral muscular dystrophy, congenital muscular dystrophy, oculopharyngeal muscular dystrophy, distal muscular dystrophy, or Emery-Dreifuss muscular dystrophy in a subject in need thereof, comprising the step of administering to said subject a selective androgen receptor modulator (SARM) compound represented by the structure of formula S-XXIII:

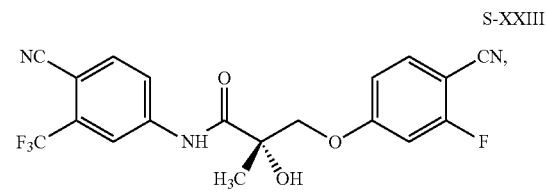

S-XXIII or its isomer, pharmaceutically acceptable salt, hydrate, N-oxide, or any combination thereof.

In one embodiment, this invention provides a method of treating, reducing the severity, reducing the incidence, delaying the onset, or reducing the pathogenesis of cardiovascular disease in a human subject suffering from Duchenne muscular dystrophy comprising the step of administering an effective amount of a compound of formula S-XXIII or its isomer, pharmaceutically acceptable salt, pharmaceutical product, crystal, N-oxide, hydrate or any combination thereof to said subject.

In one embodiment, this invention provides a method of treating, reducing the severity, reducing the incidence, delaying the onset, or reducing the pathogenesis of cardiovascular disease in a human subject suffering from Becker muscular dystrophy comprising the step of administering an effective amount of a compound of formula S-XXIII or its isomer, pharmaceutically acceptable salt, pharmaceutical product, crystal, N-oxide, hydrate or any combination thereof to said subject.

In one embodiment, this invention provides a method of treating, reducing the severity, reducing the incidence, delaying the onset, or reducing the pathogenesis of cardiovascular disease in a human subject suffering from myotonic dystrophy comprising the step of administering an effective amount of a compound of formula S-XXIII or its isomer, pharmaceutically acceptable salt, pharmaceutical product, crystal, N-oxide, hydrate or any combination thereof to said subject.

In one embodiment, the present invention provides a method of reducing a fat mass in a subject suffering from Duchenne muscular dystrophy comprising the step of administering an effective amount of a compound of formula S-XXIII or its isomer, pharmaceutically acceptable salt, pharmaceutical product, crystal, N-oxide, hydrate or any combination thereof to the subject.

In one embodiment, the present invention provides a method of reducing a fat mass in a subject suffering from Becker muscular dystrophy comprising the step of administering an effective amount of a compound of formula S-XXIII or its isomer, pharmaceutically acceptable salt, pharmaceutical product, crystal, N-oxide, hydrate or any combination thereof to the subject.

In one embodiment, the present invention provides a method of reducing a fat mass in a subject suffering from myotonic dystrophy comprising the step of administering an effective amount of a compound of formula S-XXIII or its isomer, pharmaceutically acceptable salt, pharmaceutical product, crystal, N-oxide, hydrate or any combination thereof to the subject.

In one embodiment, the present invention provides a method of increasing a lean mass in a subject suffering from Duchenne muscular dystrophy comprising the step of administering an effective amount of a compound of formula S-XXIII or its isomer, pharmaceutically acceptable salt, pharmaceutical product, crystal, N-oxide, hydrate or any combination thereof to the subject.

In one embodiment, the present invention provides a method of increasing a lean mass in a subject suffering from Becker muscular dystrophy comprising the step of administering an effective amount of a compound of formula S-XXIII or its isomer, pharmaceutically acceptable salt, pharmaceutical product, crystal, N-oxide, hydrate or any combination thereof to the subject.

In one embodiment, the present invention provides a method of increasing a lean mass in a subject suffering from myotonic dystrophy comprising the step of administering an effective amount of a compound of formula S-XXIII or its isomer, pharmaceutically acceptable salt, pharmaceutical product, crystal, N-oxide, hydrate or any combination thereof to the subject.

BRIEF DESCRIPTION OF THE DRAWINGS

The present invention will be understood and appreciated more fully from the following detailed description taken in conjunction with the appended drawings in which:

FIG. 1A is a synthetic scheme for the preparation of an (S) enantiomer of a compound of formula II (S-II). FIG. 1B is a synthetic scheme for the preparation of an (R) enantiomer of a compound of formula II (R-II). FIG. 1C is a synthetic scheme for the preparation of an (S) enantiomer of a compound of formula II (S-II) including an oxirane intermediate. FIG. 1D is a synthetic scheme for the preparation of an (R) enantiomer of a compound of formula II (R-II) including an oxirane intermediate. FIG. 1E is a synthetic scheme for the preparation of an (S) enantiomer of a compound of formula II (S-II) involving B-ring addition prior to A-ring addition. FIG. 1F is a synthetic scheme for the preparation of an (R) enantiomer of a compound of formula II (R-II) involving B-ring addition prior to A-ring addition. FIG. 1G is a synthetic scheme for the preparation of an (S) enantiomer of a compound of formula II (S-II) using 2-tribromomethyl-[1,3]dioxolan-4-one intermediate and involving B-ring addition prior to A-ring addition. FIG. 1H is a synthetic scheme for the preparation of an (R) enantiomer of a compound of formula II (R-II) using 2-tribromomethyl-[1,3]dioxolan-4-one intermediate and involving B-ring addition prior to A-ring addition. FIG. 1I is a synthetic scheme for preparation of a racemic mixture of a compound of formula II, involving oxazolidinedione intermediate and B ring addition prior to A ring. FIG. 1J is a synthetic scheme for preparation of a racemic mixture of a compound of formula II, involving an oxirane intermediate and A ring addition prior to B ring. FIG. 1K is a synthetic scheme for preparation of a large scale of an (S) enantiomer of a compound of formula II (S-II). FIG. 1L is a synthetic scheme for preparation of a large scale of an (S) enantiomer of a compound of formula II (S-II), including an oxirane intermediate.

FIG. 5A shows the increase of average daily gain (ADG) over the course of the study. FIG. 5B shows the decrease feed to gain ratio. FIG. 5C shows the increased fat free lean gain per day. FIG. 5D shows an increase in ADG for days 21-28.

FIG. 14A shows the effects of S-XXIII on body weight in DMD (−/−) UTRN (+/+) mice. FIG. 14B shows the effects of S-XXIII on fat mass in DMD (−/−) UTRN (+/+) mice. FIG. 14C shows the effects of S-XXIII on lean mass in DMD (−/−) UTRN (+/+) mice. FIG. 14D shows the effects of S-XXIII on grip strength in DMD (−/−) UTRN (+/+) mice.

FIG. 15A shows the effects of S-XXIII on body weight of DMD (−/−) UTRN (−/−) mice. FIG. 15B shows the effects of S-XXIII on lean mass of DMD (−/−) UTRN (−/−) mice. FIG. 15C shows the effects of S-XXIII on grip strength in DMD (−/−) UTRN (−/−) mice. N=6-9 in each group.

FIG. 16A shows cumulative data whereas FIG. 16B shows data from mice from the same litter (each group of two bars represents one litter). Despite similar characteristics at birth, mice treated with 'SARM' or S-XXIII, respectively, exhibited increased survival than mice treated with vehicle.

FIGS. 18A-180 show the effects of S-XXIII on cardiac function in DMD (−/−) UTRN (+/+) mice via echocardiography results. FIG. 18A shows the effects of S-XXIII on ejection fraction (%).

DETAILED DESCRIPTION OF THE PRESENT INVENTION

Figure 1A:
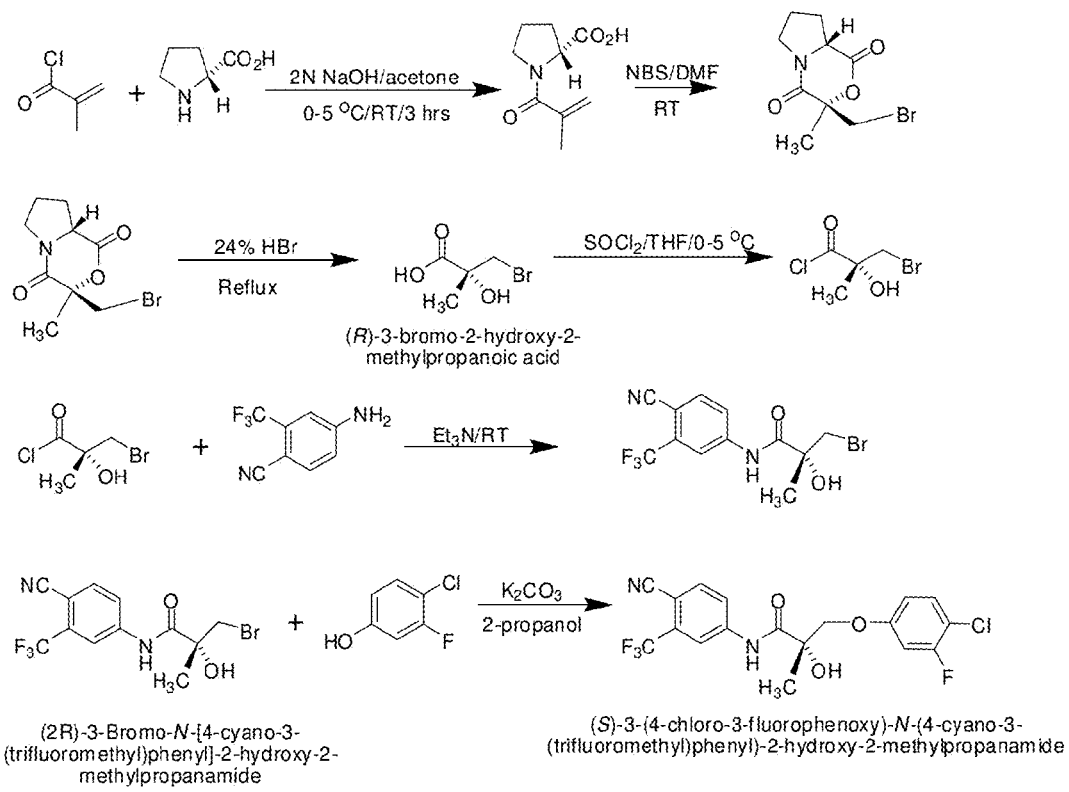
FIGS. 1A-1L: Synthetic schemes for the preparation of compound of formula II.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

This invention provides, in one embodiment, feed composition for animals comprising acylanilides characterized by the structure of formulas I-XXV. In one embodiment, the compound is a SARM. In one embodiment, the compound and/or feed composition is useful in affecting the carcass composition, increasing the lean mass, reducing the fat mass of an animal or reducing percent fat mass, increasing feed efficiency, increasing average daily gain (ADG), decreasing feed to gain ratio (F:G) of an animal, including a feedlot animal, a beef cattle or a finishing livestock. In another embodiment, the compound and/or feed composition is useful in increasing muscle growth of an animal, modulation of meat quality, or enhancing productive life of animals including feedlot animals, beef cattle and finishing livestock.

In one embodiment, the compounds of this invention provide compounds, compositions and methods of treating a variety of conditions or diseases, including, inter alia, oral testosterone replacement therapy, male contraception, maintaining sexual desire in women, osteoporosis, treating prostate cancer and/or imaging prostate cancer. In some embodiments, the compounds of this invention are nonsteroidal ligands for the AR and exhibit androgenic and/or anabolic activity. In some embodiments, the compounds are partial agonists or partial antagonists in a tissue selective manner. In some embodiments, the compounds are full agonists or full antagonists in a tissue selective manner, which in some embodiments, allows for tissue-selective androgenic and/or anabolic effects. These agents may be active alone or in combination with progestins or estrogens, or other agents, as herein described. In other embodiments, the agents are agonists, antagonists, partial agonists or partial antagonists.

In some embodiments, this invention provides compounds, which are useful in androgen replacement therapy (ART), useful in: a) improving body composition; b) increasing bone mineral density (BMD); c) increasing bone mass; d) increasing bone strength; e) improving bone function; f) decreasing fracture risk; g) increasing muscle strength; h) increasing muscle function; i) improving exercise tolerance; j) enhancing libido; k) improving sexual performance; l) improving mood; and/or m) improving cognition.

In some embodiments, this invention provides synthetic processes of preparation of the SARM compounds of this invention. In some embodiments, the invention provides compositions comprising the selective androgen receptor modulator compounds or use of the same for binding an AR, modulating spermatogenesis, bone formation and/or resorption, treating muscle wasting or diseases associated with muscle wasting, treating prostate cancer, and/or providing hormonal therapy for androgen-dependent conditions.

In one embodiment, the present invention provides, a compound of formula (I):

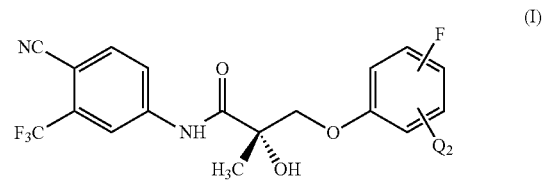

wherein $Q_2$ is alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, or SR; and R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

or its isomer, pharmaceutically acceptable salt, pharmaceutical product, N-oxide, hydrate or any combination thereof.

In one embodiment, the present invention provides, a compound of formula S-II:

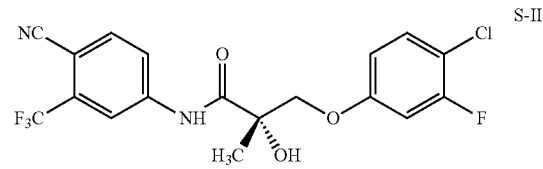

or its isomer, pharmaceutically acceptable salt, pharmaceutical product, N-oxide, hydrate or any combination thereof.

In one embodiment, the present invention provides, a compound represented by the structure of formula III:

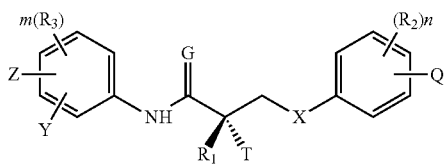 III wherein X is a bond, O, CH$_2$, NH, Se, PR, NO or NR;
G is O or S;
T is OH, OR, —NHCOCH$_3$, or NHCOR;
R is alkyl, haloalkyl, dihaloalkyl, trihaloalkyl, CH$_2$F, CHF$_2$,
CF$_3$, CF$_2$CF$_3$, aryl, phenyl, halogen, alkenyl or OH;
R$_1$ is CH$_3$, CH$_2$F, CHF$_2$, CF$_3$, CH$_2$CH$_3$, or CF$_2$CF$_3$;
R$_2$ is H, F, Cl, Br, I, CH$_3$, CF$_3$, OH, CN, NO$_2$, NHCOCH$_3$, NHCOCF$_3$, NHCOR, alkyl, arylalkyl, OR, NH$_2$, NHR, N(R)$_2$, or SR;
R$_3$ is H, F, Cl, Br, I, CN, NO$_2$, COR, COOH, CONHR, CF$_3$, or Sn(R)$_3$; or
R$_3$ together with the benzene ring to which it is attached forms a fused ring system represented by the structure:

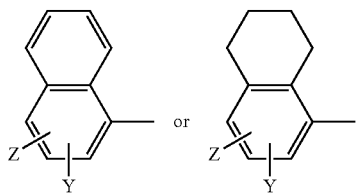

Z is NO$_2$, CN, Cl, F, Br, I, H, COR, COOH, or CONHR;
Y is CF$_3$, alkoxy, alkyl, hydroxyalkyl, alkylaldehyde, formyl, H, F, Br, Cl, I, CN, or Sn(R)$_3$;
Q is H, alkyl, halogen, CF$_3$, CN, C(R)$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OH, OR, COR, OCOR, OSO$_2$R, SO$_2$R, or SR; or Q together with the benzene ring to which it is attached is a fused ring system represented by structure A, B or C:

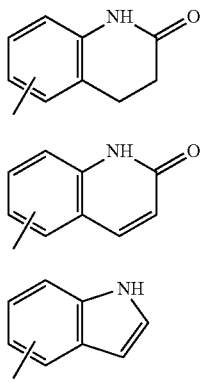

n is an integer of 1-4; and
m is an integer of 1-3;
or an isomer, pharmaceutically acceptable salt, pharmaceutical product, N-oxide, hydrate thereof or any combination thereof.

In one embodiment, the present invention provides, a feed composition for an animal comprising a compound of formula IIIA:

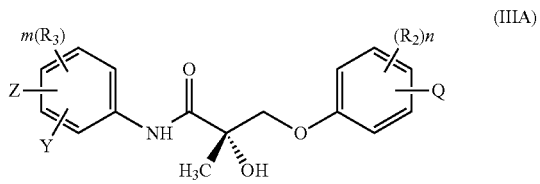 (IIIA)

wherein
Z is NO$_2$, CN, Cl, F, Br, I, H, COR, COOH, or CONHR;
Y is CF$_3$, alkoxy, alkyl, hydroxyalkyl, alkylaldehyde, formyl, H, F, Br, Cl, I, CN, or Sn(R)$_3$;
R is alkyl, haloalkyl, dihaloalkyl, trihaloalkyl, CH$_2$F, CHF$_2$, CF$_3$, CF$_2$CF$_3$, aryl, phenyl, halogen, alkenyl or OH;
R$_2$ is H, F, Cl, Br, I, CH$_3$, CF$_3$, OH, CN, NO$_2$, NHCOCH$_3$, NHCOCF$_3$, NHCOR, alkyl, arylalkyl, OR, NH$_2$, NHR, N(R)$_2$, or SR;
R$_3$ is H, F, Cl, Br, I, CN, NO$_2$, COR, COOH, CONHR, CF$_3$, or Sn(R)$_3$;
Q is H, alkyl, halogen, CF$_3$, CN, C(R)$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OH, OR, COR, OCOR, OSO$_2$R, SO$_2$R, or SR;
n is an integer of 1-4; and
m is an integer of 1-3;
or its isomer, pharmaceutically acceptable salt, crystal, N-oxide, hydrate or any combination thereof to said subject.

In one embodiment, the present invention provides a compound of formula III wherein X is O. In another embodiment, the present invention provides a compound of formula III wherein T is OH. In another embodiment, the present invention provides a compound of formula III wherein R$_1$ is CH$_3$. In another embodiment, the present invention provides a compound of formula III or IIIA wherein Z is CN. In another embodiment, the present invention provides a compound of formula III or IIIA wherein Z is F. In another embodiment, the present invention provides a compound of formula III or IIIA wherein Z is NO$_2$. In another embodiment, the present invention provides a compound of formula III or IIIA, wherein Y is CH$_3$. In another embodiment, the present invention provides a compound of formula III or IIIA, wherein Y is H. In another embodiment, the present invention provides a compound of formula III or IIIA wherein Y is CF$_3$. In another embodiment, the present invention provides a compound of formula III or IIIA, wherein Y is Cl. In another embodiment, the present invention provides a compound of formula III or IIIA wherein R$_3$ is H and none of Y, Z, Q or R$_2$ are H. In another embodiment, the present invention provides a compound of formula III or IIIA wherein R$_3$ is CN. In another embodiment, the present invention provides a compound of formula III or IIIA wherein R$_3$ is Cl. In another embodiment, the present invention provides a compound of formula III or IIIA wherein R$_3$ is F. In another embodiment, the present invention provides a compound of formula III or IIIA wherein Q is CN. In another embodiment, the present invention provides a compound of formula III or IIIA wherein Q is F. In another embodiment, the present invention provides a compound of formula III or IIIA wherein Q is Cl. In another embodiment, if $R_3$ of formula III or IIIA is H, then none of Z or Y or $R_2$ or Q are H.

In one embodiment, the present invention provides a compound characterized by the structure of formula IV:

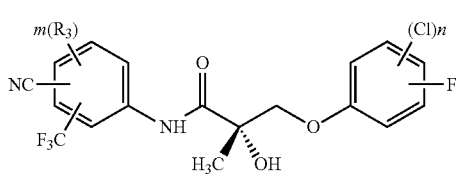

IV wherein $R_3$, m and n are as described for the structure of formula III.

In one embodiment, this invention provides a compound of formula S-XXIII:

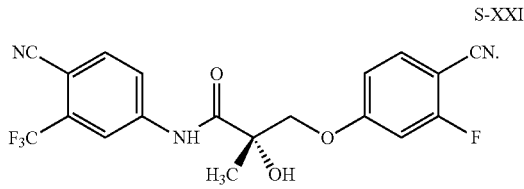

S-XXIII

In one embodiment, this invention provides a compound of formula XXIV:

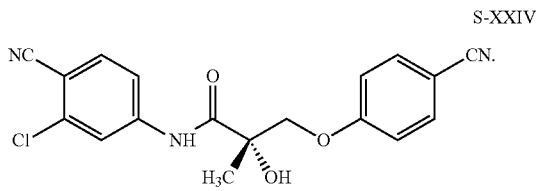 [SMILES: C[C@](O)(COc1ccc(C#N)cc1)C(=O)Nc1ccc(C#N)c(Cl)c1]

S-XXIV

In one embodiment, this invention provides a compound of formula XXV:

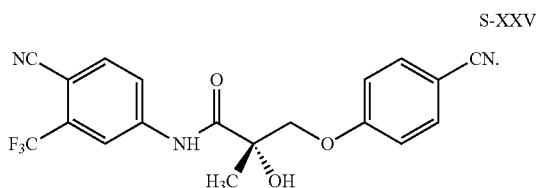

S-XXV

In one embodiment, this invention provides an analog of the compound of formulas I-XXV. In another embodiment, this invention provides a derivative of the compound of formulas I-XXV. In another embodiment, this invention provides a prodrug of the compound of formulas I-XXV. In another embodiment, this invention provides a metabolite of the compound of formulas I-XXV. In another embodiment, this invention provides a pharmaceutically acceptable salt of the compound of formulas I-XXV. In another embodiment, this invention provides a pharmaceutical product of the compound of formulas I-XXV. In another embodiment, this invention provides a hydrate of the compound of formulas I-XXV. In another embodiment, this invention provides an N-oxide of the compound of formulas I-XXV. In another embodiment, this invention provides a polymorph of the compound of formulas I-XXV. In another embodiment, this invention provides a crystal of the compound of formulas I-XXV. In another embodiment, this invention provides an impurity of the compound of formulas I-XXV. In another embodiment, this invention provides a combination of any of an analog, derivative, metabolite, isomer, prodrug, pharmaceutically acceptable salt, pharmaceutical product, polymorph, crystal, impurity, hydrate, and N-oxide of the compound of formulas I-XXV.

As contemplated herein, the present invention relates to the use of a SARM compound and/or its analog, derivative, isomer, metabolite, pharmaceutically acceptable salt, pharmaceutical product, hydrate, N-oxide, polymorph, crystal, impurity or combinations thereof. In one embodiment, the invention relates to the use of an analog of the SARM compound. In another embodiment, the invention relates to the use of a derivative of the SARM compound. In another embodiment, the invention relates to the use of an isomer of the SARM compound. In another embodiment, the invention relates to the use of a metabolite of the SARM compound. In another embodiment, the invention relates to the use of a pharmaceutically acceptable salt of the SARM compound. In another embodiment, the invention relates to the use of a pharmaceutical product of the SARM compound. In another embodiment, the invention relates to the use of a hydrate of the SARM compound. In another embodiment, the invention relates to the use of an N-oxide of the SARM compound. In another embodiment, the invention relates to the use of a polymorph of the SARM compound. In another embodiment, the invention relates to the use of a crystal of the SARM compound. In another embodiment, the invention relates to the use of an impurity of the SARM compound.

As defined herein, the term "isomer" includes, but is not limited to, optical isomers and analogs, structural isomers and analogs, conformational isomers and analogs, and the like. In one embodiment, the term "isomer" is meant to encompass optical isomers of the SARM compound. It will be appreciated by those skilled in the art that the SARMs of the present invention contain at least one chiral center. Accordingly, the SARMs used in the methods of the present invention may exist in, and be isolated in, optically-active or racemic forms. Some compounds may also exhibit polymorphism. It is to be understood that the present invention encompasses any racemic, optically-active, polymorphic, or stereoisomeric form, or mixtures thereof, which form possesses properties useful in the treatment of androgen-related conditions described herein. In one embodiment, the SARMs are the pure (R)-isomers. In another embodiment, the SARMs are the pure (S)-isomers. In another embodiment, the SARMs are a mixture of the (R) and the (S) isomers. In another embodiment, the SARMs are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

In one embodiment, this invention encompasses the use of various optical isomers of the SARM compound. It will be appreciated by those skilled in the art that the SARMs of the present invention contain at least one chiral center. Accordingly, the SARMs used in the methods of the present invention may exist in, and be isolated in, optically-active or racemic forms. Some compounds may also exhibit polymorphism. It is to be understood that the present invention encompasses any racemic, optically-active, polymorphic, or stereoisomeric form, or mixtures thereof, which form possesses properties useful in the treatment of androgen-related conditions described herein. In one embodiment, the SARMs are the pure (R)-isomers. In another embodiment, the SARMs are the pure (S)-isomers. In another embodiment, the SARMs are a mixture of the (R) and the (S) isomers. In another embodiment, the SARMs are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes "pharmaceutically acceptable salts" of the compounds of this invention, which may be produced, by reaction of a compound of this invention with an acid or base.

Suitable pharmaceutically-acceptable salts of amines of formulas I-XXV may be prepared from an inorganic acid or from an organic acid. In one embodiment, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrate, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

In one embodiment, examples of organic salts of amines may be selected from aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, carboxylates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates, gluconates, glutamates, glycolates, glucorates, glucoheptanoates, glycerophosphates, gluceptates, glycollylarsanilates, glutarates, glutamates, heptanoates, hexanoates, hydroxymaleates, hydroxycarboxlic acids, hexylresorcinates, hydroxybenzoates, hydroxynaphthoates, hydrofluorate, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, nitrates, naphthalenesulfonates, 2-naphthalenesulfonates, nicotinates, napsylates, N-methylglucamines, oxalates, octanoates, oleates, pamoates, phenylacetates, picrates, phenylbenzoates, pivalates, propionates, phthalates, phenylacetate, pectinates, phenylpropionates, palmitates, pantothenates, polygalacturates, pyruvates, quinates, salicylates, succinates, stearates, sulfanilate, subacetates, tartarates, theophyllineacetates, p-toluenesulfonates (tosylates), trifluoroacetates, terephthalates, tannates, teoclates, trihaloacetates, triethiodide, tricarboxylates, undecanoates and valerates.

In one embodiment, examples of inorganic salts of carboxylic acids or phenols may be selected from ammonium, alkali metals to include lithium, sodium, potassium, or cesium; alkaline earth metals to include calcium, magnesium, or aluminium; zinc, barium, cholines, or quaternary ammoniums.

In another embodiment, examples of organic salts of carboxylic acids or phenols may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolines, piperazines, procain, tris(hydroxymethyl)methylamines, triethylamines, triethanolamines, trimethylamines, tromethamines and ureas.

In one embodiment, the salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

In one embodiment, the invention also includes N-oxides of the amino substituents of the compounds described herein. Also, esters of the phenolic compounds can be made with aliphatic and aromatic carboxylic acids, for example, acetic acid and benzoic acid esters.

This invention provides derivatives of the SARM compounds. In one embodiment, "derivatives" includes but is not limited to ether derivatives, acid derivatives, amide derivatives, ester derivatives and the like. In another embodiment, this invention further includes hydrates of the SARM compounds.

In one embodiment, "hydrate" includes but is not limited to hemihydrate, monohydrate, dihydrate, trihydrate and the like.

This invention provides, in other embodiments, metabolites of the SARM compounds. In one embodiment, "metabolite" means any substance produced from another substance by metabolism or a metabolic process.

This invention provides, in other embodiments, pharmaceutical products of the SARM compounds. The term "pharmaceutical product" refers, in other embodiments, to a composition suitable for pharmaceutical use (pharmaceutical composition), for example, as described herein.

An "alkyl" group refers, in one embodiment, to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl. In one embodiment, the alkyl group is $CH_3$.

An "alkenyl" group refers, in another embodiment, to an unsaturated hydrocarbon, including straight chain, branched chain and cyclic groups having one or more double bond. The alkenyl group may have one double bond, two double bonds, three double bonds, etc. Examples of alkenyl groups are ethenyl, propenyl, butenyl, cyclohexenyl, etc. In one embodiment, the alkylene group has 1-12 carbons. In another embodiment, the alkylene group has 1-7 carbons. In another embodiment, the alkylene group has 1-6 carbons. In another embodiment, the alkylene group has 1-4 carbons. The alkenyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

A "haloalkyl" group refers to an alkyl group as defined above, which is substituted by one or more halogen atoms, in one embodiment by F, in another embodiment by Cl, in another embodiment by Br, in another embodiment by I.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like. In one embodiment, the aryl group is a 4-8 membered ring. In another embodiment, the aryl group is a 4-12 membered ring(s). In another embodiment, the aryl group is a 6 membered ring. In another embodiment, the aryl group is a 5 membered ring. In another embodiment, the aryl group is 2-4 fused ring system.

A "hydroxyl" group refers to an OH group. It is understood by a person skilled in the art that when T is OR, R is not OH.

In one embodiment, the term "halogen" refers to in one embodiment to F, in another embodiment to Cl, in another embodiment to Br, in another embodiment to I.

An "arylalkyl" group refers, in another embodiment, to an alkyl bound to an aryl, wherein alkyl and aryl are as defined above. An example of an arylalkyl group is a benzyl group.

In another embodiment, the present invention provides process for preparing a selective androgen receptor modulator (SARM) compound represented by the structure of formula III:

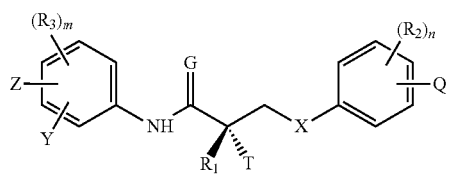

III wherein X is a bond, O, $CH_2$, NH, Se, PR, NO or NR;
G is O or S;
T is OH, OR, —$NHCOCH_3$, or NHCOR;
R is alkyl, haloalkyl, dihaloalkyl, trihaloalkyl, $CH_2F$, $CHF_2$, $CF_3$, $CF_2CF_3$, aryl, phenyl, halogen, alkenyl or OH;
$R_1$ is $CH_3$, $CH_2F$, $CHF_2$, $CF_3$, $CH_2CH_3$, or $CF_2CF_3$;
$R_2$ is H, F, Cl, Br, I, $CH_3$, $CF_3$, OH, CN, $NO_2$, $NHCOCH_3$, $NHCOCF_3$, NHCOR, alkyl, arylalkyl, OR, $NH_2$, NHR, $N(R)_2$, or SR;
$R_3$ is H, F, Cl, Br, I, CN, $NO_2$, COR, COOH, CONHR, $CF_3$, or $Sn(R)_3$; or
$R_3$ together with the benzene ring to which it is attached forms a fused ring system represented by the structure:

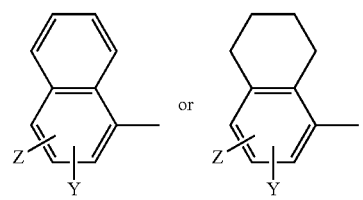

Z is $NO_2$, CN, Cl, F, Br, I, H, COR, COOH, or CONHR;
Y is $CF_3$, alkoxy, alkyl, hydroxyalkyl, alkylaldehyde, formyl, H, F, Br, Cl, I, CN, or $Sn(R)_3$;
Q is H, alkyl, halogen, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OH, OR, COR, OCOR, $OSO_2R$, $SO_2R$, or SR; or Q together with the benzene ring to which it is attached is a fused ring system represented by structure A, B or C:

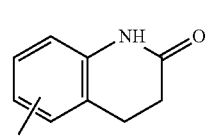

A

B

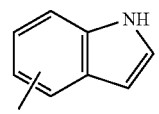

C n is an integer of 1-4; and
m is an integer of 1-3;
the process comprising the step of coupling a compound of formula (10):

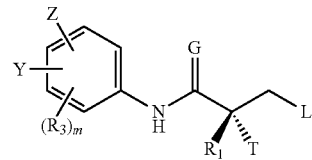

10 wherein Z, Y, G, $R_1$, T, $R_3$ and m are as defined above and L is a leaving group, with a compound of formula 11:

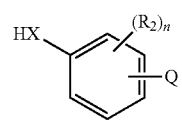

11 wherein Q, X, $R_2$ and n are as defined above.

In one embodiment, the coupling step is carried out in the presence of a base. In another embodiment, the leaving group L is Br.

In another embodiment, the compound of formula 10 is prepared by:
a) preparing a compound of formula 13 by ring opening of a cyclic compound of formula 12:

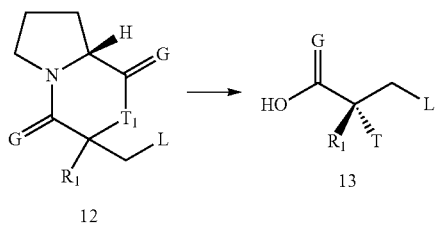

wherein L, $R_1$, G and T are as defined above, and $T_1$ is O or NH; and
b) reacting an amine of formula 14:

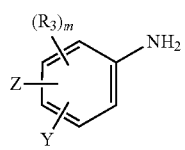

wherein Z, Y, $R_3$ and m are as defined above, with the compound of formula 13, in the presence of a coupling reagent, to produce the compound of formula 10.

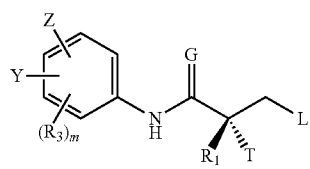

It is understood to a person skilled in the art that when $T_1$ is O or NH, T in compound 13 is O or $NH_2$. Thus, when T in compound 13 is OR, the reaction will involve a further step of converting the OH to OR by a reaction with, for example, an alkyl halide R—X. When T in compound 13 is NHCOR, $NHCOCH_3$, the reaction will involve a further step of converting the $NH_2$ to NHCOR or $NHCOCH_3$, by a reaction with, for example, the corresponding acyl chloride ClCOR or $ClCOCH_3$.

In one embodiment, step (a) is carried out in the presence of HBr.

In one embodiment, whereby compound 13 of step (a) is reacted with a coupling agent prior to step (b).

In one embodiment, the coupling step is carried out in the presence of a base. In another embodiment, the leaving group L is Br.

In another embodiment, the process further comprises the step of converting the selective androgen receptor modulator (SARM) compound to its analog, isomer, metabolite, derivative, pharmaceutically acceptable salt, pharmaceutical product, polymorph, crystal, impurity, N-oxide, hydrate or any combination thereof.

In another embodiment, this invention provides a large scale process for the preparation of compound of formula III, wherein the process comprises the same steps as described herein above, wherein compound of formula 12 is prepared according to the following scheme, in the presence of 4N NaOH:

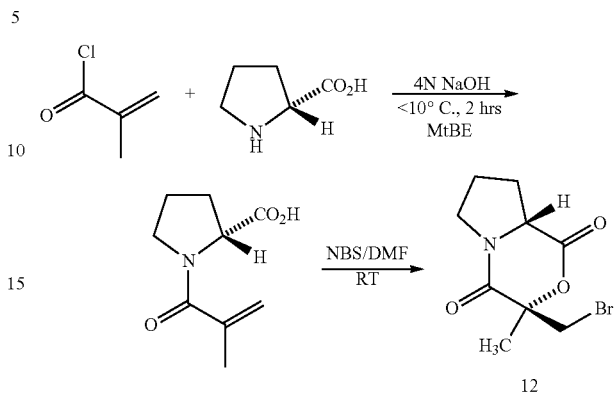

Figure 1B:
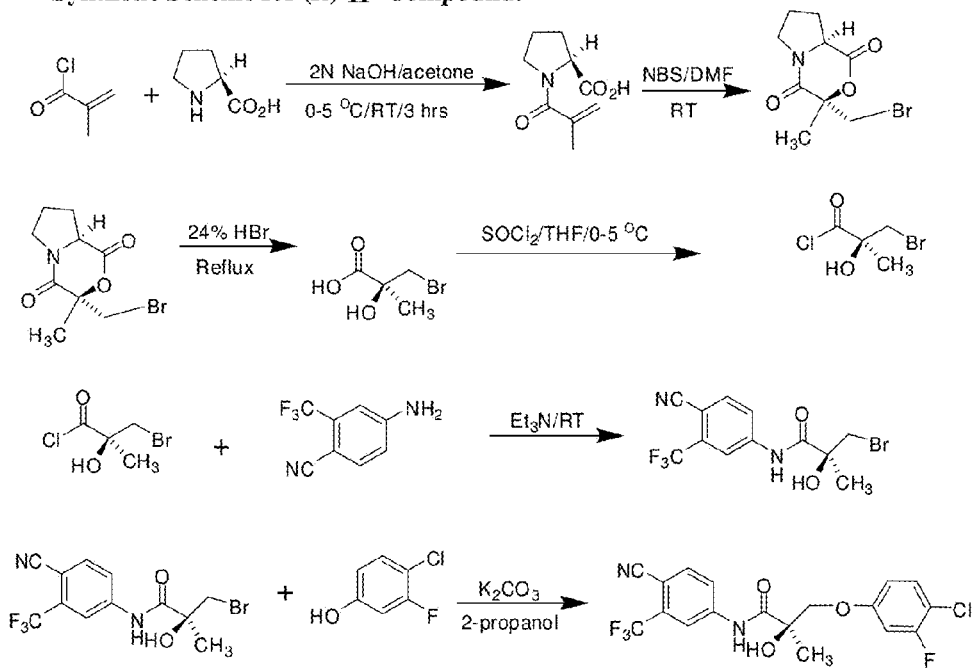
Figure 1C:
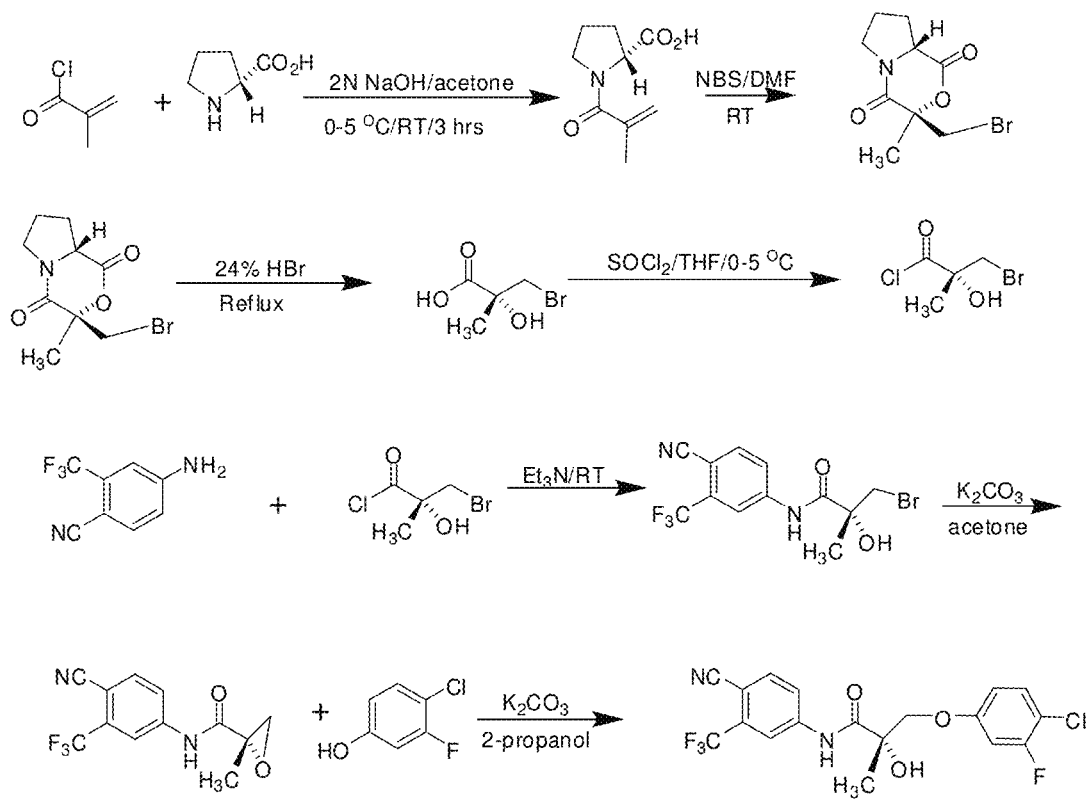
Figure 1D:
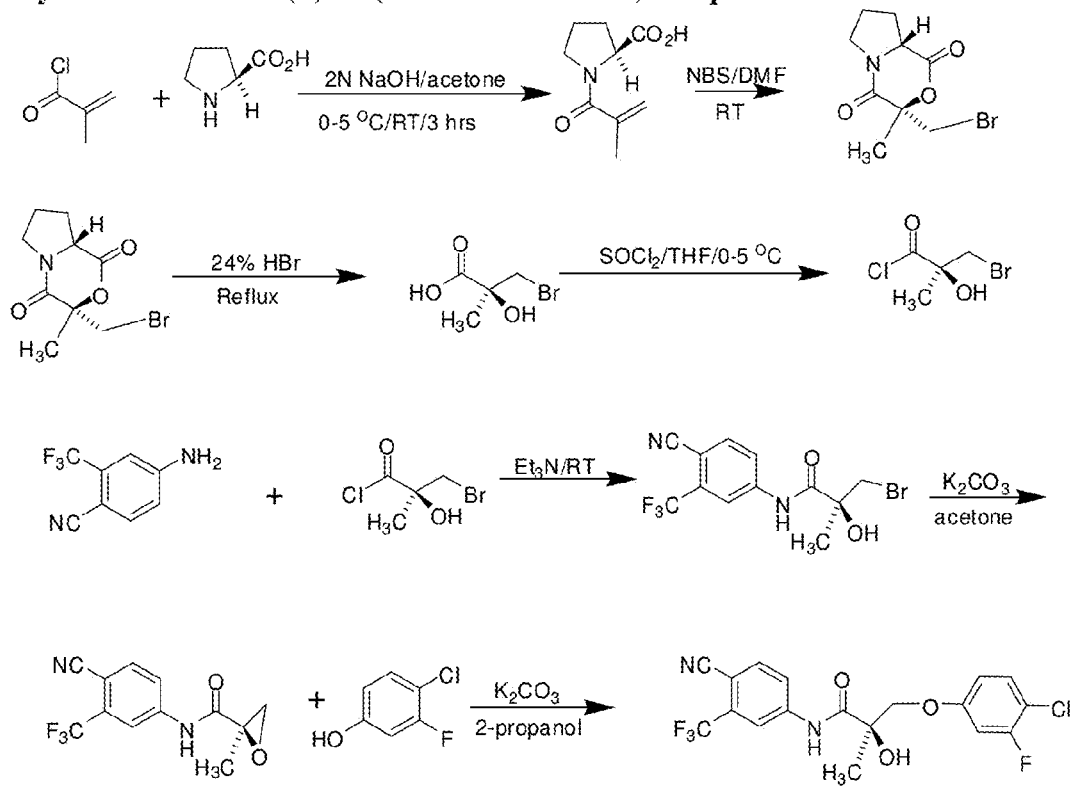
Figure 1E:
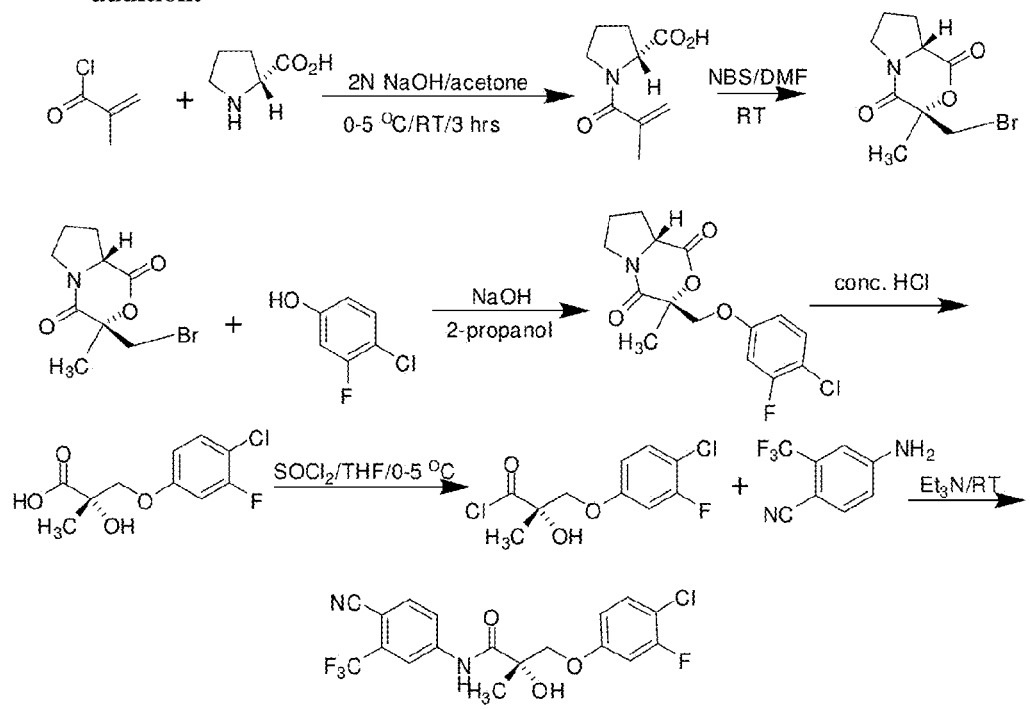
Figure 1F:
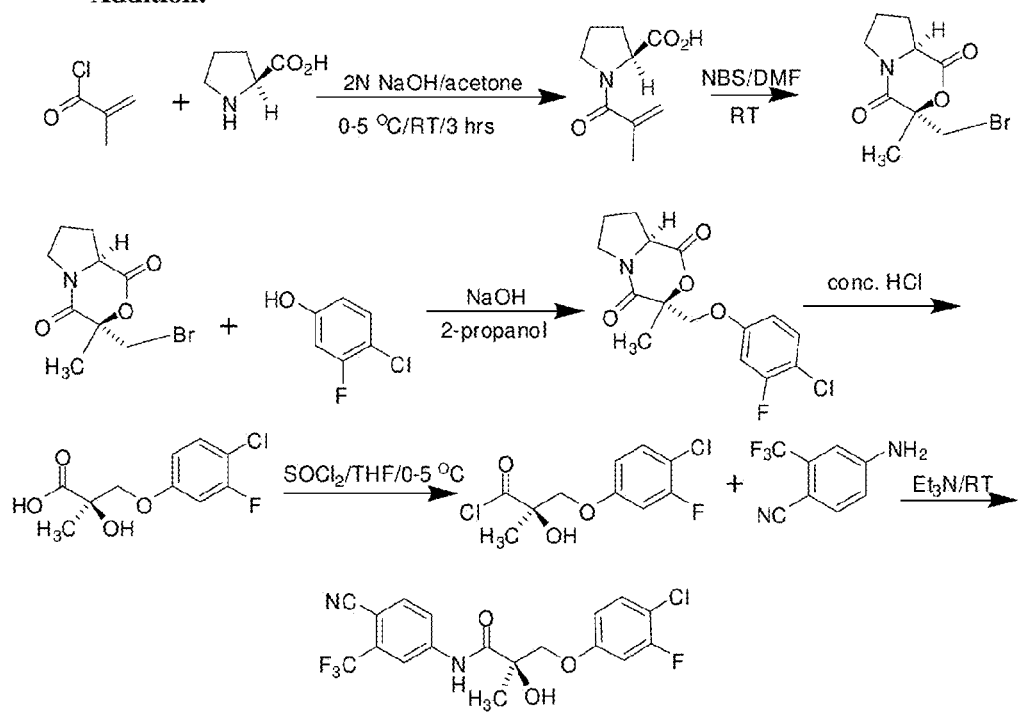
Figure 1G:
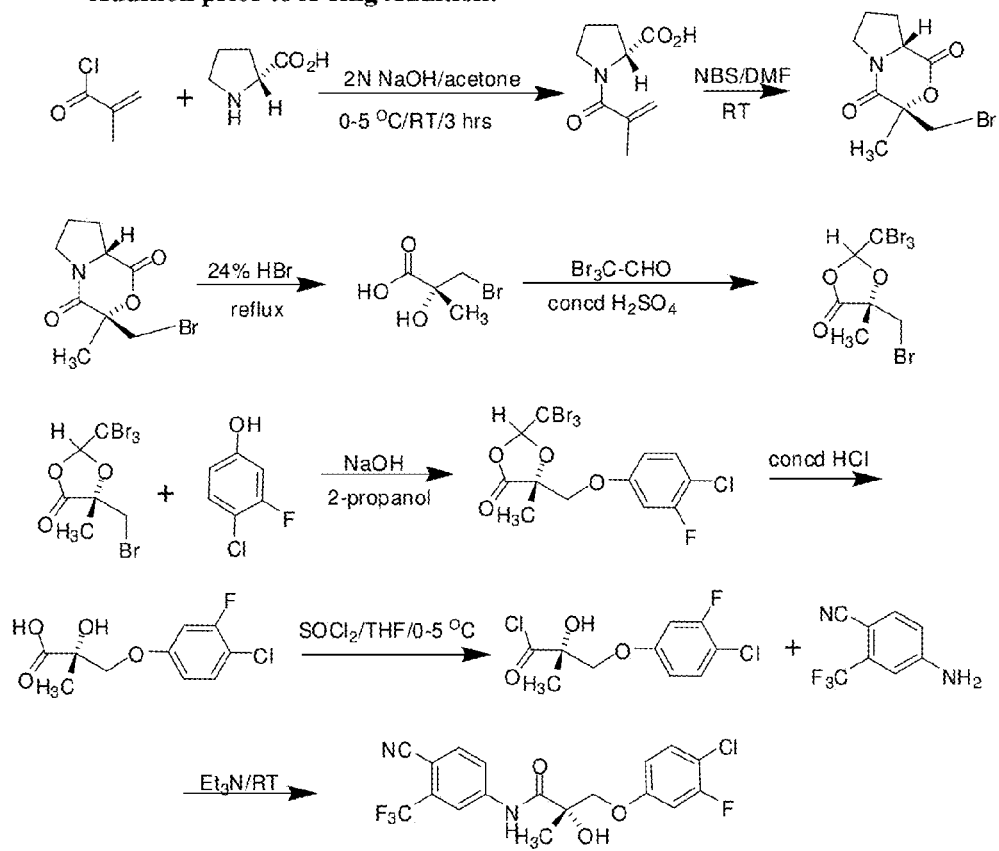
Figure 1H:
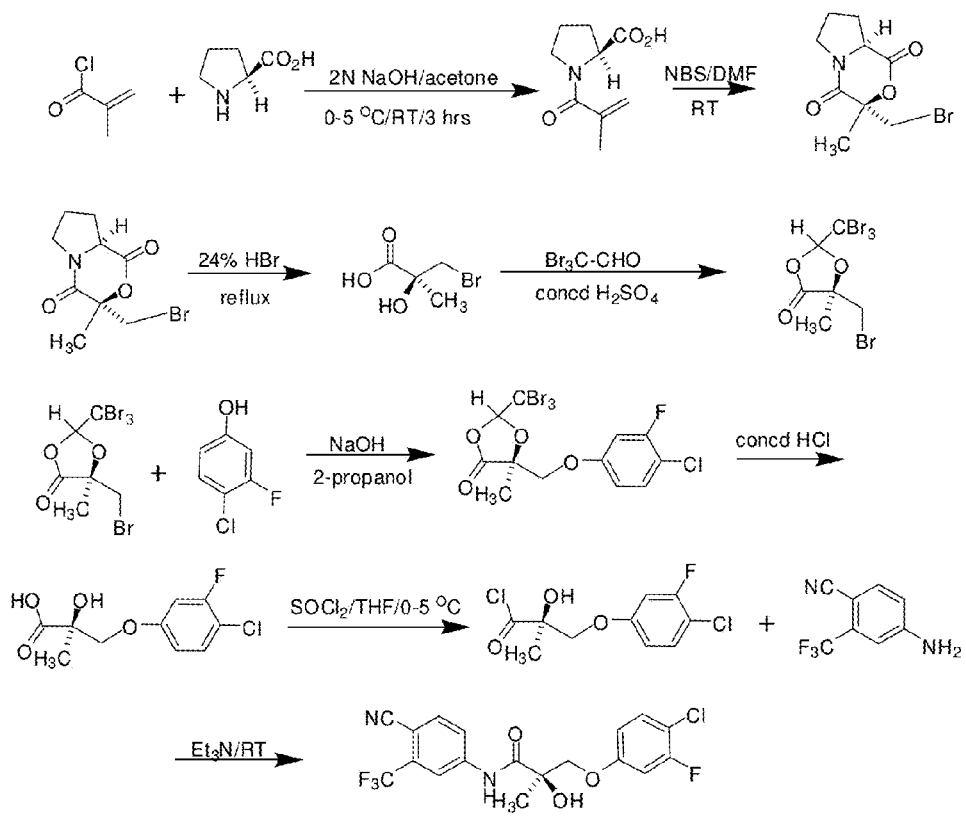
Figure 1I:
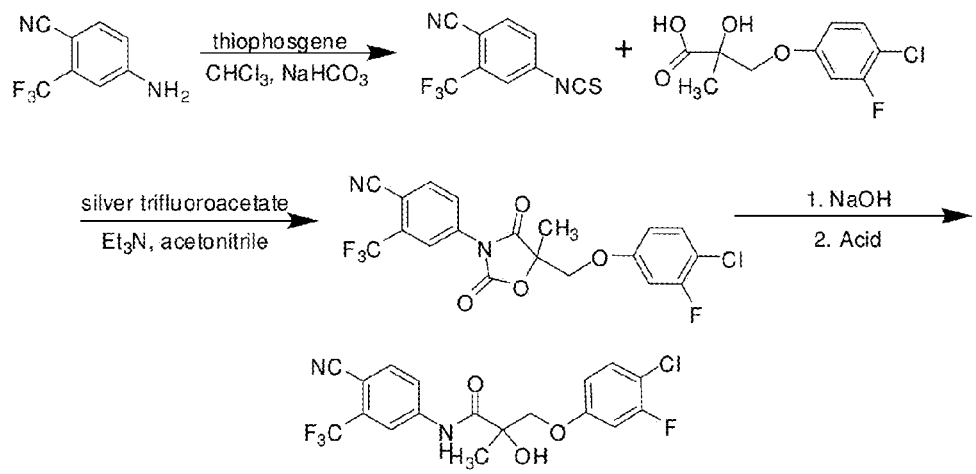
Figure 1J:
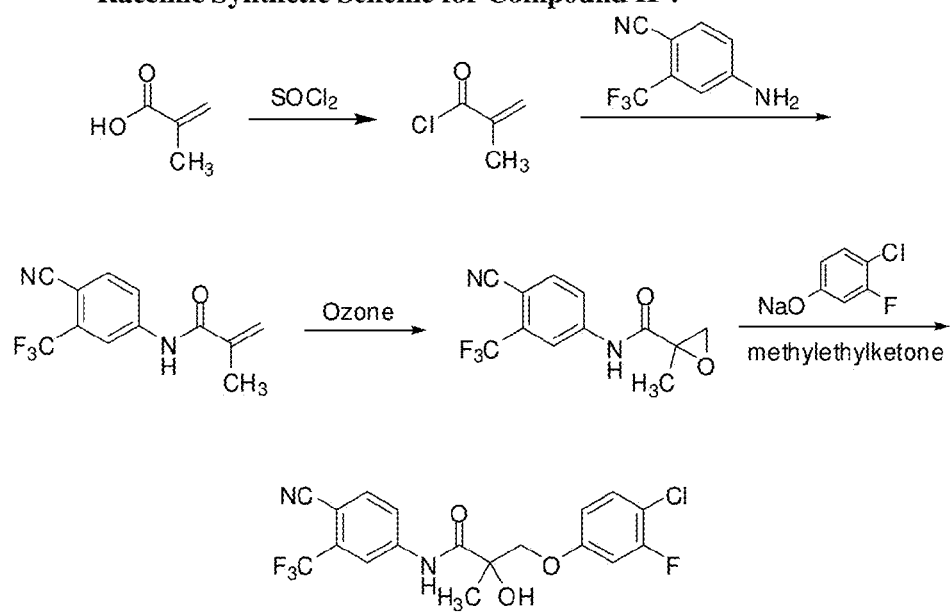
Figure 1K:
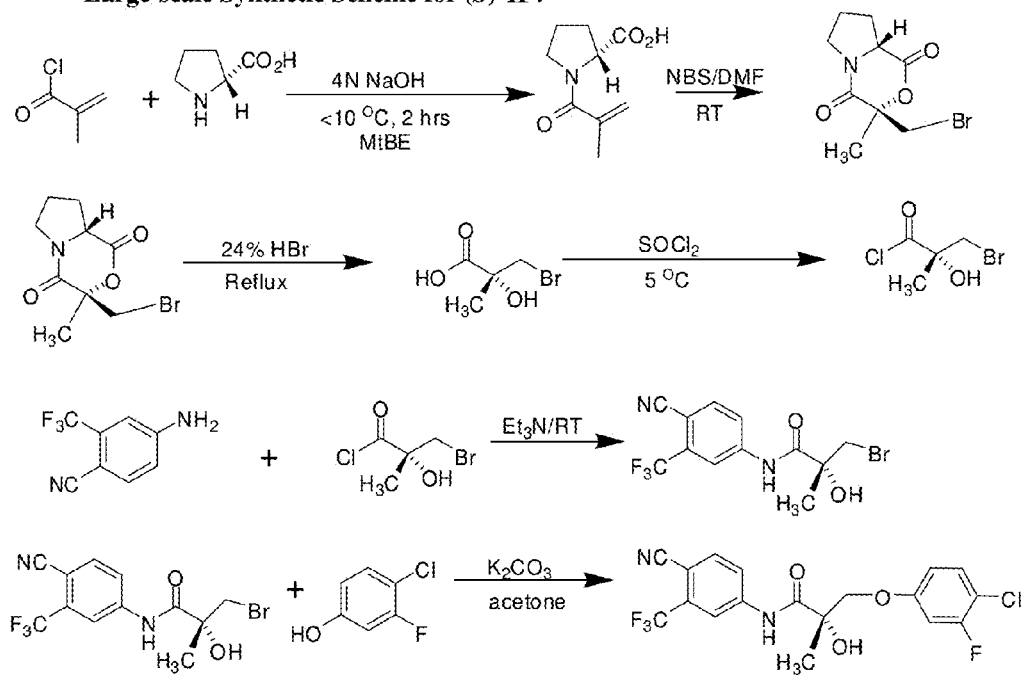
Figure 1L:
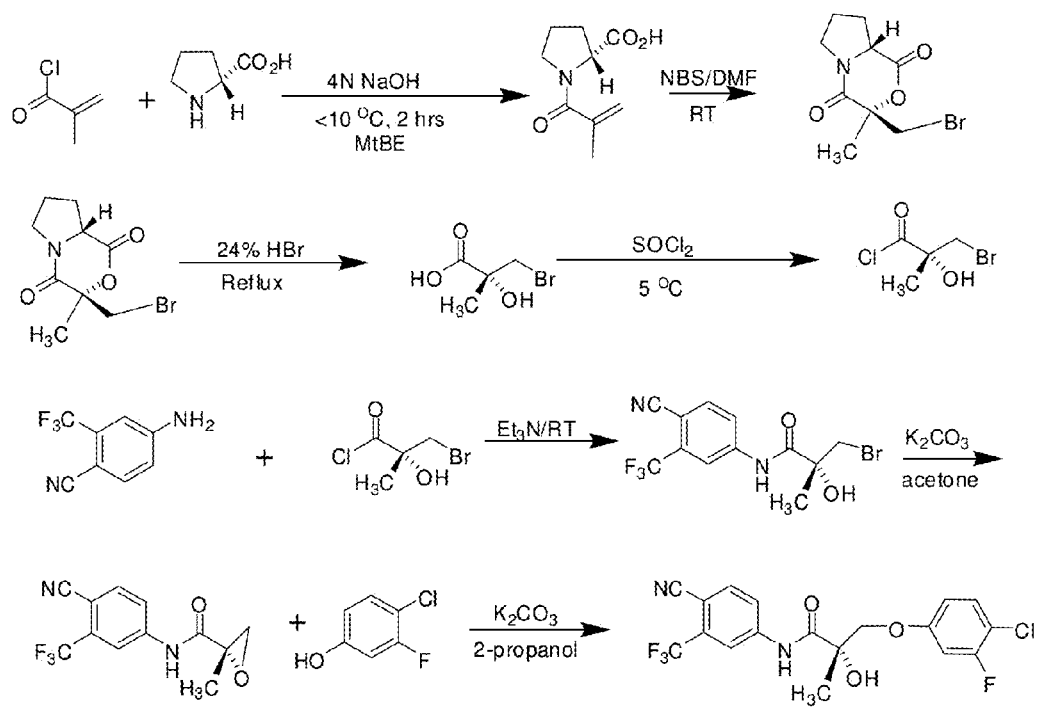

FIGS. 1K and 1L provide one embodiment of a large scale process for the preparation of a large scale synthesis of compounds of formulas S-II.

In one embodiment, the present invention provides a process for preparing a compound of formula III wherein is X is O. In another embodiment, the present invention provides a process for preparing a compound of formula III wherein T is OH. In another embodiment, the present invention provides a process for preparing a compound of formula III wherein is $R_1$ is $CH_3$. In another embodiment, the present invention provides a process for preparing a compound of formula III wherein Z is CN, Cl or F. In another embodiment, the present invention provides a process for preparing a compound of formula III, wherein Z is CN. In another embodiment, the present invention provides a process for preparing a compound of formula III wherein Y is $CF_3$, $CH_3$, or H or Cl. In another embodiment, the present invention provides a process for preparing a compound of formula III wherein $R_3$ is H, CN, or Cl and/or F. In another embodiment, the present invention provides a process for preparing a compound of formula III wherein Q is CN. In another embodiment, the present invention provides a process for preparing a compound of formula III wherein Q is F. In another embodiment, the present invention provides a process for preparing a compound of formula III wherein Q is Cl.

In another embodiment, the present invention provides a process for preparing a selective androgen modulator compound represented by the structure of formula II, as depicted in FIGS. 1A-1L and Example 1:

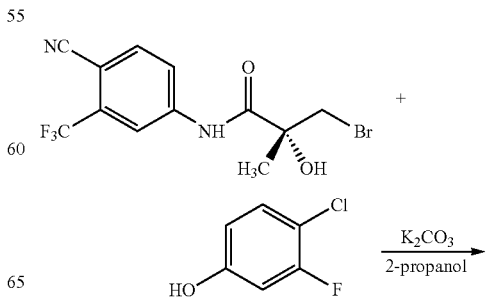

-continued

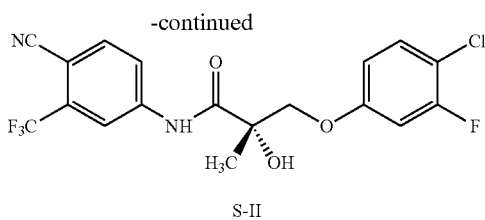

S-II

In another embodiment, the present invention provides a process for preparing an (S) enantiomer of SARM compound represented by the structure of formula S-II:

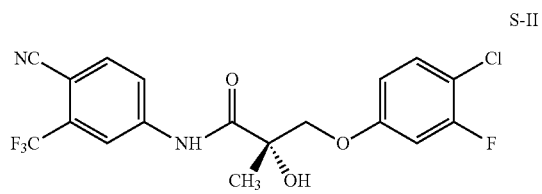

S-II said process comprising the steps of:
a) coupling an amine of formula 17:

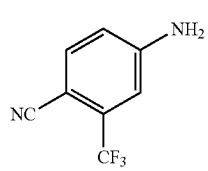

17 with the carboxylic acid of formula R-18

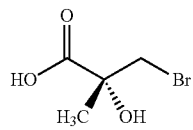

R-18 in the presence of a coupling reagent, to produce an amide of formula R-19

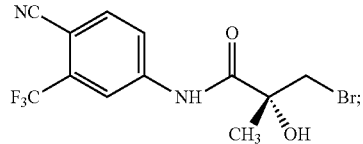

R-19 and
b) reacting the amide of formula R-19 with a compound of formula 20:

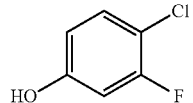

20 to produce a compound of formula S-II.

In one embodiment, whereby compound R-18 of step (a) is reacted with a coupling agent prior to addition of compound of formula 17.

FIG. 1A and Example 1 provide one embodiment of a process for the preparation of a compound of formula S-II.

In another embodiment, the conditions of step (b) of the process outlined hereinabove may comprise potassium carbonate, sodium carbonate, or cesium carbonate, or another base appropriate for this reaction, using 2-propanol, THF or methylethylketone as a solvent, optionally with a transition catalyst, BTBAC (benzyltributylammonium chloride) or other suitable agent.

In another embodiment, the present invention provides a process for preparing an (R) enantiomer of SARM compound represented by the structure of formula R-II:

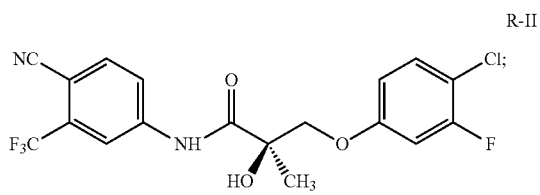 [SMILES: C[C@@](O)(COc1ccc(Cl)c(F)c1)C(=O)Nc1ccc(C#N)c(C(F)(F)F)c1]

R-II said process comprising the steps of:
a) coupling an amine of formula 17:

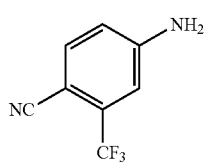

17 with the carboxylic acid of formula S-18

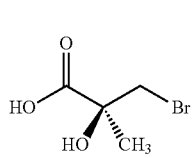

S-18 in the presence of a coupling reagent, to produce an amide of formula S-19

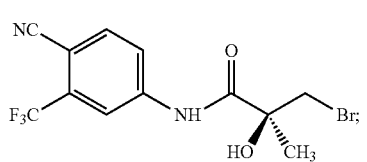

S-19 and
b) reacting the amide of formula S-19 with a compound of formula 20

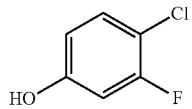

20 to produce a compound of R-II.

In one embodiment, whereby compound S-18 of step (a) is reacted with a coupling agent prior to addition of compound of formula 17.

FIG. 1B depicts one embodiment of such a process for the preparation of compound of formula R-II.

In another embodiment, the conditions of step (b) of the process outlined hereinabove may comprise potassium carbonate, sodium carbonate, or cesium carbonate, or another base appropriate for this reaction, using 2-propanol, THF or methylethylketone as a solvent, optionally with a transition catalyst, BTBAC (benzyltributylammonium chloride) or other suitable agent.

In another embodiment, the present invention provides a process for preparing an (S) enantiomer of a SARM compound represented by the structure of formula S-II

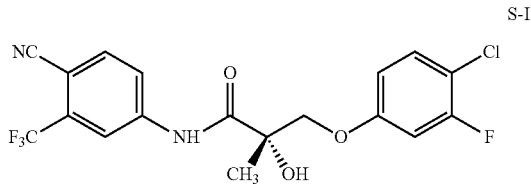

S-II said process comprising the steps of:
a) coupling an amine of formula 17:

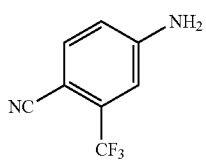

17 with the carboxylic acid of formula R-18

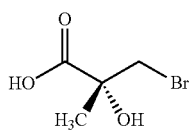

R-18 in the presence of a coupling reagent, to produce an amide of formula R-19

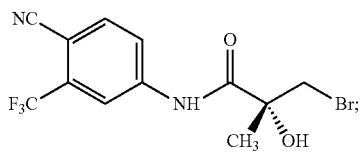

R-19 b) reacting the amide of formula R-19, with a base to form an oxirane S-21

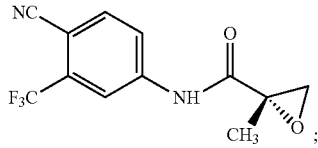

S-21 and
c) reacting the oxirane of formula S-21 with a compound of formula 20:

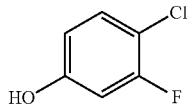

20 to produce a compound of S-II.

In one embodiment, whereby compound R-18 of step (a) is reacted with a coupling agent prior to addition of compound of formula 17.

FIG. 1C depicts an embodiment of such a process for the preparation of compound of formula S-II.

In another embodiment, the present invention provides a process for preparing an (R) enantiomer of SARM compound represented by the structure of formula R-II:

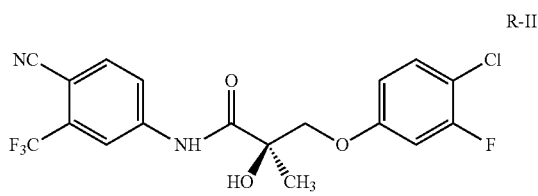 [SMILES: C[C@@](O)(COc1ccc(Cl)c(F)c1)C(=O)Nc1ccc(C#N)c(C(F)(F)F)c1]

R-II said process comprising the steps of:
a) coupling an amine of formula 17:

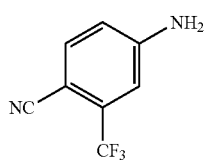

17 with the carboxylic acid of formula S-18

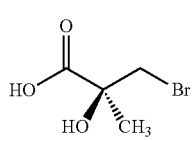

S-18 in the presence of a coupling reagent, to produce an amide of formula S-19

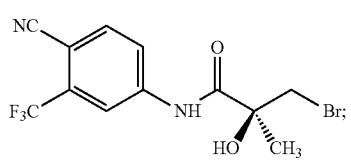

S-19 b) reacting the amide of formula S-19, with a base to form an oxirane R-21

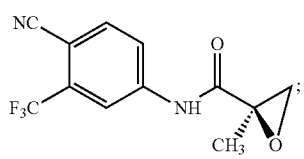

R-21 and
c) reacting the oxirane of formula R-21 with a compound of formula 20;

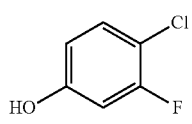

20 to produce a compound of R-II.

In one embodiment, whereby compound S-18 of step (a) is reacted with a coupling agent prior to addition of compound of formula 17.

FIG. 1D depicts preparation of compound of formula R-II.

In another embodiment, the present invention provides a process for preparing an (S) enantiomer of a SARM compound represented by the structure of formula S-II.

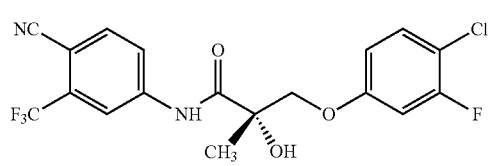

said process comprising the steps of:
a) reacting a ring of formula S-22

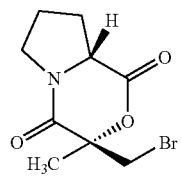

with a compound of 20

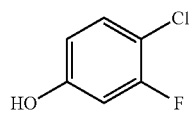

to produce a compound of formula R-23;

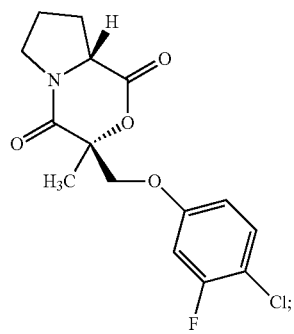

b) ring opening of compound of formula R-23 to produce a compound of formula S-24

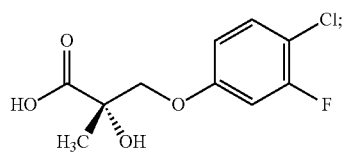

and
c) coupling the carboxylic acid of compound of formula S-24 with the amine of formula 17

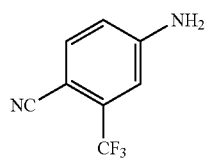

to produce the compound of formula S-II.

FIG. 1E depicts an embodiment of such a process for the preparation of compound of formula S-II.

In another embodiment, the present invention provides a process for preparing an (R) enantiomer of a SARM compound represented by the structure of formula R-II:

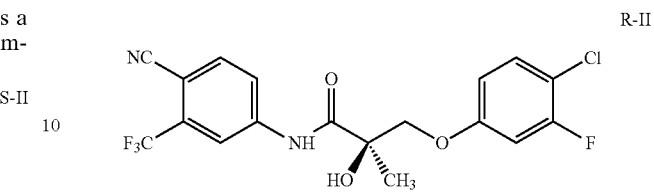

said process comprising the steps of:
a) reacting a ring of formula R-22

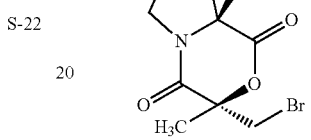

with a compound of 20

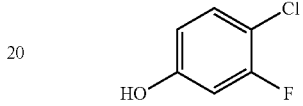

to produce a compound of formula S-23;

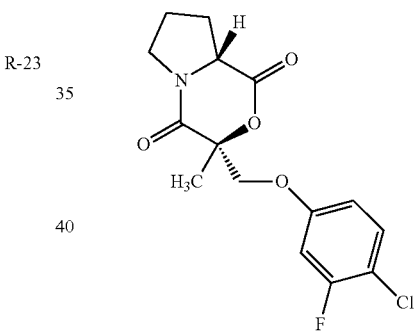

b) ring opening of compound of formula S-23 to produce a compound of formula R-24

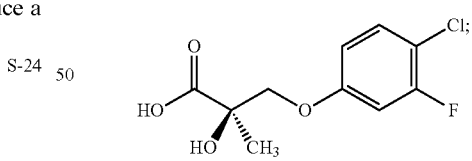

and
c) coupling the carboxylic acid of compound of formula R-24 with the amine of formula 17

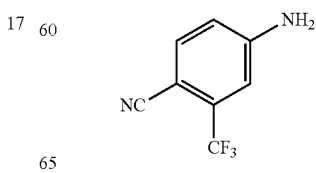

to produce the compound of formula R-II.

FIG. 1F depicts an embodiment of such a process for the preparation of compound of formula R-II.

In another embodiment, the present invention provides a process for preparing an (S) enantiomer of a SARM compound represented by the structure of formula S-II

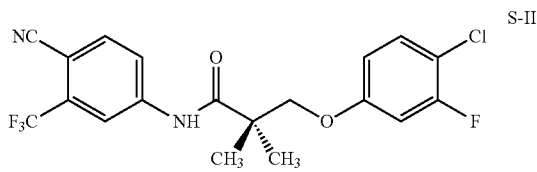

S-II said process comprising the steps of:

a) reacting the carboxylic acid of formula R-18

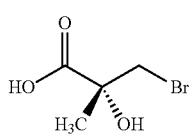

R-18 with tribromoacetaldehyde to produce a compound of formula R-25:

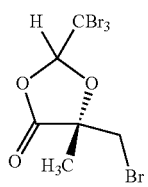

R-25 b) reacting the dioxalane derivative R-25 with a compound of formula 20

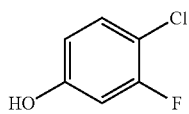

20 to produce a compound of formula R-26;

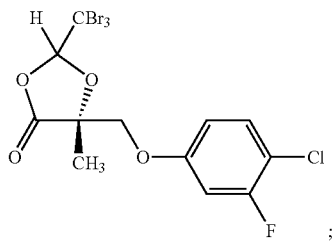

R-26 c) ring opening of compound of formula R-26 to produce a compound of formula S-24

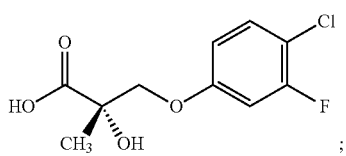

S-24 and d) coupling the carboxylic acid of compound of formula S-24 with the amine of formula 17:

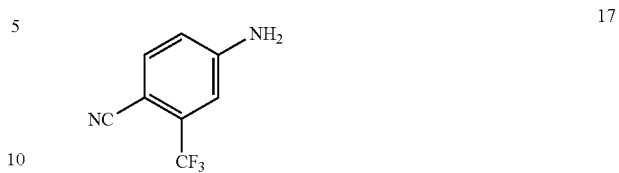

17 to produce the compound of formula S-II.

FIG. 1G depicts an embodiment of such a process for the preparation of compound of formula S-II.

In another embodiment, the present invention provides a process for preparing an (R) enantiomer of a SARM compound represented by the structure of formula R-II

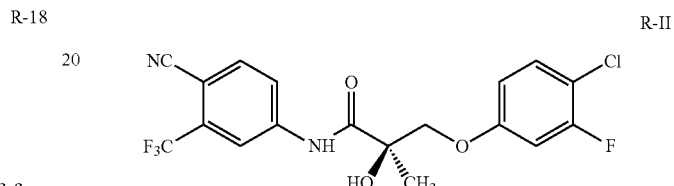

R-II said process comprising the steps of:

a) reacting the carboxylic acid of formula S-18

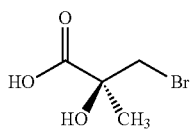

S-18 with tribromoacetaldehyde to produce a compound of formula S-25:

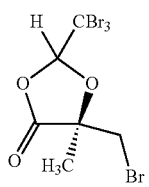

S-25 b) reacting the dioxalane derivative S-25 with a compound of formula 20

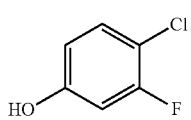

20 to produce a compound of formula S-26;

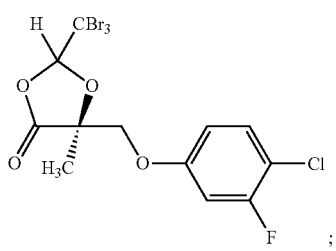

S-26 c) ring opening of compound of formula S-26 to produce a compound of formula R-24

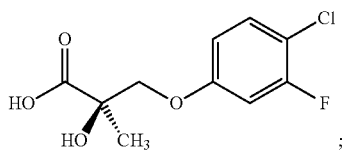

and d) coupling the carboxylic acid of compound of formula R-24 with the amine of formula 17:

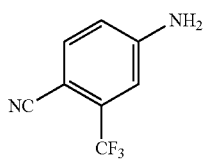

to produce the compound of formula R-II.

FIG. 1H depicts an embodiment of such a process for the preparation of compound of formula R-II.

In another embodiment, the present invention provides a process for preparing a racemic mixture of a SARM compound represented by the structure of formula II

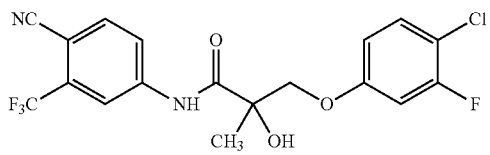

said process comprising the steps of:
a) reacting a compound of formula 24

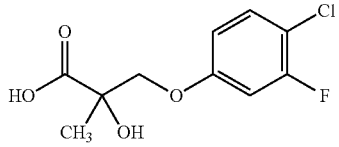

with a compound of formula 27

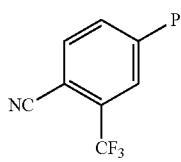

wherein P is selected from isocyanate (NCO) or isothiocyanate (NCS) to produce a compound of formula 28a or 28b, respectively

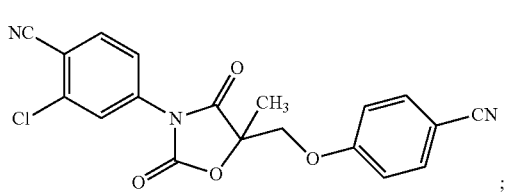

; or

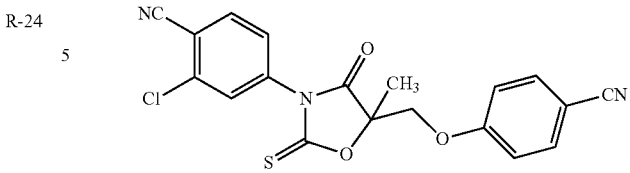

b) ring opening of the oxazolidinedione or 2-thioxooxazolid-4-one ring of formula 28a or 28b in a presence of a base to produce a compound of formula II.

FIG. 1I depicts an embodiment of such a process for the preparation of racemic compound of formula II.

In another embodiment, the present invention provides a process for preparing a racemic mixture of a SARM compound represented by the structure of formula II:

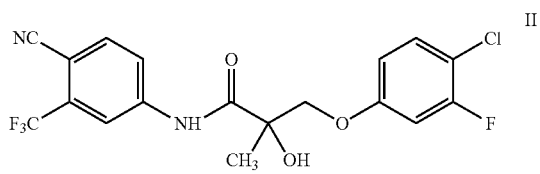 [SMILES: CC(O)(COc1ccc(Cl)c(F)c1)C(=O)Nc1ccc(C#N)c(C(F)(F)F)c1]

said process comprising the steps of:
a) chlorinating methacrylic acid:

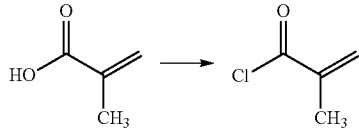

b) coupling an 3-cyano 4-trifluoromethyl aniline of formula 17 with methacryloyl chloride:

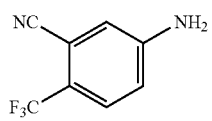

to produce the amide of formula 29,

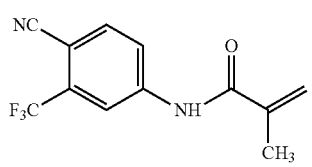

c) oxidizing an amide of formula 29, to produce the oxirane of formula 21:

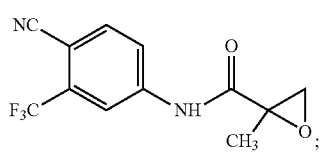

and d) reacting the oxirane of formula 21 with a compound of formula 20:

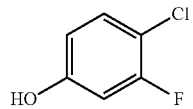
20 to produce the compound of formula II.

In another embodiment, the oxidizing an amide of formula 29 of step (c) comprises ozone. In another embodiment, the oxidizing agent is a peroxyacid, for example, peracetic acid, ($CH_3COOOH$). In another embodiment, the oxidizing agent meta-chloroperbenzoic acid (m-CPBA). In another embodiment, the oxidizing agent is magnesium monoperoxypthalic acid (MMPP). In another embodiment, the oxidizing agent is hydrogen peroxide together with catalytic amounts (1.0-0.1 mol %) of manganese($2^+$) salts.

FIG. 1J depicts an embodiment of a process for the preparation of racemic compound of formula II.

In one embodiment, this invention provides a process for preparing pure enantiomers of SARMs compounds of this invention, comprising the steps of: a) preparing a racemic SARM compound of this invention; and b) separating pure SARM compound of this invention from its racemic mixture.

In one embodiment, separation of the optically-active (R) isomer or (S) enantiomer, from the racemic SARM compounds of this invention comprises crystallization techniques. In another embodiment, the crystallization techniques include differential crystallization of enantiomers. In another embodiment, the crystallization techniques include differential crystallization of diastereomeric salts (tartaric salts or quinine salts). In another embodiment, the crystallization techniques include differential crystallization of chiral auxiliary derivatives (menthol esters, etc). In another embodiment, separation of the optically-active (R) isomer or (S) enantiomer, from the racemic SARM compounds of this invention comprises reacting the racemate mixture with another chiral group, forming of a diastereomeric mixture followed by separation of the diastereomers and removing the additional chiral group to obtain pure enantiomers. In another embodiment, separation of the optically-active (R) isomer or (S) enantiomer, from the racemic SARM compounds of this invention comprises chiral synthesis. In another embodiment, separation of the optically-active (R) isomer or (S) enantiomer, from the racemic SARM compounds of this invention comprises biological resolution. In another embodiment, separation of the optically-active (R) isomer or (S) enantiomer, from the racemic SARM compounds of this invention comprises enzymatic resolution. In another embodiment, separation of the optically-active (R) isomer or (S) enantiomer, from the racemic SARM compounds of this invention comprises chromatographic separation using a chiral stationary phase. In another embodiment, separation of the optically-active (R) isomer or (S) enantiomer, from the racemic SARM compounds of this invention comprises affinity chromatography. In another embodiment, separation of the optically-active (R) isomer or (S) enantiomer, from the racemic SARM compounds of this invention comprises capillary electrophoresis. In another embodiment, separation of the optically-active (R) isomer or (S) enantiomer, from the racemic SARM compounds of this invention comprises forming an ester group of the hydroxyl group of the chiral carbon with an optically-active acid, for example (−)-camphanic acid, separating the diastereomers esters, thus obtained, by fractional crystallization or preferably, by flash-chromatography, and then hydrolyzing each separate ester to the alcohol.

In another embodiment, the purity, and selectivity of an enantiomer obtained by the process of this invention, or by chiral separation of a racemic mixture of this invention can be determined by HPLC analysis.

In another embodiment, the process further comprises the step of converting the SARM compound to its analog, isomer, metabolite, derivative, pharmaceutically acceptable salt, pharmaceutical product, N-oxide, hydrate or any combination thereof.

According to this aspect of the invention, and in one embodiment, the reagent used for reacting the amide derivative, for example compound of formula 19 and the phenol derivative such as for example 20 are carried out in the presence of a base. Any suitable base that will deprotonate the hydrogen of the —XH moiety (for example, a phenol moiety when X is O) and allow the coupling may be used. Nonlimiting examples of bases are carbonates such as alkali carbonates, for example sodium carbonate ($Na_2CO_3$), potassium carbonate ($K_2CO_3$) and cesium carbonate ($Cs_2CO_3$); bicarbonates such as alkali metal bicarbonates, for example sodium bicarbonate ($NaHCO_3$), potassium bicarbonate ($KHCO_3$), alkali metal hydrides such as sodium hydride (NaH), potassium hydride (KH) and lithium hydride (LiH), and the like.

The leaving group L, according to this aspect, and in one embodiment, may comprise any removable group customarily considered for chemical reactions, as will be known to the person skilled in the art. Suitable leaving groups are halogens, for example F, Cl, Br and I; alkyl sulfonate esters (—$OSO_2R$) wherein R is an alkyl group, for example methanesulfonate (mesylate), trifluoromethanesulfonate, ethanesulfonate, 2,2,2-trifluoroethanesulfonate, perfluoro butanesulfonate; aryl sulfonate esters (—$OSO_2Ar$) wherein Ar is an aryl group, for example p-toluoylsulfonate (tosylate), benzenesulphonate which may be unsubstituted or substituted by methyl, chlorine, bromine, nitro and the like; $NO_3$, $NO_2$, or sulfate, sulfite, phosphate, phosphite, carboxylate, imino ester, $N_2$ or carbamate.

According to this aspect of the invention and in one embodiment, the reaction is carried out in a suitable inert solvent or diluent such as, for example, tetrahydrofuran, diethyl ether, acetone, methyl ethyl ketone, 2-propanol, aromatic amines such as pyridine; aliphatic and aromatic hydrocarbons such as benzene, toluene, and xylene; dimethylsulfoxide (DMSO), dimethylformamide (DMF), and dimethylacetamide (DMAC). In one embodiment, the reaction may be carried out in a suitable inert solvent or diluent as described hereinabove, suitably in the presence of a base such as triethylamine, and at a temperature in the range, as described above. In one embodiment, the reaction may be carried out at an appropriate temperature, as will be known to one skilled in the art, for example, in the range, of −20 to 120° C., or for example at or near ambient temperature.

The coupling reagent defined hereinabove is a reagent capable of turning the carboxylic acid/thiocarboxylic acid of formula 24 or 18 into a reactive derivative thereof, thus enabling coupling with the respective amine to form an amide/thioamide bond. A suitable reactive derivative of a carboxylic acid/thiocarboxylic acid is, for example, an acyl halide/thioacyl halide, for example an acyl/thioacyl chloride formed by the reaction of the acid/thioacid and an inorganic acid chloride, for example thionyl chloride; a mixed anhydride, for example an anhydride formed by the reaction of the acid and a chloroformate such as isobutyl chloroformate; an active ester/thioester, for example an ester formed by the reaction of the acid and a phenol such as pentafluorophenol, an ester such as pentafluorophenyl trifluoroacetate or an alcohol such as methanol, ethanol, isopropanol, butanol or N-hydroxybenzotriazole; an acyl/thioacyl azide, for example an azide formed by the reaction of the acid/thioacid and azide such as diphenylphosphoryl azide; an acyl cyanide/thioacyl cyanide, for example a cyanide formed by the reaction of an acid and a cyanide such as diethylphosphoryl cyanide; or the product of the reaction of the acid/thioacid and a carbodiimide such as dicyclohexylcarbodiimide.

It is to be understood that the process may comprise any embodiment described herein, as will be appropriate to produce a SARM of a corresponding formula, as will be appreciated by one skilled in the art.

In one embodiment, the process for preparing a SARM of this invention may involve ring opening in the presence of less acidic conditions, which in another embodiment, diminish the likelihood of obtaining SARM compound mixtures, and provide higher yield and purity of a SARM of interest. In one embodiment, the ring opening of a process as described herein, to produce a carboxylic acid of formula 13, is carried out in the presence of HBr, which, in one embodiment, is at a concentration of up to 30%, or in another embodiment, of up to 40%, or in another embodiment, is of up to 25%, or in another embodiment, of up to 23%, or in another embodiment, of up to between 20-25%. In one embodiment, the SARMs of this invention may be produced via large-scale synthesis, providing highly pure products in high yields.

In one embodiment, the reaction may be carried out in a suitable inert solvent or diluent as described hereinabove, suitably in the presence of a base such as triethylamine, and at a temperature in the range, as described above.

In some embodiments the compounds for use in the methods of this invention are nonsteroidal ligands for the androgen receptor and may demonstrate tissue-selective androgenic and/or anabolic activity. These novel agents are useful in affecting the carcass composition, increasing the lean mass and/or reducing the fat mass of an animal, reducing percent fat mass, increasing feed efficiency, increasing average daily gain (ADG), decreasing feed to gain ratio (F:G), increasing muscle growth, modulation of meat quality, and/or enhancing productive life of animals, including feedlot animals, beef cattle and finishing livestock. These novel agents are useful in males for the treatment of a variety of hormone-related conditions such as sexual dysfunction, decreased sexual libido, erectile dysfunction, hypogonadism, sarcopenia, osteopenia, osteoporosis, alterations in cognition and mood, depression, anemia, hair loss, obesity, benign prostate hyperplasia and/or prostate cancer. Further, the compounds are useful as adjunct to androgen-deprivation therapy (ADT) for treating prostate cancer. Further, the compounds are useful for oral testosterone replacement therapy, and treating prostate cancer. In other embodiments, the compounds are useful for the treatment of a variety of hormone-related conditions in females including, sexual dysfunction, decreased sexual libido, hypogonadism, sarcopenia, osteopenia, osteoporosis, alterations in cognition and mood, depression, anemia, hair loss, obesity, endometriosis, infertility, breast cancer, uterine cancer and ovarian cancer. In other embodiments, the SARMs are useful for treating, suppressing, inhibiting or reducing the incidence of diabetes type II, diabetes type I, glucose intolerance, hyperinsulinemia, insulin resistance, dyslipidemia, hypercholesterolemia, high blood pressure, obesity, fatty liver conditions, diabetic nephropathy, diabetic neuropathy, diabetic retinopathy, cardiovascular disease, atherosclerosis, cerebrovascular conditions and stroke.

In some embodiments, the compounds as described herein are useful in preventing and treating muscle wasting disorders, bone related disorders, and diabetes related disorders.

In some embodiments, the compounds as described herein are useful, either alone or as a combination with beta-agonists as feed composition, pharmaceutical compositions or as methods for affecting the carcass composition, increasing the lean mass, reducing the fat mass and/or reducing the percent fat mass, increasing feed efficiency, increasing average daily gain (ADG), decreasing feed to gain ratio (F:G) of an animal. In some embodiment, the compounds as described herein are useful, either alone or as a combination with beta-agonists as feed composition or as methods for increasing the muscle growth of an animal, decreasing time to market (or time to slaughter), increasing carcass weight (or slaughter weight) of a feedlot or finishing animal, modulation of meat quality, enhancing productive life of and/or improving herd health of animals, including feedlot animals, beef cattle and finishing livestock.

In some embodiments, the compounds as described herein are useful, either alone or as a composition, in males and females for the treatment of a variety of hormone-related conditions, such as hypogonadism, sarcopenia, erectile dysfunction, lack of libido, osteoporosis and fertility. In some embodiments, the compounds as described herein are useful in stimulating or promoting or restoring function to various processes, which in turn result in the treatment of the conditions as herein described, including, inter alia, promoting erythropoiesis, osteogenesis, muscle growth, glucose uptake, or insulin secretion; and/or preventing lipidogenesis, clotting, insulin resistance, atherosclerosis, osteoclast activity, and others.

In one embodiment, the methods of this invention make use of the described compound contacting or binding a receptor, and thereby mediating the described effects. In some embodiments, the receptor is a nuclear receptor, which in one embodiment, is an androgen receptor, or in another embodiment, is an estrogen receptor, or in another embodiment, is a progesterone receptor, or in another embodiment, is a glucocorticoid receptor. In some embodiments, the multitude of effects may occur simultaneously, as a function of binding to multiple receptors in the subject. In some embodiments, the tissue selective effects of the compounds as described herein provide for simultaneous action on different target organs.

Compositions and Methods of Use

In some embodiments, this invention provides methods of use which comprise administering a composition comprising the described compounds. In one embodiment, a composition is a pharmaceutical composition. In one embodiment, a composition is a feed composition. In one embodiment, feed composition may be a pharmaceutical composition.

As used herein, "pharmaceutical composition" means a "therapeutically effective amount" of the active ingredient, i.e. the compound of formula III, together with a pharmaceutically acceptable carrier or diluent. A "feed composition" means an "effective amount". A "therapeutically effective amount" and/or an "effective amount" as used herein, refers to that amount which provides a therapeutic effect or effect on the carcass of the animal for a given condition and administration regimen.

In one embodiment, the present invention encompasses incorporating the compounds into animal feed. In one embodiment, the present invention encompasses incorporating the compounds into a feed composition. In some embodiments, the compounds/compositions of this invention may be administered to any animal as herein described, for example to finishing livestock. Such administration, in some embodiments, is accomplished via, inter alia, supplementation in feeds, feed compositions, formulation into feeds, controlled release implants, topical sprays or creams/ ointments, dissolution in drinking water, rumen-stable formulations to include coatings and derivatives, repeated injection, and other means as will be known to the skilled artisan. In one embodiment, the present invention encompasses incorporating the compounds into other typical pharmaceutical administration routes and pharmaceutical compositions as described herein.

As used herein, the term "administering" refers to bringing a subject in contact with a compound of the present invention. As used herein, administration can be accomplished in vitro, i.e. in a test tube, or in vivo, i.e. in cells or tissues of living organisms, for example humans and/or animals. In one embodiment, the present invention encompasses administering the compounds of the present invention to a subject.

In one embodiment, the present invention encompasses administering the compounds of the present invention via implants. In one embodiment, administering the compounds of the present invention is via controlled release implants. In another embodiment of the present invention, administering the compounds of the present invention is via topical administration. In one embodiment, topical administration is via a topical spray. In one embodiment, topical administration is via a cream. In one embodiment, topical administration is via an ointment. In one embodiment, compounds and/or compositions of this invention are administered via an implant to a pig. In one embodiment, compounds and/or compositions of this invention are administered via topical administration to a pig.

In one embodiment, this invention is directed to a feed composition for an animal comprising a compound of this invention. In one embodiment, this invention is directed to a feed composition for an animal comprising a compound of formula IIIA or its isomer, pharmaceutically acceptable salt, crystal, N-oxide, hydrate or any combination thereof. In one embodiment, this invention is directed to a feed composition for an animal comprising a compound of formula I or its isomer, pharmaceutically acceptable salt, crystal, N-oxide, hydrate or any combination thereof. In one embodiment this invention is directed to a feed composition for an animal comprising a compound of formula II or its isomer, pharmaceutically acceptable salt, crystal, N-oxide, hydrate or any combination thereof. In one embodiment this invention is directed to a feed composition for an animal comprising a compound of formula XXIII or its isomer, pharmaceutically acceptable salt, crystal, N-oxide, hydrate or any combination thereof. In one embodiment this invention is directed to a feed composition for an animal comprising a compound of formula XXIV or its isomer, pharmaceutically acceptable salt, crystal, N-oxide, hydrate or any combination thereof. In one embodiment this invention is directed to a feed composition for an animal comprising a compound of formula XXV or its isomer, pharmaceutically acceptable salt, crystal, N-oxide, hydrate or any combination thereof.

The feed composition containing the compounds of this invention can be administered as additives to the animal feed. In one embodiment, the animal feed including the feed composition of this invention is provided to the animal once a day. In another embodiment twice a day. In another embodiment once to five times a day.

In another embodiment, the feed composition comprises between 0.010-50 ppm of a compound of this invention. In another embodiment, the feed composition comprises 0.01-1 ppm of a compound of this invention. In another embodiment, the feed composition comprises 0.10 ppm of a compound of this invention. In another embodiment, the feed composition comprises 1 ppm of a compound of this invention. In another embodiment, the feed composition comprises 3 ppm of a compound of this invention. In another embodiment, the feed composition comprises 10 ppm of a compound of this invention. In another embodiment, the feed composition comprises 30 ppm of a compound of this invention.

In one embodiment, the animal is fed with the feed composition of this invention after it has reached 60 pounds. In one embodiment, the animal is fed with the feed composition of this invention after it has reached 50 pounds. In one embodiment, the animal is fed with the feed composition of this invention before it has reached 50 pounds.

In one embodiment, the animal is fed with the feed composition of this invention for about ten weeks prior to slaughter. In one embodiment, the animal is fed with the feed composition of this invention for about twenty weeks prior to slaughter. In one embodiment, the animal is fed with the feed composition of this invention for about a year prior to slaughter.

In another embodiment, the feed composition of this invention comprises a combination of a compound of this invention and a beta-agonist. In another embodiment, the feed composition comprises a compound of formula II and a beta-agonist. In another embodiment, the feed composition comprises a compound of formula XXIII and a beta-agonist. In another embodiment, the feed composition comprises a compound of formula XXIV and a beta-agonist. In another embodiment, the feed composition comprises a compound of formula XXV and a beta-agonist.

In one embodiment, the animal is raised with a beta-agonist enhanced diet during a first time period of time and later fed in diet with substantially no beta-agonist, but including a compound of this invention during a second period of time.

In one embodiment a beta-agonist includes ractopamine hydrochloride (sold under the tradenames Optaflexx® or Paylean®, e.g. and available from Elanco of Greenfield, Ind.) and zilpaterol hydrochloride (sold under the tradename of Zilmax® available from Invervet of Millsboro, Del.). Other active isomers of other drugs with beta-adrenergic agonistic properties, include for example hexoprenaline, isoprenaline, riniterol, isoetharine, metaproterenol, reproterenol, cimaterol, procaterol, carbuterol, tulobuterol, pibuterol, mabuterol, bitolterol, clenbuterol, and bambuterol. Also included may be tautomers of beta-agonists that are under development, such as broxaterol, etanterol, imoxiterol, namiterol, picumeterol, RP 58802, RU 42173 and ZK 90055. Those skilled in the art will also realize that there are many pharmaceutically acceptable salt forms of these drugs, such as for example sulfate, fumarate, hydrobromide, dihydrochloride, methanesulphonate, hydroxynaphthoate, hydrochloride or where appropriate, one or other of the hydrate forms thereof.

In one embodiment, the feed composition of this invention is prepared as a dry powder or a granulate and added to the animal feed, such as by mixing. Also, other forms of the additive may also be appropriate. The additive can be pre-mixed into the feed according to any of the methods known to those skilled in the art, or may be mixed or blended into the feed at the time of feeding.

In one embodiment, this invention is directed to a pharmaceutical composition for an animal comprising a compound of this invention. In one embodiment, this invention is directed to a pharmaceutical composition for an animal comprising a compound of formula IIIA or its isomer, pharmaceutically acceptable salt, crystal, N-oxide, hydrate or any combination thereof. In one embodiment, this invention is directed to a pharmaceutical composition for an animal comprising a compound of formula I or its isomer, pharmaceutically acceptable salt, crystal, N-oxide, hydrate or any combination thereof. In one embodiment this invention is directed to a pharmaceutical composition for an animal comprising a compound of formula II or its isomer, pharmaceutically acceptable salt, crystal, N-oxide, hydrate or any combination thereof. In one embodiment this invention is directed to a pharmaceutical composition for an animal comprising a compound of formula XXIII or its isomer, pharmaceutically acceptable salt, crystal, N-oxide, hydrate or any combination thereof. In one embodiment this invention is directed to a pharmaceutical composition for an animal comprising a compound of formula XXIV or its isomer, pharmaceutically acceptable salt, crystal, N-oxide, hydrate or any combination thereof. In one embodiment this invention is directed to a pharmaceutical composition for an animal comprising a compound of formula XXV or its isomer, pharmaceutically acceptable salt, crystal, N-oxide, hydrate or any combination thereof.

The pharmaceutical composition containing the compounds of this invention can be administered as additives to the animal feed. In one embodiment, the animal feed including the pharmaceutical composition of this invention is provided to the animal once a day. In another embodiment twice a day. In another embodiment once to five times a day.

In another embodiment, the pharmaceutical composition comprises between 0.010-50 ppm of a compound of this invention. In another embodiment, the pharmaceutical composition comprises 0.01-1 ppm of a compound of this invention. In another embodiment, the pharmaceutical composition comprises 0.10 ppm of a compound of this invention. In another embodiment, the pharmaceutical composition comprises 1 ppm of a compound of this invention. In another embodiment, the pharmaceutical composition comprises 3 ppm of a compound of this invention. In another embodiment, the pharmaceutical composition comprises 10 ppm of a compound of this invention. In another embodiment, the pharmaceutical composition comprises 30 ppm of a compound of this invention.

In one embodiment, the pharmaceutical composition of this invention is in an amount from about 0.0005% to about 0.1% of the weight of the animal. In another embodiment, the pharmaceutical composition of this invention is in an amount from about 0.005% to about 0.01% of the weight of the animal. In another embodiment, the pharmaceutical composition of this invention is in an amount from about 0.01% to about 0.05%.

In one embodiment, the methods of this invention are used in a subject, which is a human. In another embodiment, the subject is a mammal. In another embodiment, the subject is an animal. In another embodiment the subject is an invertebrate. In another embodiment the subject is a vertebrate. In another embodiment, the animal is a feedlot animal. In another embodiment, the animal is a beef cattle. In another embodiment, the animal is a finishing livestock.

For administration to mammals, and particularly humans, it is expected that the physician will determine the actual dosage and duration of treatment, which will be most suitable for an individual and can vary with the age, weight and response of the particular individual.

For administration to mammals, in some embodiments, the present invention provides compounds, compositions and methods of use thereof for the enhanced meat productivity in food animals. In some embodiments, this invention provides compounds, compositions and methods of use thereof for the modulation of appetite for feedlot animals. In some embodiments, this invention provides compounds, compositions and methods of use thereof for improved feed efficiency.

For administration to mammals, in some embodiments, this invention provides compounds, compositions and methods of use thereof for decreased time to market for feedlot animals. In some embodiments, this invention provides compounds, compositions and methods of use thereof for increased terminal weight of feedlot animals. In some embodiments, this invention provides compounds, compositions and methods of use thereof for decreased time to terminal weight of feedlot animals. In some embodiments, this invention provides compounds, compositions and methods of use thereof for increased lean weight of feedlot animals. In some embodiments, this invention provides compounds, compositions and methods of use thereof for decreased body fat weight of feedlot animals. In some embodiments, this invention provides compounds, compositions and methods of use thereof for decreased percent body fat weight of feedlot animals. In some embodiments, this invention provides compounds, compositions and methods of use thereof for the modulation of meat quality in feedlot animals. In some embodiments, this invention provides compounds, compositions and methods of use thereof for increased meat production.

In some embodiments, the term "feedlot animals" refers to, inter alia, any animal the meat of which is considered edible in a given culture or country. In some embodiments, such term may include without limitation swine (domestic pig, wild boars), bovine (bison, cattle, yaks), cervids (deer, elk, moose), ovine (sheep/lamb), caprine (goats), lagomorphs (rabbit, pika), avian (chicken, turkey, duck, game birds, emu/ostrich), fish (catfish, tilapia, salmon, red drum), shellfish (crustaceans such as crab, lobster, shrimp; and mollusks such as clams, octopus, squid), roe (caviar), amphibians (frogs, salamanders), reptiles (snakes, turtle, alligator), canids (dog, fox), felines (cat), equines (horse, donkey, zebras), marsupials (kangaroo, opossum), insects (grasshopper, beetles, larvae), primates (gorilla, monkey), rodents (rat, mouse, squirrel, beaver), cetaceans (whale, dolphin), pinnipeds (walrus, seal), miscellaneous (bear, raccoon, elephant) or others as will be appreciated by one skilled in the art.

In some embodiments, the term "finishing livestock" refers to, inter alia, any animal that is normally fattened for the last few months before processing. In one embodiment, finishing livestock is a beef cattle. In one embodiment, finishing livestock is a pig. In one embodiment, finishing livestock is a poultry. In one embodiment, finishing livestock is a farmed fish.

In one embodiment, the compounds, compositions or methods of use thereof may find application in increasing the yield of all retail products derived from such feedlot animals. For instance, each of the above food animals have different types of tissues and preparations thereof such as for swine: ham, bacon, sausage, pork bellies, pork chop, ribs, brain, chitterling, tripe, tenderloin, etc.

Feedlot practices often include castration in order to better control the behavior of feedlot animals and to improve the quality of the meat (more tender, marbled, and colored). This occurs with a loss of productivity which could be offset using nonsteroidal androgens, representing one embodiment of a mechanism whereby the compounds and composition find application therein.

In some embodiments, enhancing measures of productivity in feedlot animals may comprise enhancing the number of animals per litter, litters per breeding animal per year, slaughter head count per breeding animal per year, meat product production (in pounds) per breeding animal per year, average daily growth in pounds, live weight (in pounds), dressing percent (% of live weight), dressed weight in pounds, retail meat in pounds per head count, retail meat yield (percent of live weight), or any combination thereof.

In one embodiment, the compounds, compositions or methods of use thereof may find application in stud farm productivity. Androgens (steroidal and nonsteroidal) are known to enhance sex drive in males and females such that, in some embodiments, the stud animals are productive in terms of "open" mating time or births per mating event. In some embodiments, the support of sex organs and accessory tissues (and health benefits) of the compounds/compositions of this invention may increase productive life of a stud animal, allowing him to "stand at stud" (i.e. meaning available for reproduction) for a longer period of time. Female receptivity is enhanced, in some embodiments, in terms of frequency, in response to contact with/administration of a compound/composition of this invention.

In some embodiments, this invention comprises application of any method as herein described for veterinary use, in any animal as described herein. In some embodiments, treatment of such conditions or diseases in animals may find application for pleasure and/or profit animals, may increase the size of game animals by supplementation, etc. as will be appreciated by one skilled in the art.

In some embodiments, the compounds/compositions may be administered to any animal as herein described, for example to livestock. Such administration, in some embodiments, is accomplished via, inter alia, supplementation in feeds, formulation into feeds, controlled release implants, dissolution in drinking water, rumen-stable formulations to include coatings and derivatives, repeated injection, and other means as will be known to the skilled artisan.

In some embodiments, dosages as described herein for humans will be adjusted to accommodate the varying size of animals. Such modification of dosage is well known in the field of veterinary art, and is available in common veterinary manuals, and may vary on a scale ranging from milligrams to grams as a function of such varying size.

In some embodiments, the compounds/compositions may be administered to any animal as herein described, in combination with any other agent as described herein, befitting the particular animal and condition in the animal, which is being treated. In some embodiments, such combination therapy may comprise administration of the compounds/compositions with high fat diets such as supplemented with fatty acids or oils to improve the meat quality; various combinations with androgens, progestins, anti-glucocorticoids, estrogens, growth hormone, etc. can be tailored to produce maximum weight gain performance in different types of animals (cows vs. pigs; intact vs. castrated) the specifics of which are known by those skilled in the art (see for example, Environ Qual Saf Suppl. 1976; (5):89-98).

In some embodiments, the compounds/compositions may be administered to any animal as herein described, which is a food source for humans, and in some embodiments, the tissue-selectivity and shorter half-lives of the compounds as herein described significantly lowers anticipated environmental effects. In some embodiments, the risk to human consumption thereby, as compared to agricultural use of steroidal androgens such as trenbolone acetate whose half-life is 3 days, is much reduced, and comprises therefore an embodiment of an advantage of the compounds of this invention.

In some embodiments, an advantage of the compounds/compositions of this invention may comprise the anabolic activity of the compound thereby producing larger animals and affecting carcass composition in less time. Factors contributing to the increasing productivity may include, in some embodiments, enhanced mineral (and other nutrient) absorption in the gut; enhanced body protein accretion and metabolism of fat stores resulting in increased lean growth rates; increasing nitrogen uptake by muscles, leading to an increase in the rate of protein synthesis and muscle/bone growth.

In some embodiments, the present invention provides a method for enhanced production such as milk, sperm, or egg. In some embodiments, the present invention provides a method for enhanced production of lean meats or eggs. In some embodiments, the present invention provides a method for increased productivity of feeds or stud livestock, for example, increased sperm count, improved morphology of sperm, etc. In some embodiments, the present invention provides a method for expanding the productive life of farm animals, for example, egg-laying hens, milk-producing cows, etc, and/or enhanced herd health, for example, improved immune clearance, stronger animals.

In one embodiment, this invention is directed to a method of affecting the carcass composition of an animal comprising administering a compound of this invention. In one embodiment, this invention is directed to a method of affecting the carcass composition of an animal comprising administering a compound of formula IIIA or its isomer, pharmaceutically acceptable salt, pharmaceutical product, crystal, N-oxide, hydrate or any combination thereof. In one embodiment, this invention is directed to a method of affecting the carcass composition of an animal comprising administering a compound of formula I or its isomer, pharmaceutically acceptable salt, pharmaceutical product, crystal, N-oxide, hydrate or any combination thereof. In one embodiment, this invention is directed to a method of affecting the carcass composition of an animal comprising administering a compound of formula II or its isomer, pharmaceutically acceptable salt, pharmaceutical product, crystal, N-oxide, hydrate or any combination thereof. In one embodiment, this invention is directed to a method of affecting the carcass composition of an animal comprising administering a compound of formula XXIII its isomer, pharmaceutically acceptable salt, pharmaceutical product, crystal, N-oxide, hydrate or any combination thereof. In one embodiment, this invention is directed to a method of affecting the carcass composition of an animal comprising administering a compound of formula XXIV or its isomer, pharmaceutically acceptable salt, pharmaceutical product, crystal, N-oxide, hydrate or any combination thereof. In one embodiment, this invention is directed to a method of affecting the carcass composition of an animal comprising administering a compound of formula XXV or its isomer, pharmaceutically acceptable salt, pharmaceutical product, crystal, N-oxide, hydrate or any combination thereof. In another embodiment, the carcass composition is affected by increasing the lean mass, reducing the fat mass, or reducing percent fat mass. In another embodiment, the carcass composition comprises increasing the growth performance in said animal.

In one embodiment, this invention is directed to a method of increasing lean mass of an animal comprising administering a compound of this invention. In one embodiment, this invention is directed to a method of increasing lean mass of an animal comprising administering a compound of formula IIIA or its isomer, pharmaceutically acceptable salt, pharmaceutical product, crystal, N-oxide, hydrate or any combination thereof. In one embodiment, this invention is directed to a method of increasing lean mass of an animal comprising administering a compound of formula I or its isomer, pharmaceutically acceptable salt, pharmaceutical product, crystal, N-oxide, hydrate or any combination thereof. In one embodiment, this invention is directed to a method of increasing lean mass of an animal comprising administering a compound of formula II or its isomer, pharmaceutically acceptable salt, pharmaceutical product, crystal, N-oxide, hydrate or any combination thereof. In one embodiment, this invention is directed to a method of increasing lean mass of an animal comprising administering a compound of formula XXIII its isomer, pharmaceutically acceptable salt, pharmaceutical product, crystal, N-oxide, hydrate or any combination thereof. In one embodiment, this invention is directed to a method of increasing lean mass of an animal comprising administering a compound of formula XXIV or its isomer, pharmaceutically acceptable salt, pharmaceutical product, crystal, N-oxide, hydrate or any combination thereof. In one embodiment, this invention is directed to a method of increasing lean mass of an animal comprising administering a compound of formula XXV or its isomer, pharmaceutically acceptable salt, pharmaceutical product, crystal, N-oxide, hydrate or any combination thereof.

In one embodiment, this invention is directed to a method of reducing fat mass of an animal comprising administering a compound of this invention. In one embodiment, this invention is directed to a method of reducing fat mass of an animal comprising administering a compound of formula IIIA or its isomer, pharmaceutically acceptable salt, pharmaceutical product, crystal, N-oxide, hydrate or any combination thereof. In one embodiment, this invention is directed to a method of reducing fat mass of an animal comprising administering a compound of formula I or its isomer, pharmaceutically acceptable salt, pharmaceutical product, crystal, N-oxide, hydrate or any combination thereof. In one embodiment, this invention is directed to a method of reducing fat mass of an animal comprising administering a compound of formula II or its isomer, pharmaceutically acceptable salt, pharmaceutical product, crystal, N-oxide, hydrate or any combination thereof. In one embodiment, this invention is directed to a method of reducing fat mass of an animal comprising administering a compound of formula XXIII its isomer, pharmaceutically acceptable salt, pharmaceutical product, crystal, N-oxide, hydrate or any combination thereof. In one embodiment, this invention is directed to a method of reducing fat mass of an animal comprising administering a compound of formula XXIV or its isomer, pharmaceutically acceptable salt, pharmaceutical product, crystal, N-oxide, hydrate or any combination thereof. In one embodiment, this invention is directed to a method of reducing fat mass of an animal comprising administering a compound of formula XXV or its isomer, pharmaceutically acceptable salt, pharmaceutical product, crystal, N-oxide, hydrate or any combination thereof.

In one embodiment, this invention is directed to a method of reducing percent fat mass of an animal comprising administering a compound of this invention. In one embodiment, this invention is directed to a method of reducing percent fat mass of an animal comprising administering a compound of formula IIIA or its isomer, pharmaceutically acceptable salt, pharmaceutical product, crystal, N-oxide, hydrate or any combination thereof. In one embodiment, this invention is directed to a method of reducing percent fat mass of an animal comprising administering a compound of formula I or its isomer, pharmaceutically acceptable salt, pharmaceutical product, crystal, N-oxide, hydrate or any combination thereof. In one embodiment, this invention is directed to a method of reducing percent fat mass of an animal comprising administering a compound of formula II or its isomer, pharmaceutically acceptable salt, pharmaceutical product, crystal, N-oxide, hydrate or any combination thereof. In one embodiment, this invention is directed to a method of reducing percent fat mass of an animal comprising administering a compound of formula XXIII its isomer, pharmaceutically acceptable salt, pharmaceutical product, crystal, N-oxide, hydrate or any combination thereof. In one embodiment, this invention is directed to a method of reducing percent fat mass of an animal comprising administering a compound of formula XXIV or its isomer, pharmaceutically acceptable salt, pharmaceutical product, crystal, N-oxide, hydrate or any combination thereof. In one embodiment, this invention is directed to a method of reducing percent fat mass of an animal comprising administering a compound of formula XXV or its isomer, pharmaceutically acceptable salt, pharmaceutical product, crystal, N-oxide, hydrate or any combination thereof.

In one embodiment, this invention is directed to a method of increasing feed efficiency of an animal comprising administering a compound of this invention. In one embodiment, this invention is directed to a method of increasing feed efficiency of an animal comprising administering a compound of formula IIIA or its isomer, pharmaceutically acceptable salt, pharmaceutical product, crystal, N-oxide, hydrate or any combination thereof. In one embodiment, this invention is directed to a method of increasing feed efficiency of an animal comprising administering a compound of formula I or its isomer, pharmaceutically acceptable salt, pharmaceutical product, crystal, N-oxide, hydrate or any combination thereof. In one embodiment, this invention is directed to a method of increasing feed efficiency of an animal comprising administering a compound of formula II or its isomer, pharmaceutically acceptable salt, pharmaceutical product, crystal, N-oxide, hydrate or any combination thereof. In one embodiment, this invention is directed to a method of increasing feed efficiency of an animal comprising administering a compound of formula XXIII its isomer, pharmaceutically acceptable salt, pharmaceutical product, crystal, N-oxide, hydrate or any combination thereof. In one embodiment, this invention is directed to a method of increasing feed efficiency of an animal comprising administering a compound of formula XXIV or its isomer, pharmaceutically acceptable salt, pharmaceutical product, crystal, N-oxide, hydrate or any combination thereof. In one embodiment, this invention is directed to a method of increasing feed efficiency of an animal comprising administering a compound of formula XXV or its isomer, pharmaceutically acceptable salt, pharmaceutical product, crystal, N-oxide, hydrate or any combination thereof.

In one embodiment, this invention is directed to a method of increasing average daily gain (ADG) of an animal comprising administering a compound of this invention. In one embodiment, this invention is directed to a method of increasing average daily gain (ADG) of an animal comprising administering a compound of formula IIIA or its isomer, pharmaceutically acceptable salt, pharmaceutical product, crystal, N-oxide, hydrate or any combination thereof. In one embodiment, this invention is directed to a method of increasing average daily gain (ADG) of an animal comprising administering a compound of formula I or its isomer, pharmaceutically acceptable salt, pharmaceutical product, crystal, N-oxide, hydrate or any combination thereof. In one embodiment, this invention is directed to a method of increasing average daily gain (ADG) of an animal comprising administering a compound of formula II or its isomer, pharmaceutically acceptable salt, pharmaceutical product, crystal, N-oxide, hydrate or any combination thereof. In one embodiment, this invention is directed to a method of increasing average daily gain (ADG) of an animal comprising administering a compound of formula XXIII its isomer, pharmaceutically acceptable salt, pharmaceutical product, crystal, N-oxide, hydrate or any combination thereof. In one embodiment, this invention is directed to a method of increasing average daily gain (ADG) of an animal comprising administering a compound of formula XXIV or its isomer, pharmaceutically acceptable salt, pharmaceutical product, crystal, N-oxide, hydrate or any combination thereof. In one embodiment, this invention is directed to a method of increasing average daily gain (ADG) of an animal comprising administering a compound of formula XXV or its isomer, pharmaceutically acceptable salt, pharmaceutical product, crystal, N-oxide, hydrate or any combination thereof.

In one embodiment, this invention is directed to a method of decreasing feed to gain ratio (F:G) of an animal comprising administering a compound of this invention. In one embodiment, this invention is directed to a method of decreasing feed to gain ratio (F:G) of an animal comprising administering a compound of formula IIIA or its isomer, pharmaceutically acceptable salt, pharmaceutical product, crystal, N-oxide, hydrate or any combination thereof. In one embodiment, this invention is directed to a method of decreasing feed to gain ratio (F:G) of an animal comprising administering a compound of formula I or its isomer, pharmaceutically acceptable salt, pharmaceutical product, crystal, N-oxide, hydrate or any combination thereof. In one embodiment, this invention is directed to a method of decreasing feed to gain ratio (F:G) of an animal comprising administering a compound of formula II or its isomer, pharmaceutically acceptable salt, pharmaceutical product, crystal, N-oxide, hydrate or any combination thereof. In one embodiment, this invention is directed to a method of decreasing feed to gain ratio (F:G) of an animal comprising administering a compound of formula XXIII its isomer, pharmaceutically acceptable salt, pharmaceutical product, crystal, N-oxide, hydrate or any combination thereof. In one embodiment, this invention is directed to a method of decreasing feed to gain ratio (F:G) of an animal comprising administering a compound of formula XXIV or its isomer, pharmaceutically acceptable salt, pharmaceutical product, crystal, N-oxide, hydrate or any combination thereof. In one embodiment, this invention is directed to a method of decreasing feed to gain ratio (F:G) of an animal comprising administering a compound of formula XXV or its isomer, pharmaceutically acceptable salt, pharmaceutical product, crystal, N-oxide, hydrate or any combination thereof.

In one embodiment the compounds, compositions and methods of this invention decrease the fat mass of an animal by 2-15%. In another embodiment, decrease the fat mass of an animal by 2-10%. In another embodiment, decrease the fat mass of an animal by 5-10%. In another embodiment, decrease the fat mass of an animal by 5-15%. In another embodiment, the animal is a pig. In another embodiment the animal is a beef cattle. In another embodiment, the animal is a finishing livestock. In another embodiment the animal is a feedlot animal.

In another embodiment the methods and/or compositions of this invention make use of the compounds of this invention for decreasing the fat mass of an animal by 5-15% after 7-28 days. In another embodiment the methods and/or compositions of this invention make use of the compounds of this invention for decreasing the fat mass of an animal by 5-15% after 7-14 days. In another embodiment the methods and/or compositions of this invention make use of the compounds of this invention for decreasing the fat mass of an animal by 5-15% after 14-21 days. In another embodiment the methods and/or compositions of this invention make use of the compounds of this invention for decreasing the fat mass of an animal by 5-15% after 21-28 days. In another embodiment the methods and/or compositions of this invention make use of the compounds of this invention for decreasing the fat mass of an animal by 5-15% after 28-60 days.

In one embodiment the compounds, compositions and methods of this invention increase lean mass of an animal by 5-15%. In another embodiment, increase lean mass of an animal by 5-10%. In another embodiment, increase lean mass of an animal by 8-10%. In another embodiment, increase lean mass of an animal by 15-30%. In another embodiment, the animal is a pig. In another embodiment the animal is beef cattle. In another embodiment, the animal is a finishing livestock. In another embodiment the animal is a feedlot animal.

In another embodiment the methods and/or compositions of this invention make use of the compounds of this invention for increasing lean mass of an animal by 5-15% after 7-28 days. In another embodiment the methods and/or compositions of this invention make use of the compounds of this invention for increasing lean mass of an animal by 5-15% after 7-14 days. In another embodiment the methods and/or compositions of this invention make use of the compounds of this invention for increasing lean mass of an animal by 5-15% after 14-21 days. In another embodiment the methods and/or compositions of this invention make use of the compounds of this invention for increasing lean mass of an animal by 5-15% after 21-28 days. In another embodiment the methods and/or compositions of this invention make use of the compounds of this invention for increasing lean mass of an animal by 5-15% after 28-60 days. In another embodiment the methods and/or compositions of this invention make use of the compounds of this invention for increasing lean mass of an animal by 15-30% after 7-28 days. In another embodiment the methods and/or compositions of this invention make use of the compounds of this invention for increasing lean mass of an animal by 15-30% after 7-14 days. In another embodiment the methods and/or compositions of this invention make use of the compounds of this invention for increasing lean mass of an animal by 15-30% after 14-21 days. In another embodiment the methods and/or compositions of this invention make use of the compounds of this invention for increasing lean mass of an animal by 15-30% after 21-28 days. In another embodiment the methods and/or compositions of this invention make use of the compounds of this invention for increasing lean mass of an animal by 15-30% after 28-60 days.

In one embodiment, the methods of this invention include administering a compound and/or feeding composition to an animal. In another embodiment, the compound and/or feed composition is provided in the daily feed to the animal. In another embodiment, the feed composition comprises a compound of this invention. In another embodiment, the feed composition comprises a combination of a compound of this invention and a beta-agonist. In another embodiment, the beta-agonist is ractopamine hydrochloride (Paylean®).

The pharmaceutical compositions and feed composition containing the compounds of this invention can be administered to a subject by any method known to a person skilled in the art, such as orally, parenterally, intravascularly, paracancerally, transmucosally, transdermally, intramuscularly, intranasally, intravenously, intradermally, subcutaneously, sublingually, intraperitoneally, intraventricularly, intracranially, intravaginally, by inhalation, rectally, intratumorally, or by any means in which the recombinant virus/composition can be delivered to tissue (e.g., needle or catheter). Alternatively, topical administration may be desired for application to mucosal cells, for skin or ocular application. Another method of administration is via aspiration or aerosol formulation.

In one embodiment, the pharmaceutical compositions are administered orally, and are thus formulated in a form suitable for oral administration, i.e. as a solid or a liquid preparation. Suitable solid oral formulations include tablets, capsules, pills, granules, pellets, powders, and the like. Suitable liquid oral formulations include solutions, suspensions, dispersions, emulsions, oils and the like. In one embodiment of the present invention, the SARM compounds are formulated in a capsule. In accordance with this embodiment, the compositions of the present invention comprise in addition to a compound of this invention and the inert carrier or diluent, a hard gelatin capsule.

In one embodiment, the micronized capsules comprise particles containing a compound of this invention, wherein the term "micronized" used herein refers to particles having a particle size is of less than 100 microns, or in another embodiment, less than 60 microns, or in another embodiment, less than 36 microns, or in another embodiment, less than 16 microns, or in another embodiment, less than 10 microns, or in another embodiment, less than 6 microns.

Further, in another embodiment, the pharmaceutical compositions are administered by intravenous, intraarterial, or intramuscular injection of a liquid preparation. Suitable liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intraarterially, and are thus formulated in a form suitable for intraarterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the compounds of this invention or their physiologically tolerated derivatives such as salts, esters, N-oxides, and the like are prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of a compound as herein described over a period of time. In a further embodiment, the pharmaceutical compositions are administered intravaginally.

In another embodiment, the active compound can be delivered in a vesicle, in particular a liposome (see Langer, Science 249:1627-1633 (1990); Treat et al., in Liposomes in the Therapy of Infectious Disease and Cancer, Lopez-Berestein and Fidler (eds.), Liss, New York, pp. 363-366 (1989); Lopez-Berestein, ibid., pp. 317-327; see generally ibid).

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In one embodiment, the compositions of this invention may include, a compound of this invention or any combination thereof, together with one or more pharmaceutically acceptable excipients.

It is to be understood that this invention encompasses any embodiment of a compound as described herein, which in some embodiments is referred to as "a compound of this invention". Such reference will include any compound, which is characterized by a structure of the formulas I-XXV, or any embodiment thereof, as described herein.

Suitable excipients and carriers may be, according to embodiments of the invention, solid or liquid and the type is generally chosen based on the type of administration being used. Liposomes may also be used to deliver the composition. Examples of suitable solid carriers include lactose, sucrose, gelatin and agar. Oral dosage forms may contain suitable binders, lubricants, diluents, disintegrating agents, coloring agents, flavoring agents, flow-inducing agents, and melting agents. Liquid dosage forms may contain, for example, suitable solvents, preservatives, emulsifying agents, suspending agents, diluents, sweeteners, thickeners, and melting agents. Parenteral and intravenous forms should also include minerals and other materials to make them compatible with the type of injection or delivery system chosen. Of course, other excipients may also be used.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, cyclodextrins, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's® dextrose, dextrose and sodium chloride, lactated Ringer's® and fixed oils. Intravenous vehicles include fluid and nutrient replenishers, electrolyte replenishers such as those based on Ringer's® dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween® 20, Tween® 80, Pluronic F68®, bile acid salts), protease inhibitors, surfactants (e.g. sodium lauryl sulfate), permeation enhancers, solubilizing agents (e.g., Cremophor®, glycerol, polyethylene glycerol, benzlkonium chloride, benzyl benzoate, cyclodextrins, sorbitan esters, stearic acids), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweetners (e.g. aspartame, citric acid), preservatives (e.g., Thimerosal®, benzyl alcohol, parabens), coloring agents, lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates), and/or adjuvants.

In one embodiment, the pharmaceutical compositions provided herein are controlled release compositions, i.e. compositions in which the compound of this invention is released over a period of time after administration. Controlled or sustained release compositions include formulation in lipophilic depots (e.g. fatty acids, waxes, oils). In another embodiment, the composition is an immediate release composition, i.e. a composition in which all of the compound is released immediately after administration.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:607 (1980); Saudek et al., N. Engl. J. Med. 321:674 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 116-138 (1984). Other controlled release systems are discussed in the review by Langer (Science 249:1627-1633 (1990).

The compositions may also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions which contain an active component is well understood in the art, for example by mixing, granulating, or tablet-forming processes. The active therapeutic ingredient is often mixed with excipients which are pharmaceutically acceptable and compatible with the active ingredient. For oral administration, the compounds of this invention or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the compounds of this invention or their physiologically tolerated derivatives such as salts, esters, N-oxides, and the like are converted into a solution, suspension, or emulsion, if desired with the substances customary and suitable for this purpose, for example, solubilizers or other.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicine, the salts of the compound will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

In one embodiment, this invention provides pharmaceutical compositions comprising a compound of this invention. In one embodiment, such compositions are useful for oral testosterone replacement therapy.

In one embodiment, this invention also provides a composition comprising two or more compounds of this invention, or polymorphs, isomers, hydrates, salts, N-oxides, etc., thereof. The present invention also relates to compositions and pharmaceutical compositions which comprise a compound of this invention alone or in combination with a progestin or estrogen, or in another embodiment, chemotherapeutic compound, osteogenic or myogenic compound, or other agents suitable for the applications as herein described. In one embodiment, the compositions of this invention will comprise a suitable carrier, diluent or salt.

In one embodiment, the methods of this invention may comprise administration of a compound of this invention at various dosages. In another embodiment, the methods of this invention may comprise administration of a compound of formula II of this invention at various dosages. In one embodiment, the compound of this invention is administered at a dosage of 0.1-200 mg per day. In one embodiment, the compound of this invention is administered at a dose of 0.1-10 mg, or in another embodiment, 0.1-26 mg, or in another embodiment, 0.1-60 mg, or in another embodiment, 0.3-16 mg, or in another embodiment, 0.3-30 mg, or in another embodiment, 0.6-26 mg, or in another embodiment, 0.6-60 mg, or in another embodiment, 0.76-16 mg, or in another embodiment, 0.76-60 mg, or in another embodiment, 1-6 mg, or in another embodiment, 1-20 mg, or in another embodiment, 3-16 mg, or in another embodiment, 30-60 mg, or in another embodiment, 30-76 mg, or in another embodiment, 100-2000 mg, or in another embodiment, 1000-20,000 mg.

In one embodiment, the methods of this invention may comprise administration of a compound of this invention at various dosages. In another embodiment, the methods of this invention may comprise administration of a compound of formula II of this invention at various dosages. In one embodiment, the compound of this invention is administered at a dosage of 1 mg. In another embodiment the compound of this invention is administered at a dosage of 6 mg, 10 mg, 16 mg, 20 mg, 26 mg, 30 mg, 36 mg, 40 mg, 46 mg, 50 mg, 56 mg, 60 mg, 66 mg, 70 mg, 76 mg, 80 mg, 86 mg, 90 mg, 96 mg, 100 mg, 200 mg, 500 mg, 1000 mg, 2000 mg, 10,000 mg, or 20,000 mg.

In one embodiment, the present invention provides methods of use comprising the administration of a composition comprising: a) any embodiment of a compound as described herein; and b) additives, a pharmaceutically acceptable carrier or diluent; which is to be understood to include an analog, isomer, metabolite, derivative, pharmaceutically acceptable salt, N-oxide, hydrate or any combination thereof of a compound as herein described, and may comprise compounds of formulas I-XXV.

In some embodiments, the present invention provides methods of use of a composition comprising: a) any embodiment of the compounds as described herein, including an analog, isomer, metabolite, derivative, pharmaceutically acceptable salt, pharmaceutical product, N-oxide, hydrate thereof or any combination thereof; b) a pharmaceutically acceptable carrier or diluent; c) a flow-aid; and d) a lubricant.

In another embodiment, the present invention provides methods of use of a composition comprising: a) any embodiment of the compounds as described herein, including an analog, isomer, metabolite, derivative, pharmaceutically acceptable salt, pharmaceutical product, N-oxide, hydrate thereof or any combination thereof; b) lactose monohydrate; c) microcrystalline cellulose; d) magnesium stearate; e) additives; and f) colloidal silicon dioxide.

In some embodiments, the methods of this invention make use of compositions comprising compounds of this invention, which offer the advantage that the compounds are nonsteroidal ligands for the androgen receptor, and exhibit anabolic activity in vivo. According to this aspect, such compounds are unaccompanied by serious side effects, provide convenient modes of administration, and lower production costs and are orally bioavailable, lack of significant cross-reactivity with other undesired steroid receptors, and may possess long biological half-lives.

In one embodiment, the compositions for administration may be sterile solutions, or in other embodiments, aqueous or non-aqueous, suspensions or emulsions. In one embodiment, the compositions may comprise propylene glycol, polyethylene glycol, injectable organic esters, for example ethyl oleate, or cyclodextrins. In another embodiment, compositions may also comprise wetting, emulsifying and/or dispersing agents. In another embodiment, the compositions may also comprise sterile water or any other sterile injectable medium.

In one embodiment, the invention provides compounds and compositions, including any embodiment described herein, for use in any of the methods of this invention, as described herein. In one embodiment, use of a compound of this invention or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the compound of this invention is being administered.

In some embodiments, the methods of this invention make use of compositions comprising compounds of this invention, which offer the advantage that the compounds are nonsteroidal ligands for the androgen receptor, and exhibit anabolic activity in vivo. According to this aspect, such compounds are unaccompanied by serious side effects, provide convenient modes of administration, and lower production costs and are orally bioavailable, lack significant cross-reactivity with other undesired steroid receptors, and may possess long biological half-lives.

In some embodiments, the compositions will further comprise a 5α-reductase inhibitors (5ARI), a beta-agonist, a SARM or SARMs, a selective estrogen receptor modulator (SERM), an aromatase inhibitor, such as but not limited to anastrazole, exemestane, or letrozole, a GnRH agonist or antagonist, a steroidal or nonsteroidal GR ligand, a steroidal or nonsterodial PR ligand, a steroidal or nonsteroidal AR antagonist, a 17-aldoketoreductase inhibitor or 17β-hydroxysteroid dehydrogenase inhibitor. Such compositions may be used, in some embodiments, for treating a hormone dependent condition, such as, for example, infertility, neoplasia of a hormone-responsive cancer, for example, a gonadal cancer, or a urogenital cancer.

In some embodiments, the composition will comprise the compounds as described herein, as well as another therapeutic compound, including inter alia, a 5ARI such as finasteride, dutasteride, izonsteride; other SARMs, such as, RU-58642, RU-56279, WS9761 A and B, RU-59063, RU-58841, bexlosteride, LG-2293, L-245976, LG-121071, LG-121091, LG-121104, LGD-2226, LGD-2941, YM-92088, YM-175735, LGD-1331, BMS-357597, BMS-391197, S-40503, BMS-482404, EM-4283, EM-4977, BMS-564929, BMS-391197, BMS-434588, BMS-487745, BMS-501949, SA-766, YM-92088, YM-580, LG-123303, LG-123129, PMCol, YM-175735, BMS-591305, BMS-591309, BMS-665139, BMS-665539, CE-590, 116BG33, 154BG31, arcarine, ACP-105; SERMs, such as tamoxifen, 4-hydroxytamoxifen, idoxifene, toremifene, ospemifene, droloxifene, raloxifene, arzoxifene, bazedoxifene, PPT (1,3,5-tris(4-hydroxyphenyl)-4-propyl-1H-pyrazole), DPN, lasofoxifene, pipendoxifene, EM-800, EM-652, nafoxidine, zindoxifene, tesmilifene, miproxifene phosphate, RU 58,688, EM 139, ICI 164,384, ICI 182,780, clomiphene, MER-25, diethylstibestrol, coumestrol, genistein, GW5638, LY353581, zuclomiphene, enclomiphene, delmadinone acetate, DPPE (N,N-diethyl-2-{4-(phenylmethyl)-phenoxy}ethanamine), TSE-424, WAY-070, WAY-292, WAY-818, cyclocommunol, prinaberel, ERB-041, WAY-397, WAY-244, ERB-196, WAY-169122, MF-101, ERb-002, ERB-037, ERB-017, BE-1060, BE-380, BE-381, WAY-358, [$^{18}$F]FEDNP, LSN-500307, AA-102, Ban zhi lian, CT-101, CT-102, VG-101; GnRH agonists or antagonists, such as, leuprolide, goserelin, triptorelin, alfaprostol, histrelin, detirelix, ganirelix, antide iturelix, cetrorelix, ramorelix, ganirelix, antarelix, teverelix, abarelix, ozarelix, sufugolix, prazarelix, degarelix, NBI-56418, TAK-810, acyline; FSH agonist/antagonist, LH agonist/antagonists, aromatase inhibitors, such as, letrozole, anastrazole, atamestane, fadrozole, minamestane, exemestane, plomestane, liarozole, NKS-01, vorozole, YM-511, finrozole, 4-hydroxyandrostenedione, aminogluethimide, rogletimide; steroidal or nonsteroidal glucocorticoid receptor ligands, such as, ZK-216348, ZK-243149, ZK-243185, LGD-5552, mifepristone, RPR-106541, ORG-34517, GW-215864X, sesquicillin, CP-472555, CP-394531, A-222977, AL-438, A-216054, A-276575, CP-394531, CP-409069, UGR-07; steroidal or nonsterodial progesterone receptor ligands; steroidal or nonsteroidal AR antagonists such as flutamide, hydroxyflutamide, bicalutamide, nilutamide, hydroxysteroid dehydrogenase inhibitors, PPARα ligand such as bezafibrate, fenofibrate, gemfibrozil; PPARα ligands such as darglitazone, pioglitazone, rosiglitazone, isaglitazone, rivoglitazone, netoglitazone; dual acting PPAR ligands, such as naveglitazar, farglitazar, tesaglitazar, ragaglitazar, oxeglitazar, PN-2034, PPAR δ; an anti-glucocorticoid such as RU-486; a 17-ketoreductase inhibitor, 3β-DHΔ4,6-isomerase inhibitors, 3β-DHΔ4,5-isomerase inhibitors, 17,20-desmolase inhibitors, p450c17 inhibitors, p450ssc inhibitors, 17,20-lyase inhibitors, or combinations thereof.

In some embodiments, the compositions will further comprise ghrelin receptor ligand or growth hormone analogues and secretagogues, IGF-1, IGF-1 analogues and secretagogues, myostatin analogues, proteasome inhibitors, androgenic-anabolic steroids, Enbrel®, melanocortin 4 receptor agonist, insulins, or combinations thereof. Such compositions may be used, in some embodiments, for promoting growth in feedlot animals.

In some embodiments, the composition will comprise the compounds as described herein, as well as another therapeutic compound, including inter alia, ghrelin receptor ligand or growth hormone analogues and secretagogues, such as, pralmorelin, examorelin, tabimorelin, capimorelin, capromorelin, ipamorelin, EP-01572, EP-1572, or JMV-1843, an androgenic anabolic steroid such as testosterone or oxandrolone, a melanocortin 4 receptor agonist, such as bremelanotide; a ghrelin or analogue thereof, such as human ghrelin, CYT-009-GhrQb, L-692429, GHRP-6, SK&F-110679, U-75799E, leptin (metreleptin, pegylated leptin; a leptin receptor agonist, such as LEP(116-130), OB3, [D-Leu4]-OB3, rAAV-leptin, AAV-hOB, rAAVhOB; an insulin (short-, intermediate-, and long acting formulations); a cortisol or corticosteroid, or a combination thereof.

The invention contemplates, in some embodiments, administration of compositions comprising the individual agents, administered separately and by similar or alternative routes, formulated as appropriately for the route of administration. The invention contemplates, in some embodiments, administration of compositions comprising the individual agents, administered in the same formulation. The invention contemplates, in some embodiments, staggered administration, concurrent administration, of administration of the various agents over a course of time, however, their effects are synergistic in the subject.

It is to be understood that any of the above means, timings, routes, or combinations thereof, of administration of two or more agents is to be considered as being encompassed by the phrase "administered in combination", as described herein.

It is to be understood that reference to "a compound of this invention" or a use thereof is to be considered to encompass use of any compound as herein described, including any embodiment thereof. It is to be considered to encompass all of compounds which may be characterized by the structure of formulas I-XXV.

In one embodiment, the compound is administered in combination with an agent, which treats bone diseases, disorders or conditions, such as osteoporosis, bone fractures, etc., and this invention comprises methods of treating the same, by administering the compounds as herein described, alone or in combination with other agents.

Such agents for combined use may comprise a SERM, as herein described, a bisphosphonate, for example, alendronate, tiludroate, clodroniate, pamidronate, etidronate, alendronate, zolendronate, cimadronate, neridronate, minodronic acid, ibandronate, risedronate, or homoresidronate; a calcitonin, for example, salmon, Elcatonin®, SUN-8577, TJN-135; a vitamin D or derivative (ZK-156979); a vitamin D receptor ligand or analogues thereof, such as calcitriol, topitriol, ZK-150123, TEI-9647, BXL-628, Ro-26-9228, BAL-2299, Ro-65-2299, or DP-035; an estrogen, estrogen derivative, or conjugated estrogen; an antiestrogen, progestin, synthetic estrogen/progestin; a RANK ligand mAb, for example, denosumab or AMG162 (Amgen); a beta 3 integrin receptor antagonist, an osteoclast vacuolar ATPase inhibitor, an antagonist of VEGF binding to osteoclast receptors, a calcium receptor antagonist, PTh (parathyroid hormone) or analogues thereof, PTHrP analogues (parathyroid hormone-related peptide), cathepsin K inhibitors (AAE581), strontium ranelate, tibolone, HCT-1026, PSK3471, gallium maltolate, Nutropin AQ®, prostaglandins, p38 protein kinase inhibitor, a bone morphogenetic protein, an inhibitor of BMP antagonism, an HMG-CoA reductase inhibitor, a vitamin K or derivative, an antiresorptive, an ipriflavone, a fluoride salt, dietary calcium supplement, osteoprotegerin, or any combination thereof. In one embodiment, the combined administration of a SARM as herein described, osteoprotegerin and parathyroid hormone is contemplated for treating any disease, disorder or condition of the bone.

In one embodiment, the compound is administered with an agent used to treat a wasting disease. In some embodiments, agents used to treat a wasting disease include but are not limited to corticosteroids, anabolic steroids, cannabinoids, metoclopramide, cisapride, medroxyprogesterone acetate, megestrol acetate, cyproheptadine, hydrazine sulfate, pentoxifylline, thalidomide, anticytokine antibodies, cytokine inhibitors, eicosapentaenoic acid, indomethacin, ibuprofen, melatonin, insulin, growth hormone, clenbuterol, porcine pancreas extract, IGF-1, IGF-1 analogue and secretagogue, myostatin analogue, proteasome inhibitor, testosterone, oxandrolone, Enbrel®, melanocortin 4 receptor agonist, or a combination thereof.

In one embodiment, the agent used to treat a wasting disease is a ghrelin receptor ligand, growth hormone analogue, or a secretagogue. In some embodiments, ghrelin receptor ligands, growth hormone analogues, or secretagogues include but are not limited to pralmorelin, examorelin, tabimorelin, capimorelin, capromorelin, ipamorelin, EP-01572, EP-1572, or JMV-1843.

In one embodiment, growth promoting agents such as but not limited to TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890 are utilized as agents used to treat a wasting disease.

In other embodiments, agents treating a wasting disease may comprise growth hormone secretagogues such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or, in other embodiments, with growth hormone releasing factor and its analogs or growth hormone and its analogs, or with alpha-adrenergic agonists, such as clonidine or serotinin 5-$HT_D$ agonists, such as sumatriptan, or agents which inhibit somatostatin or its release, such as physostigmine and pyridostigmine. In some embodiments, agents treating a wasting disease may comprise parathyroid hormone, PTH (1-34) or bisphosphonates, such as MK-217 (alendronate). In other embodiments, agents treating wasting disease may further comprise estrogen, a selective estrogen receptor modulator, such as tamoxifen or raloxifene, or other androgen receptor modulators, such as those disclosed in Edwards, J. P. et al., Bio. Med. Chem. Let., 9, 1003-1008 (1999) and Hamann, L. G. et al., J. Med. Chem., 42, 210-212 (1999). In some embodiments, agents treating a wasting disease may further comprise a progesterone receptor agonists ("PRA"), such as levonorgestrel, medroxyprogesterone acetate (MPA). In some embodiments, agents treating a wasting disease may include nutritional supplements, such as those described in U.S. Pat. No. 5,179,080, which, in other embodiments are in combination with whey protein or casein, amino acids (such as leucine, branched amino acids and hydroxymethylbutyrate), triglycerides, vitamins (e.g., A, B6, B12, folate, C, D and E), minerals (e.g., selenium, magnesium, zinc, chromium, calcium and potassium), carnitine, lipoic acid, creatinine, β-hyroxy-β-methylbutyriate (Juven®) and coenzyme Q. In one embodiment, agents treating a wasting disease may further comprise antiresorptive agents, vitamin D analogues, elemental calcium and calcium supplements, cathepsin K inhibitors, MMP inhibitors, vitronectin receptor antagonists, Src SH2 antagonists, vacuolar-$H^+$-ATPase inhibitors, ipriflavone, fluoride, tibolone, prostanoids, 17-beta hydroxysteroid dehydrogenase inhibitors and Src kinase inhibitors.

In one embodiment, the SARM compound is administered with an agent treating osteoporosis. In some embodiments, agents treating osteoporosis include but are not limited to SERMs, calcitonin, vitamin D, vitamin D derivatives, vitamin D receptor ligand, vitamin D receptor ligand analogue, estrogen, estrogen derivative, conjugated estrogen, antiestrogen, progestin, synthetic estrogen, synthetic progestin, RANK ligand monoclonal antibody, integrin receptor antagonist, osteoclast vacuolar ATPase inhibitor, antagonist of VEGF binding to osteoclast receptors, calcium receptor antagonist, parathyroid hormone, parathyroid hormone analogue, parathyroid hormone-related peptide, cathepsin K inhibitor, strontium ranelate, tibolone, HCT-1026, PSK3471, gallium maltolate, Nutropin AQ®, prostaglandin, p38 protein kinase inhibitor, bone morphogenetic protein (BMP), inhibitor of BMP antagonism, HMG-CoA reductase inhibitor, vitamin K, vitamin K derivative, ipriflavone, fluoride salts, dietary calcium supplement, or osteoprotegerin.

In one embodiment, the agent treating osteoporosis is a calcitonin. In some embodiments, calcitonins include but are not limited to salmon, Elcatonin®, SUN-8577, or TJN-135.

In one embodiment, the agent treating osteoporosis is a vitamin D receptor ligand or analogue. In some embodiments, vitamin D receptor ligands or analogues include but are not limited to calcitriol, topitriol, ZK-150123, TEI-9647, BXL-628, Ro-26-9228, BAL-2299, Ro-65-2299, or DP-035.

In one embodiment, the compound of this invention is administered with a vitamin. In some embodiments, vitamins include but are not limited to vitamin D, vitamin E, vitamin K, vitamin B, vitamin C, or a combination thereof.

In some embodiments, any of the compositions of this invention will comprise a compound of formula I-XXV, in any form or embodiment as described herein. In some embodiments, any of the compositions of this invention will consist of a compound of formula I-XXV, in any form or embodiment as described herein. In some embodiments, of the compositions of this invention will consist essentially of a compound of I-XXV, in any form or embodiment as described herein. In some embodiments, the term "comprise" refers to the inclusion of the indicated active agent, such as the compound of formula I-XXV, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

In one embodiment, the present invention provides combined preparations. In one embodiment, the term "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

It is to be understood that this invention is directed to compositions and combined therapies as described herein, for any disease, disorder or condition, as appropriate, as will be appreciated by one skilled in the art. Certain applications of such compositions and combined therapies have been described hereinabove, for specific diseases, disorders and conditions, representing embodiments of this invention, and methods of treating such diseases, disorders and conditions in a subject by administering a compound as herein described, alone or as part of the combined therapy or using the compositions of this invention represent additional embodiments of this invention.

Biological Activity of Selective Androgen Modulator Compounds

In some embodiments, the compounds of this invention possess in vivo tissue selective androgenic and anabolic activity, which is accordingly utilized for particular applications, as will be appreciated by one skilled in the art.

In one embodiment, the methods of this invention are useful a subject, which is a human. In another embodiment, the subject is a mammal. In another embodiment the subject is an animal. In another embodiment the subject is an invertebrate. In another embodiment the subject is a vertebrate. In one embodiment, the subject is a feedlot animal, a beef cattle and/or a finishing livestock.

In one embodiment, the subject is male. In another embodiment, the subject is female. In some embodiments, while the methods as described herein may be useful for treating either males or females, females may respond more advantageously to administration of certain compounds, for certain methods, as described and exemplified herein.

In another embodiment of the present invention, a method is provided for hormonal therapy in a patient (i.e., one suffering from an androgen-dependent condition) which includes contacting an androgen receptor of a patient with a compound and/or a non steroidal agonist of the present invention and/or its analog, derivative, isomer, metabolite, pharmaceutically acceptable salt, pharmaceutical product, polymorph, crystal, impurity, hydrate, N-oxide or any combination thereof, in an amount effective to bind the compound to the androgen receptor and effect a change in an androgen-dependent condition.

In one embodiment of this invention, a method is provided for hormone replacement therapy in a patient (i.e., one suffering from an androgen-dependent condition) which includes administering a compound as herein described and/or its analog, derivative, isomer, metabolite, pharmaceutically acceptable salt, pharmaceutical product, polymorph, crystal, impurity, hydrate, N-oxide or any combination thereof, to a subject, in an amount sufficient to effect a change in a hormone-dependent condition in the subject.

In one embodiment, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for: a) accelerating bone repair; b) treating bone disorders; c) treating bone density loss; d) treating low bone mineral density (BMD); e) treating reduced bone mass; f) treating metabolic bone disease; g) promoting bone growth or regrowth; h) promoting bone restoration; i) promoting bone fracture repair; j) promoting bone remodeling; k) treating bone damage following reconstructive surgery including of the face, hip, or joints; l) enhancing of bone strength and function; m) increasing cortical bone mass; or n) increasing trabecular connectivity.

In one embodiment, the bone related disorder is a genetic disorder, or in another embodiment, is induced as a result of a treatment regimen for a given disease. For example, and in one embodiment, the compounds as herein described are useful in treating a bone-related disorder that arises as a result of cancer metastasis to bone, or in another embodiment, as a result of androgen-deprivation therapy, for example, given in response to prostate carcinogenesis in the subject.

In one embodiment, the bone-related disorder is osteoporosis. In another embodiment, the bone-related disorder is osteopenia. In another embodiment, the bone-related disorder is increased bone resorption. In another embodiment, the bone-related disorder is bone fracture. In another embodiment, the bone-related disorder is bone frailty.

In another embodiment, the bone-related disorder is a loss of bone mineral density (BMD). In another embodiment, the bone-related disorder is any combination of osteoporosis, osteopenia, increased bone resorption, bone fracture, bone frailty and loss of BMD. Each disorder represents a separate embodiment of the present invention.

"Osteoporosis" refers, in one embodiment, to a thinning of the bones with reduction in bone mass due to depletion of calcium and bone protein. In another embodiment, osteoporosis is a systemic skeletal disease, characterized by low bone mass and deterioration of bone tissue, with a consequent increase in bone fragility and susceptibility to fracture. In osteoporotic patients, bone strength is abnormal, in one embodiment, with a resulting increase in the risk of fracture. In another embodiment, osteoporosis depletes both the calcium and the protein collagen normally found in the bone, in one embodiment, resulting in either abnormal bone quality or decreased bone density. In another embodiment, bones that are affected by osteoporosis can fracture with only a minor fall or injury that normally would not cause a bone fracture. The fracture can be, in one embodiment, either in the form of cracking (as in a hip fracture) or collapsing (as in a compression fracture of the spine). The spine, hips, and wrists are common areas of osteoporosis-induced bone fractures, although fractures can also occur in other skeletal areas. Unchecked osteoporosis can lead, in another embodiment, to changes in posture, physical abnormality, and decreased mobility.

In one embodiment, the osteoporosis results from androgen deprivation. In another embodiment, the osteoporosis follows androgen deprivation. In another embodiment, the osteoporosis is primary osteoporosis. In another embodiment, the osteoporosis is secondary osteoporosis. In another embodiment, the osteoporosis is postmenopausal osteoporosis. In another embodiment, the osteoporosis is juvenile osteoporosis. In another embodiment, the osteoporosis is idiopathic osteoporosis. In another embodiment, the osteoporosis is senile osteoporosis.

In one embodiment, the methods of this invention are useful in treating diseases or disorders caused by, or associated with a hormonal disorder, disruption or imbalance. In one embodiment, the hormonal disorder, disruption or imbalance comprises an excess of a hormone. In another embodiment, the hormonal disorder, disruption or imbalance comprises a deficiency of a hormone. In one embodiment, the hormone is a steroid hormone. In another embodiment, the hormone is an estrogen. In another embodiment, the hormone is an androgen. In another embodiment, the hormone is a glucocorticoid. In another embodiment, the hormone is a cortico-steroid. In another embodiment, the hormone is luteinizing hormone (LH). In another embodiment, the hormone is follicle stimulating hormone (FSH). In another embodiment, the hormone is any other hormone known in the art. In another embodiment, the hormonal disorder, disruption or imbalance is associated with menopause. In another embodiment, the hormonal disorder, disruption or imbalance is associated with andropause, andropausal vasomotor symptoms, andropausal gynecomastia, muscle strength and/or function, bone strength and/or function and anger. In another embodiment, hormone deficiency is a result of specific manipulation, as a byproduct of treating a disease or disorder in the subject. For example, the hormone deficiency may be a result of androgen depletion in a subject, as a therapy for prostate cancer in the subject. Each possibility represents a separate embodiment of the present invention.

In another embodiment the invention is directed to treating sarcopenia or cachexia, and associated conditions related thereto, for example diseases or disorders of the bone.

In one embodiment, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for: 1) treating a muscle wasting disorder; 2) preventing a muscle wasting disorder; 3) treating, preventing, suppressing, inhibiting or reducing muscle loss due to a muscle wasting disorder; 4) treating, preventing, inhibiting, reducing or suppressing muscle wasting due to a muscle wasting disorder; 5) treating, preventing, inhibiting, reducing or suppressing muscle protein catabolism due to a muscle wasting disorder; 6) treating, preventing, inhibiting, reducing or suppressing end stage renal disease; and/or 7) treating, preventing, inhibiting, reducing or suppressing frailty.

In another embodiment, the use of a compound for treating a subject having a muscle wasting disorder, or any of the disorders described herein, includes administering a pharmaceutical composition including a compound as herein described. In another embodiment, the administering step includes intravenously, intraarterially, or intramuscularly injecting to said subject said pharmaceutical composition in liquid form; subcutaneously implanting in said subject a pellet containing said pharmaceutical composition; orally administering to said subject said pharmaceutical composition in a liquid or solid form; or topically applying to the skin surface of said subject said pharmaceutical composition.

A muscle is a tissue of the body that primarily functions as a source of power. There are three types of muscles in the body: a) skeletal muscle—the muscle responsible for moving extremities and external areas of the bodies; b) cardiac muscle—the heart muscle; and c) smooth muscle—the muscle that is in the walls of arteries and bowel.

A wasting condition or disorder is defined herein as a condition or disorder that is characterized, at least in part, by an abnormal, progressive loss of body, organ or tissue mass. A wasting condition can occur as a result of a pathology such as, for example, cancer, or an infection, or it can be due to a physiologic or metabolic state, such as disuse deconditioning that can occur, for example, due to prolonged bed rest or when a limb is immobilized, such as in a cast. A wasting condition can also be age associated. The loss of body mass that occurs during a wasting condition can be characterized by a loss of total body weight, or a loss of organ weight such as a loss of bone or muscle mass due to a decrease in tissue protein.

In one embodiment, "muscle wasting" or "muscular wasting", used herein interchangeably, refer to the progressive loss of muscle mass and/or to the progressive weakening and degeneration of muscles, including the skeletal or voluntary muscles which control movement, cardiac muscles which control the heart, and smooth muscles. In one embodiment, the muscle wasting condition or disorder is a chronic muscle wasting condition or disorder. "Chronic muscle wasting" is defined herein as the chronic (i.e. persisting over a long period of time) progressive loss of muscle mass and/or to the chronic progressive weakening and degeneration of muscle.

The loss of muscle mass that occurs during muscle wasting can be characterized by a muscle protein breakdown or degradation, by muscle protein catabolism. Protein catabolism occurs because of an unusually high rate of protein degradation, an unusually low rate of protein synthesis, or a combination of both. Protein catabolism or depletion, whether caused by a high degree of protein degradation or a low degree of protein synthesis, leads to a decrease in muscle mass and to muscle wasting. The term "catabolism" has its commonly known meaning in the art, specifically an energy burning form of metabolism.

Muscle wasting can occur as a result of a pathology, disease, condition or disorder. In one embodiment, the pathology, illness, disease or condition is chronic. In another embodiment, the pathology, illness, disease or condition is genetic. In another embodiment, the pathology, illness, disease or condition is neurological. In another embodiment, the pathology, illness, disease or condition is infectious. As described herein, the pathologies, diseases, conditions or disorders for which the compounds and compositions of the present invention are administered are those that directly or indirectly produce a wasting (i.e. loss) of muscle mass, that is a muscle wasting disorder.

In one embodiment, this invention is directed to a method of treating, reducing the severity, reducing the incidence, delaying the onset, or reducing the pathogenesis of Duchenne muscular dystrophy in a subject in need thereof, comprising the step of administering to said subject a selective androgen receptor modulator (SARM) compound represented by the structure of formula S-XXIII:

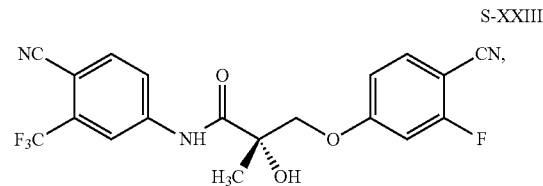

S-XXIII or its isomer, pharmaceutically acceptable salt, hydrate, N-oxide, or any combination thereof.

In one embodiment, this invention is directed to a method of treating, reducing the severity, reducing the incidence, delaying the onset, or reducing the pathogenesis of Duchenne muscular dystrophy in a subject in need thereof, comprising the step of administering a pharmaceutical composition comprising a selective androgen receptor modulator (SARM) compound represented by the structure of formula S-XXIII:

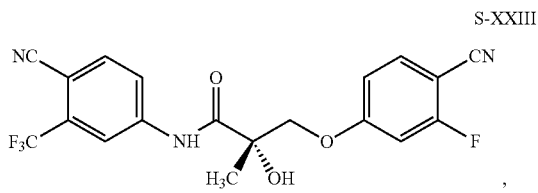 [SMILES: C[C@](O)(COc1ccc(C#N)c(F)c1)C(=O)Nc1ccc(C#N)c(C(F)(F)F)c1]

S-XXIII or its isomer, pharmaceutically acceptable salt, hydrate, N-oxide, or any combination thereof; and a pharmaceutically acceptable carrier.

In another embodiment, the method of this invention for treating, reducing the severity, reducing the incidence, delaying the onset, or reducing the pathogenesis of Duchenne muscular dystrophy in a subject in need thereof, further increases the quality of life of said subject. In another embodiment, the method of this invention for treating, reducing the severity, reducing the incidence, delaying the onset, or reducing the pathogenesis of Duchenne muscular dystrophy in a subject in need thereof, further increases the survival of said subject. In another embodiment, the method of this invention for treating, reducing the severity, reducing the incidence, delaying the onset, or reducing the pathogenesis of Duchenne muscular dystrophy in a subject in need thereof, further increases the physical function of said subject. In another embodiment, the method of this invention for treating, reducing the severity, reducing the incidence, delaying the onset, or reducing the pathogenesis of Duchenne muscular dystrophy in a subject in need thereof, further delays the loss of body weight of said subject. In another embodiment, the method of this invention for treating, reducing the severity, reducing the incidence, delaying the onset, or reducing the pathogenesis of Duchenne muscular dystrophy in a subject in need thereof, further delays loss of ambulation of said subject. In another embodiment, the method of this invention for treating, reducing the severity, reducing the incidence, delaying the onset, or reducing the pathogenesis of Duchenne muscular dystrophy in a subject in need thereof, further delays loss of lean body mass of said subject. In another embodiment, the method of this invention for treating, reducing the severity, reducing the incidence, delaying the onset, or reducing the pathogenesis of Duchenne muscular dystrophy in a subject in need thereof, further delays the gain of fat body mass of said subject. In another embodiment, the method of this invention for treating, reducing the severity, reducing the incidence, delaying the onset, or reducing the pathogenesis of Duchenne muscular dystrophy in a subject in need thereof, further delays muscle fibrosis of said subject. In another embodiment, the method of this invention for treating, reducing the severity, reducing the incidence, delaying the onset, or reducing the pathogenesis of Duchenne muscular dystrophy in a subject in need thereof, further delays cardiomyopathy of said subject. In another embodiment, the method of this invention for treating, reducing the severity, reducing the incidence, delaying the onset, or reducing the pathogenesis of Duchenne muscular dystrophy in a subject in need thereof, further delays respiratory failure or insufficiency of said subject. In another embodiment, the method of this invention for treating, reducing the severity, reducing the incidence, delaying the onset, or reducing the pathogenesis of Duchenne muscular dystrophy in a subject in need thereof, further increases the exercise tolerance of said subject. In another embodiment, the method of this invention for treating, reducing the severity, reducing the incidence, delaying the onset, or reducing the pathogenesis of Duchenne muscular dystrophy in a subject in need thereof, further decreases the extent and severity of muscle contractures of said subject. In another embodiment, the method of this invention for treating, reducing the severity, reducing the incidence, delaying the onset, or reducing the pathogenesis of Duchenne muscular dystrophy in a subject in need thereof, further prevents or delays scoliosis of said subject.

In another embodiment, the method of this invention for treating, reducing the severity, reducing the incidence, delaying the onset, or reducing the pathogenesis of Duchenne muscular dystrophy in a subject in need thereof, further delays onset or improves symptoms of cardiomyopathy and/or respiratory function.

In one embodiment, this invention is directed to a method of increasing the physical function of a subject suffering from Duchenne muscular dystrophy, comprising the step of administering to said subject a selective androgen receptor modulator (SARM) compound represented by the structure of formula S-XXIII:

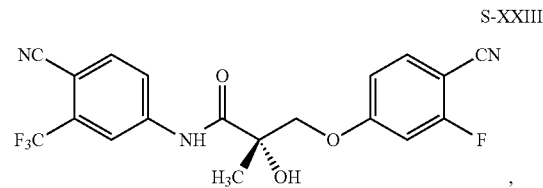 [SMILES: C[C@](O)(COc1ccc(C#N)c(F)c1)C(=O)Nc1ccc(C#N)c(C(F)(F)F)c1]

S-XXIII or its isomer, pharmaceutically acceptable salt, hydrate, N-oxide, or any combination thereof.

In one embodiment, this invention is directed to a method of increasing the quality of life of a subject suffering from Duchenne muscular dystrophy, comprising the step of administering to said subject a selective androgen receptor modulator (SARM) compound represented by the structure of formula S-XXIII:

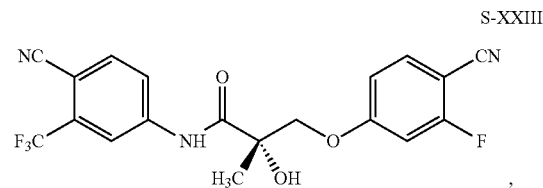 [SMILES: C[C@](O)(COc1ccc(C#N)c(F)c1)C(=O)Nc1ccc(C#N)c(C(F)(F)F)c1]

S-XXIII or its isomer, pharmaceutically acceptable salt, hydrate, N-oxide, or any combination thereof.

The term "quality of life" refers herein to improvement of one or more of the following: motor skills such as ambulation and limb strength, less fatigue; delaying onset, treating, or preventing cardiopathies; delaying onset, treating, or preventing respiratory symptoms and respiratory insufficiency or failure; or improved cognition.

In one embodiment, this invention is directed to a method of increasing the survival of a subject suffering from Duchenne muscular dystrophy, comprising the step of administering to said subject a selective androgen receptor modu lator (SARM) compound represented by the structure of formula S-XXIII:

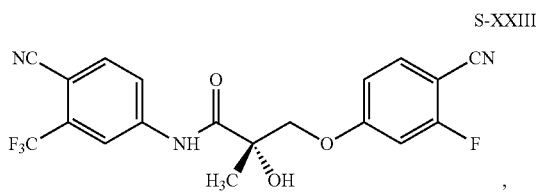

or its isomer, pharmaceutically acceptable salt, hydrate, N-oxide, or any combination thereof.

In one embodiment, this invention provides a method of treating, reducing the severity, reducing the incidence, delaying the onset, or reducing the pathogenesis of cardiomyopathy in a subject suffering from Duchenne muscular dystrophy, comprising the step of administering to said subject a selective androgen receptor modulator (SARM) compound represented by the structure of formula S-XXIII:

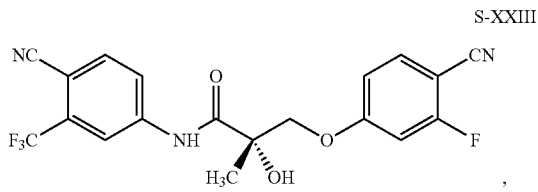

or its isomer, pharmaceutically acceptable salt, hydrate, N-oxide, or any combination thereof.

In another embodiment, the method of this invention for treating, reducing the severity, reducing the incidence, delaying the onset, or reducing the pathogenesis of cardiomyopathy in a subject suffering from Duchenne muscular dystrophy, further increases the quality of life of said subject. In another embodiment, the method of this invention for treating, reducing the severity, reducing the incidence, delaying the onset, or reducing the pathogenesis of cardiomyopathy in a subject suffering from Duchenne muscular dystrophy, further increases the survival of said subject. In another embodiment, the method of this invention for treating, reducing the severity, reducing the incidence, delaying the onset, or reducing the pathogenesis of cardiomyopathy a subject suffering from Duchenne muscular dystrophy, further increases the physical function of said subject.

In one embodiment, this invention provides a method of treating, reducing the severity, reducing the incidence, delaying the onset, or reducing the pathogenesis of respiratory failure in a subject suffering from Duchenne muscular dystrophy, comprising the step of administering to said subject a selective androgen receptor modulator (SARM) compound represented by the structure of formula S-XXIII:

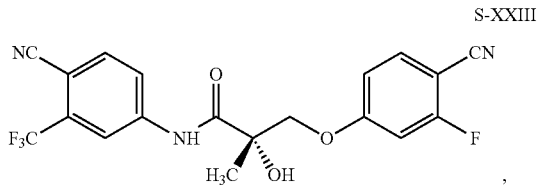

or its isomer, pharmaceutically acceptable salt, hydrate, N-oxide, or any combination thereof.

In another embodiment, the method of this invention for treating, reducing the severity, reducing the incidence, delaying the onset, or reducing the pathogenesis of respiratory failure in a subject suffering from Duchenne muscular dystrophy, further increases the quality of life of said subject. In another embodiment, the method of this invention for treating, reducing the severity, reducing the incidence, delaying the onset, or reducing the pathogenesis of respiratory failure in a subject suffering from Duchenne muscular dystrophy, further increases the survival of said subject. In another embodiment, the method of this invention for treating, reducing the severity, reducing the incidence, delaying the onset, or reducing the pathogenesis of respiratory failure in a subject suffering from Duchenne muscular dystrophy, further increases the physical function of said subject.

In one embodiment, this invention provides a method of treating, reducing the severity, reducing the incidence, delaying the onset, or reducing the pathogenesis of Becker muscular dystrophy or myotonic dystrophy in a subject in need thereof, comprising the step of administering to said subject a selective androgen receptor modulator (SARM) compound represented by the structure of formula S-XXIII:

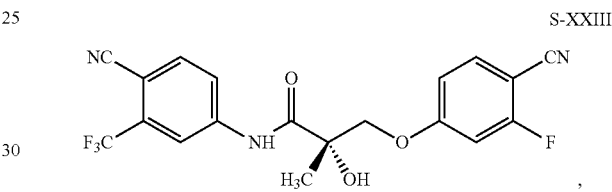

or its isomer, pharmaceutically acceptable salt, hydrate, N-oxide, or any combination thereof.

In another embodiment, the method of this invention for treating, reducing the severity, reducing the incidence, delaying the onset, or reducing the pathogenesis of Becker muscular dystrophy or myotonic dystrophy in a subject in need thereof, further increases the quality of life of said subject. In another embodiment, the method of this invention for treating, reducing the severity, reducing the incidence, delaying the onset, or reducing the pathogenesis of Becker muscular dystrophy or myotonic dystrophy in a subject in need thereof, further increases the survival of said subject. In another embodiment, the method of this invention for treating, reducing the severity, reducing the incidence, delaying the onset, or reducing the pathogenesis of Becker muscular dystrophy or myotonic dystrophy in a subject in need thereof, further increases the physical function of said subject.

In another embodiment, the method of this invention for treating, reducing the severity, reducing the incidence, delaying the onset, or reducing the pathogenesis of Becker muscular dystrophy or myotonic dystrophy in a subject in need thereof, further delays onset or improves symptoms of cardiomyopathy and/or respiratory function.

In one embodiment, this invention is directed to a method of treating, reducing the severity, reducing the incidence, delaying the onset, or reducing the pathogenesis of myotonic dystrophy, limb-girdle muscular dystrophy, facioscapulhumeral muscular dystrophy, congenital muscular dystrophy, oculopharyngeal muscular dystrophy, distal muscular dystrophy, or Emery-Dreifuss muscular dystrophy in a subject in need thereof, comprising the step of administering to said subject a selective androgen receptor modulator (SARM) compound represented by the structure of formula S-XXIII:

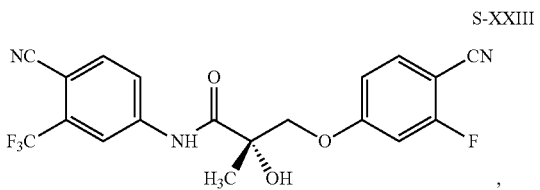

S-XXIII or its isomer, pharmaceutically acceptable salt, hydrate, N-oxide, or any combination thereof.

In one embodiment, this invention is directed to a method of treating, reducing the severity, reducing the incidence, delaying the onset, or reducing the pathogenesis of myotonic dystrophy in a subject in need thereof, comprising the step of administering to said subject a selective androgen receptor modulator (SARM) compound represented by the structure of formula S-XXIII:

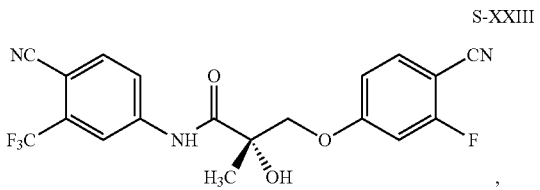 [SMILES: C[C@](O)(COc1ccc(C#N)c(F)c1)C(=O)Nc1ccc(C#N)c(C(F)(F)F)c1]

S-XXIII or its isomer, pharmaceutically acceptable salt, hydrate, N-oxide, or any combination thereof.

In one embodiment, this invention is directed to a method of treating, reducing the severity, reducing the incidence, delaying the onset, or reducing the pathogenesis of limb-girdle muscular dystrophy in a subject in need thereof, comprising the step of administering to said subject a selective androgen receptor modulator (SARM) compound represented by the structure of formula S-XXIII:

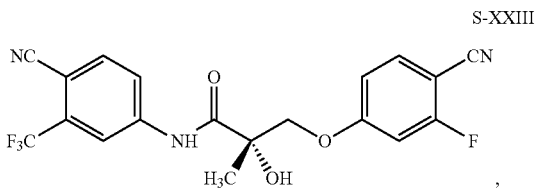 [SMILES: C[C@](O)(COc1ccc(C#N)c(F)c1)C(=O)Nc1ccc(C#N)c(C(F)(F)F)c1]

S-XXIII or its isomer, pharmaceutically acceptable salt, hydrate, N-oxide, or any combination thereof.

In one embodiment, this invention is directed to a method of treating, reducing the severity, reducing the incidence, delaying the onset, or reducing the pathogenesis of facioscapulhumeral muscular dystrophy in a subject in need thereof, comprising the step of administering to said subject a selective androgen receptor modulator (SARM) compound represented by the structure of formula S-XXIII:

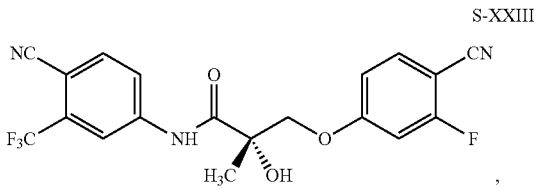 [SMILES: C[C@](O)(COc1ccc(C#N)c(F)c1)C(=O)Nc1ccc(C#N)c(C(F)(F)F)c1]

S-XXIII or its isomer, pharmaceutically acceptable salt, hydrate, N-oxide, or any combination thereof.

In one embodiment, this invention is directed to a method of treating, reducing the severity, reducing the incidence, delaying the onset, or reducing the pathogenesis of congenital muscular dystrophy in a subject in need thereof, comprising the step of administering to said subject a selective androgen receptor modulator (SARM) compound represented by the structure of formula S-XXIII:

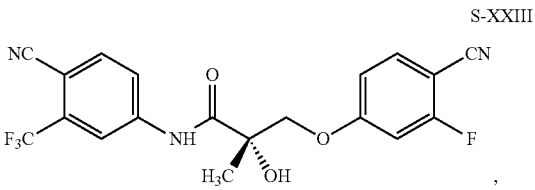 [SMILES: C[C@](O)(COc1ccc(C#N)c(F)c1)C(=O)Nc1ccc(C#N)c(C(F)(F)F)c1]

S-XXIII or its isomer, pharmaceutically acceptable salt, hydrate, N-oxide, or any combination thereof.

In one embodiment, this invention is directed to a method of treating, reducing the severity, reducing the incidence, delaying the onset, or reducing the pathogenesis of oculopharyngeal muscular dystrophy in a subject in need thereof, comprising the step of administering to said subject a selective androgen receptor modulator (SARM) compound represented by the structure of formula S-XXIII:

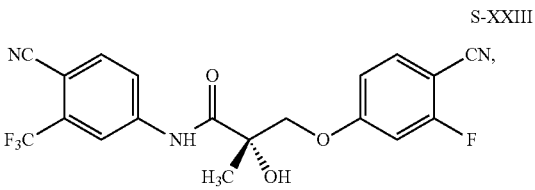 [SMILES: C[C@](O)(COc1ccc(C#N)c(F)c1)C(=O)Nc1ccc(C#N)c(C(F)(F)F)c1]

S-XXIII, or its isomer, pharmaceutically acceptable salt, hydrate, N-oxide, or any combination thereof.

In one embodiment, this invention is directed to a method of treating, reducing the severity, reducing the incidence, delaying the onset, or reducing the pathogenesis of distal muscular dystrophy in a subject in need thereof, comprising the step of administering to said subject a selective androgen receptor modulator (SARM) compound represented by the structure of formula S-XXIII:

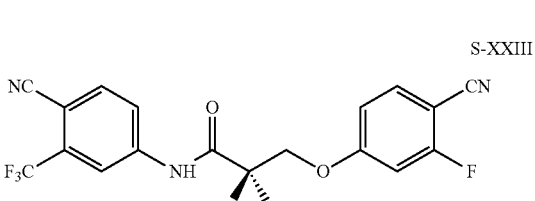

S-XXIII or its isomer, pharmaceutically acceptable salt, hydrate, N-oxide, or any combination thereof.

In one embodiment, this invention is directed to a method of treating, reducing the severity, reducing the incidence, delaying the onset, or reducing the pathogenesis of Emery-Dreifuss muscular dystrophy in a subject in need thereof, comprising the step of administering to said subject a selective androgen receptor modulator (SARM) compound represented by the structure of formula S-XXIII:

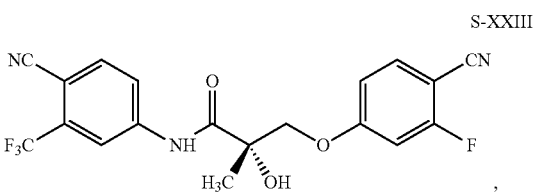 [SMILES: C[C@](O)(COc1ccc(C#N)c(F)c1)C(=O)Nc1ccc(C#N)c(C(F)(F)F)c1]

S-XXIII or its isomer, pharmaceutically acceptable salt, hydrate, N-oxide, or any combination thereof.

In another embodiment, the method of this invention for treating, reducing the severity, reducing the incidence, delaying the onset, or reducing the pathogenesis of myotonic dystrophy, limb-girdle muscular dystrophy, facioscapulhumeral muscular dystrophy, congenital muscular dystrophy, oculopharyngeal muscular dystrophy, distal muscular dystrophy, or Emery-Dreifuss muscular dystrophy in a subject in need thereof, further increases the quality of life of said subject.

In another embodiment, the method of this invention for treating, reducing the severity, reducing the incidence, delaying the onset, or reducing the pathogenesis of myotonic dystrophy, limb-girdle muscular dystrophy, facioscapulhumeral muscular dystrophy, congenital muscular dystrophy, oculopharyngeal muscular dystrophy, distal muscular dystrophy, or Emery-Dreifuss muscular dystrophy in a subject in need thereof, further increases the survival of said subject. In another embodiment, the method of this invention for treating, reducing the severity, reducing the incidence, delaying the onset, or reducing the pathogenesis of myotonic dystrophy, limb-girdle muscular dystrophy, facioscapulhumeral muscular dystrophy, congenital muscular dystrophy, oculopharyngeal muscular dystrophy, distal muscular dystrophy, or Emery-Dreifuss muscular dystrophy in a subject in need thereof, further increases the physical function of said subject.

In another embodiment, the method of this invention for treating, reducing the severity, reducing the incidence, delaying the onset, or reducing the pathogenesis of myotonic dystrophy, limb-girdle muscular dystrophy, facioscapulhumeral muscular dystrophy, congenital muscular dystrophy, oculopharyngeal muscular dystrophy, distal muscular dystrophy, or Emery-Dreifuss muscular dystrophy in a subject in need thereof, further delays onset or improves symptoms of cardiomyopathy and/or respiratory function.

In one embodiment, this invention provides a method of treating, reducing the incidence of, delaying progression of, reducing the severity of, or alleviating symptoms associated with a muscle wasting disorder in a subject, comprising the step of administering to said subject the selective androgen receptor modulator compound of this invention or its isomer, pharmaceutically acceptable salt, pharmaceutical product, crystal, hydrate, N-oxide or any combination thereof, or a composition comprising the same, in an amount effective to treat the muscle wasting disorder in said subject. In another embodiment, the compound is a compound of formula S-XXIII.

According to this aspect, and in one embodiment, the muscle wasting disorder is due to a pathology, illness, disease or condition. In one embodiment, the pathology, illness, disease or condition is neurological, infectious, chronic or genetic. In one embodiment, the pathology, illness, disease or condition is a muscular dystrophy, a muscular atrophy, X-linked spinal-bulbar muscular atrophy (SBMA), a cachexia, malnutrition, leprosy, diabetes, renal disease, chronic obstructive pulmonary disease (COPD), cancer, end stage renal failure, sarcopenia, emphysema, osteomalacia, HIV infection, AIDS, or cardiomyopathy. In one embodiment, the compound is a compound of this invention. In another embodiment, the compound is a compound of formula S-XXIII.

In one embodiment, the muscle wasting disorder is an age-associated muscle wasting disorder; a disuse deconditioning-associated muscle wasting disorder; or the muscle wasting disorder is due to chronic lower back pain, burns, central nervous system (CNS) injury or damage, peripheral nerve injury or damage, spinal cord injury or damage, chemical injury or damage, or alcoholism.

In one embodiment, this invention provides a method of treating, reducing the severity, reducing the incidence, delaying the onset, or reducing the pathogenesis of cardiovascular disease in a human subject, comprising the step of administering an effective amount of a compound of this invention or its isomer, pharmaceutically acceptable salt, pharmaceutical product, crystal, N-oxide, hydrate or any combination thereof to said subject. In another embodiment, the compound is a compound of formula S-XXIII.

In one embodiment, this invention provides a method of treating, reducing the severity, reducing the incidence, delaying the onset, or reducing the pathogenesis of cardiovascular disease in a human subject suffering from Duchenne muscular dystrophy comprising the step of administering an effective amount of a compound of this invention or its isomer, pharmaceutically acceptable salt, pharmaceutical product, crystal, N-oxide, hydrate or any combination thereof to said subject. In another embodiment, the compound is a compound of formula S-XXIII.

In one embodiment, this invention provides a method of treating, reducing the severity, reducing the incidence, delaying the onset, or reducing the pathogenesis of cardiovascular disease in a human subject suffering from Becker muscular dystrophy comprising the step of administering an effective amount of a compound of this invention or its isomer, pharmaceutically acceptable salt, pharmaceutical product, crystal, N-oxide, hydrate or any combination thereof to said subject. In another embodiment, the compound is a compound of formula S-XXIII.

In one embodiment, this invention provides a method of treating, reducing the severity, reducing the incidence, delaying the onset, or reducing the pathogenesis of cardiovascular disease in a human subject suffering from myotonic dystrophy comprising the step of administering an effective amount of a compound of this invention or its isomer, pharmaceutically acceptable salt, pharmaceutical product, crystal, N-oxide, hydrate or any combination thereof to said subject. In another embodiment, the compound is a compound of formula S-XXIII.

In one embodiment, this invention provides a method of treating, reducing the severity, reducing the incidence, delaying the onset, or reducing the pathogenesis of cachexia in a subject, comprising the step of administering an effective amount of a compound of this invention or its isomer, pharmaceutically acceptable salt, pharmaceutical product, crystal, N-oxide, hydrate or any combination thereof to said subject. In one embodiment, the compound is of formula S-XXIII.

In one embodiment, the present invention provides a method of reducing a fat mass in a subject comprising the step of administering an effective amount of a compound of this invention or its isomer, pharmaceutically acceptable salt, pharmaceutical product, crystal, N-oxide, hydrate or any combination thereof to the subject. In another embodiment, the compound is a compound of formula S-XXIII.

In one embodiment, the present invention provides a method of reducing a fat mass in a subject suffering from Duchenne muscular dystrophy comprising the step of administering an effective amount of a compound of this invention or its isomer, pharmaceutically acceptable salt, pharmaceutical product, crystal, N-oxide, hydrate or any combination thereof to the subject. In another embodiment, the compound is a compound of formula S-XXIII. In one embodiment, the present invention provides a method of reducing or preventing fibrosis in a subject suffering from Duchenne muscular dystrophy comprising the step of administering an effective amount of a compound of formula S-XXIII or its isomer, pharmaceutically acceptable salt, pharmaceutical product, crystal, N-oxide, hydrate or any combination thereof to the subject.

In one embodiment, the present invention provides a method of reducing a fat mass in a subject suffering from Becker muscular dystrophy comprising the step of administering an effective amount of a compound of this invention or its isomer, pharmaceutically acceptable salt, pharmaceutical product, crystal, N-oxide, hydrate or any combination thereof to the subject. In another embodiment, the compound is a compound of formula S-XXIII. In one embodiment, the present invention provides a method of reducing or preventing fibrosis in a subject suffering from Becker muscular dystrophy comprising the step of administering an effective amount of a compound of formula S-XXIII or its isomer, pharmaceutically acceptable salt, pharmaceutical product, crystal, N-oxide, hydrate or any combination thereof to the subject.

In one embodiment, the present invention provides a method of reducing a fat mass in a subject suffering from myotonic dystrophy comprising the step of administering an effective amount of a compound of this invention or its isomer, pharmaceutically acceptable salt, pharmaceutical product, crystal, N-oxide, hydrate or any combination thereof to the subject. In another embodiment, the compound is a compound of formula S-XXIII. In one embodiment, the present invention provides a method of reducing or preventing fibrosis in a subject suffering from myotonic dystrophy comprising the step of administering an effective amount of a compound of formula S-XXIII or its isomer, pharmaceutically acceptable salt, pharmaceutical product, crystal, N-oxide, hydrate or any combination thereof to the subject.

In one embodiment, the present invention provides a method of increasing a lean mass in a subject comprising the step of administering an effective amount of a compound of this invention or its isomer, pharmaceutically acceptable salt, pharmaceutical product, crystal, N-oxide, hydrate or any combination thereof to the subject. In another embodiment, the compound is a compound of formula S-XXIII.

In one embodiment, the present invention provides a method of increasing a lean mass in a subject suffering from Duchenne muscular dystrophy comprising the step of administering an effective amount of a compound of this invention or its isomer, pharmaceutically acceptable salt, pharmaceutical product, crystal, N-oxide, hydrate or any combination thereof to the subject. In another embodiment, the compound is a compound of formula S-XXIII.

In one embodiment, the present invention provides a method of increasing a lean mass in a subject suffering from Becker muscular dystrophy comprising the step of administering an effective amount of a compound of this invention or its isomer, pharmaceutically acceptable salt, pharmaceutical product, crystal, N-oxide, hydrate or any combination thereof to the subject. In another embodiment, the compound is a compound of formula S-XXIII.

In one embodiment, the present invention provides a method of increasing a lean mass in a subject suffering from myotonic dystrophy comprising the step of administering an effective amount of a compound of this invention or its isomer, pharmaceutically acceptable salt, pharmaceutical product, crystal, N-oxide, hydrate or any combination thereof to the subject. In another embodiment, the compound is a compound of formula S-XXIII.

In another embodiment, this invention provides a method of treating, reducing the incidence of, delaying progression of, reducing the severity of, or alleviating symptoms associated with a muscle wasting disorder; reducing a fat mass; reducing or preventing fibrosis; or increasing a lean mass in a subject, comprising the step of administering an effective amount of a compound of this invention or its isomer, pharmaceutically acceptable salt, pharmaceutical product, crystal, N-oxide, hydrate or any combination thereof to the subject as herein described. In another embodiment, the compound is a compound of formula S-XXIII.

In one embodiment, muscle wasting in a subject is a result of the subject having a muscular dystrophy; muscle atrophy; or X-linked spinal-bulbar muscular atrophy (SBMA).

The muscular dystrophies are genetic diseases characterized by progressive weakness and degeneration of the skeletal or voluntary muscles that control movement. The muscles of the heart and some other involuntary muscles are also affected in some forms of muscular dystrophy. The nine major forms of muscular dystrophy (MD) are: Duchenne muscular dystrophy, myotonic dystrophy, Becker muscular dystrophy, limb-girdle muscular dystrophy, facioscapulhumeral muscular dystrophy, congenital muscular dystrophy, oculopharyngeal muscular dystrophy, distal muscular dystrophy and Emery-Dreifuss muscular dystrophy.

Muscular dystrophy can affect people of all ages. Although some forms first become apparent in infancy or childhood, others may not appear until middle age or later. Myotonic dystrophy is the most common of these diseases in adults. Myotonic dystrophy is an autosomal dominant genetic disease that occurs in 1/8000 people and is characterized by 2 types. Type I has a genetic defect in the DMPK gene whereas type II has a genetic defect in the CNBP gene. The mutation is an abnormal repeat of a DNA segment which presents a disease phenotype of variable severity in the $2^{nd}$ or $3^{rd}$ decade of life. Symptoms of the disease may include inter alia prolonged contractions (myotonia) of certain muscles, cataracts, cardiac conduction defects, balding, or male infertility.

Duchenne MD is the most common form, typically affecting children. Duchenne muscular dystrophy includes weakness and degeneration of skeletal and voluntary muscle which is exacerbated by high impact exercise, muscle contractures that worsen mobility if not corrected, and scoliosis. Although braces and walkers provide some protection, declines in physical function result in loss of ambulation during childhood leading to wheelchair confinement, and eventually impaired cardiac (cardiomyopathy) or respiratory (diaphragm fibrosis) function leads to death. Average life expectancy has improved (and rare cases of men living into their $4^{th}$ or $5^{th}$ decade) as a result of better respiratory (glucocorticoids) and cardiac (ACE inhibitors, angiotensin receptor blockers, and beta-blockers) supportive care but no disease-modifying therapeutics exist.

Becker muscular dystrophy is a rarer and milder variation of Duchenne muscular dystrophy caused by DMD mutants that do not completely abrogate dystrophin glycoprotein complex function in males or more commonly is observed in some female carriers (Duchenne muscular dystrophy is often asymptomatic in females).

In one embodiment, this invention provides therapeutic effects on dystrophic skeletal, cardiac, and diaphragm muscle, or may delay onset or improve symptoms of loss of mobility/autonomy, cardiomyopathy, or respiratory insufficiency in Duchenne muscular dystrophy or Becker muscular dystrophy and other muscular dystrophy patients; by administering the compound of this invention.

Muscle atrophy (MA) is characterized by wasting away or diminution of muscle and a decrease in muscle mass. For example, post-polio MA is a muscle wasting that occurs as part of the post-polio syndrome (PPS). The atrophy includes weakness, muscle fatigue, and pain.

Another type of MA is X-linked spinal-bulbar muscular atrophy (SBMA—also known as Kennedy's Disease). This disease arises from a defect in the androgen receptor gene on the X chromosome, affects only males, and its onset is in adulthood. Because the primary disease cause is an androgen receptor mutation, androgen replacement is not a current therapeutic strategy. There are some investigational studies where exogenous testosterone propionate is being given to boost the levels of androgen with hopes of overcoming androgen insensitivity and perhaps provide an anabolic effect. Still, use of supraphysiological levels of testosterone for supplementation will have limitations and other potentially serious complications.

Sarcopenia is a debilitating disease that afflicts the elderly and chronically ill patients and is characterized by loss of muscle mass and function. Further, increased lean body mass is associated with decreased morbidity and mortality for certain muscle-wasting disorders. In addition, other circumstances and conditions are linked to, and can cause muscle wasting disorders. For example, studies have shown that in severe cases of chronic lower back pain, there is paraspinal muscle wasting.

Muscle wasting and other tissue wasting is also associated with advanced age. It is believed that general weakness in old age is due to muscle wasting. As the body ages, an increasing proportion of skeletal muscle is replaced by fibrous tissue. The result is a significant reduction in muscle power, performance and endurance.

Long term hospitalization due to illness or injury, or disuse deconditioning that occurs, for example, when a limb is immobilized, can also lead to muscle wasting, or wasting of other tissue. Studies have shown that in patients suffering injuries, chronic illnesses, burns, trauma or cancer, who are hospitalized for long periods of time, there is a long-lasting unilateral muscle wasting, and a decrease in body mass.

Injuries or damage to the central nervous system (CNS) are also associated with muscle wasting and other wasting disorders. Injuries or damage to the CNS can be, for example, caused by diseases, trauma or chemicals. Examples are central nerve injury or damage, peripheral nerve injury or damage and spinal cord injury or damage. In one embodiment CNS damage or injury comprise Alzheimer's diseases (AD), anger (mood); anorexia, anorexia nervosa, anorexia associated with aging and/or assertiveness (mood).

In another embodiment, muscle wasting or other tissue wasting may be a result of alcoholism, and may be treated with the compounds and compositions of the invention, representing embodiments thereof.

In one embodiment, the invention provides a use of SARM compounds as described herein or its prodrug, analog, isomer, metabolite, derivative, pharmaceutically acceptable salt, pharmaceutical product, polymorph, crystal, impurity, N-oxide, hydrate or any combination thereof for the treatment of a wasting disease, disorder or condition in a subject.

In one embodiment, the wasting disease, disorder or condition being treated is associated with chronic illness.

This invention is directed to treating, in some embodiments, any wasting disorder, which may be reflected in muscle wasting, weight loss, malnutrition, starvation, or any wasting or loss of functioning due to a loss of tissue mass.

In some embodiments, wasting diseases or disorders, such as cachexia, malnutrition, tuberculosis, leprosy, diabetes, renal disease, chronic obstructive pulmonary disease (COPD), cancer, end stage renal failure, sarcopenia, emphysema, osteomalacia, or cardiomyopathy, may be treated by the methods of this invention, via the administration of a SARM compound as herein described, compositions comprising the same, with or without additional drugs, compounds, or agents, which provide a therapeutic effect for the condition being treated.

In some embodiments, wasting is due to infection with enterovirus, Epstein-Barr virus, herpes zoster, HIV, trypanosomes, influenza, coxsackie, *rickettsia, trichinella, schistosoma* or mycobacteria, and this invention, in some embodiments, provides methods of treatment thereof.

Cachexia is weakness and a loss of weight caused by a disease or as a side effect of illness. Cardiac cachexia, i.e. a muscle protein wasting of both the cardiac and skeletal muscle, is a characteristic of congestive heart failure. Cancer cachexia is a syndrome that occurs in patients with solid tumors and hematological malignancies and is manifested by weight loss with massive depletion of both adipose tissue and lean muscle mass.

Cachexia is also seen in acquired immunodeficiency syndrome (AIDS), human immunodeficiency virus (HIV)-associated myopathy and/or muscle weakness/wasting is a relatively common clinical manifestation of AIDS. Individuals with HIV-associated myopathy or muscle weakness or wasting typically experience significant weight loss, generalized or proximal muscle weakness, tenderness, and muscle atrophy.

In one embodiment, "Hypogonadism" is a condition resulting from or characterised by abnormally decreased functional activity of the gonads, with retardation of growth and sexual development.

In some embodiments, the present invention provides a method for treating, reducing the incidence, delaying the onset or progression, or reducing and/or abrogating the symptoms associated with a wasting disease in a subject. In one embodiment, the method comprises administering to a subject a composition comprising a compound of this invention and anti-cancer agent, an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, vitamins, or a combination thereof. In some embodiments, wasting diseases comprise muscle injury, bed rest, immobility, nerve injury, neuropathy, diabetic neuropathy, alcoholic neuropathy, subacute combined degeneration of the spinal cord, diabetes, rheumatoid arthritis, motor neurone diseases, Duchenne muscular dystrophy, carpal tunnel syndrome, chronic infection, tuberculosis, Addison's disease, adult SMA, limb muscle atrophy, alcoholic neuropathy, anorexia, anorexia nervosa, anorexia associated with cachexia, anorexia associated with aging, back tumour, dermatomyositis, hip cancer, inclusion body myositis, incontinentia pigmenti, intercostal neuralgia, juvenile rheumatoid arthritis, Legg-Calve-Perthes disease, muscle atrophy, multifocal motor neuropathy, nephrotic syndrome, osteogenesis imperfecta, post-polio syndrome, rib tumor, spinal muscular atrophy, reflex sympathetic dystrophy syndrome, or Tay-Sachs.

A wasting condition or disorder is defined herein as a condition or disorder that is characterized, at least in part, by an abnormal, progressive loss of body, organ or tissue mass.

A wasting condition can occur as a result of a pathology such as, for example, cancer, or it can be due to a physiologic or metabolic state, such as disuse deconditioning that can occur, for example, due to prolonged bed rest or when a limb is immobilized, such as in a cast, or with the occurrence of multiple wounds, including, for example, amputation, as occurs in diabetics, and other conditions, as will be appreciated by one skilled in the art. A wasting condition can also be age associated. The loss of body mass that occurs during a wasting condition can be characterized by a loss of total body weight, or a loss of organ weight such as a loss of bone or muscle mass due to a decrease in tissue protein.

In one embodiment, the terms "muscle wasting" or "muscular wasting", refer to the progressive loss of muscle mass and/or to the progressive weakening and degeneration of muscles, including the skeletal or voluntary muscles which control movement, cardiac muscles which control the heart, and smooth muscles. In one embodiment, the muscle wasting condition or disorder is a chronic muscle wasting condition or disorder. "Chronic muscle wasting" is defined herein as the chronic (i.e. persisting over a long period of time) progressive loss of muscle mass and/or to the chronic progressive weakening and degeneration of muscle.

The loss of muscle mass that occurs during muscle wasting can be characterized by a muscle protein breakdown or degradation, by muscle protein catabolism. Protein catabolism occurs because of an unusually high rate of protein degradation, an unusually low rate of protein synthesis, or a combination of both. Protein catabolism or depletion, whether caused by a high degree of protein degradation or a low degree of protein synthesis, leads to a decrease in muscle mass and to muscle wasting. The term "catabolism" has its commonly known meaning in the art, specifically an energy burning form of metabolism.

Muscle wasting can occur as a result of pathology, disease, condition or disorders, including disorders for treatment via the methods of this invention, such as, for example, end stage renal failure.

In one embodiment, the wasting disease is cachexia or involuntary weight loss in a subject. In another embodiment, the present invention provides a method of treating, preventing, inhibiting, reducing or suppressing muscle wasting in a subject suffering from a kidney disease. In one embodiment, the present invention provides a method of treating, preventing, inhibiting, reducing or suppressing protein catabolism in a subject suffering from a kidney disease or disorder, In some embodiments, the present invention provides a method for treating, reducing the incidence, delaying the onset or progression, or reducing and/or abrogating the symptoms associated with a hypogonadal state in a subject. In one embodiment, the present invention provides a method for treating, reducing the incidence, delaying the onset or progression, or reducing and/or abrogating the symptoms associated with a pharmacotherapy induced hypogonadal state in a subject. In some embodiments, hypogonadism is caused by treatments which alter the secretion of hormones from the sex glands in both women and men. In some embodiments, hypogonadism may be "primary" or "central". In primary hypogonadism, the ovaries or testes themselves do not function properly. In some embodiments, hypogonadism may be induced by surgery, radiation, genetic and developmental disorders, liver and kidney disease, infection, or certain autoimmune disorders. In some embodiments, menopause is a form of hypogonadism.

In some embodiments, the present invention provides a method for treating, reducing the incidence, delaying the onset or progression, or reducing and/or abrogating the symptoms associated with a combination of diseases and/or disorders in a subject as described hereinabove. In one embodiment, the method comprises administering to a subject a composition comprising a compound of this invention and an anti-cancer agent, an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, an agent treating a dermatological disorder, an anti-infective agent, an agent treating the liver, an agent treating the kidney, vitamins, or a combination thereof.

It is to be understood that any method of this invention, as herein described, encompasses the administration of a compound as herein described, or a composition comprising the same, to the subject, in order to treat the indicated disease, disorder or condition. The methods as herein described each and/or all may further comprise administration of an additional therapeutic agent as herein described, and as will be appreciated by one skilled in the art.

In some embodiments, the present invention provides a method for enhanced production such as milk, sperm, or egg. In some embodiments, the present invention provides a method for enhanced production of lean meats or eggs. In some embodiments, the present invention provides a method for increased productivity of feeds or stud livestock, for example, increased sperm count, improved morphology of sperm, etc. In some embodiments, the present invention provides a method for expanding the productive life of farm animals, for example, egg-laying hens, milk-producing cows, etc, and/or enhanced herd health, for example, improved immune clearance, stronger animals.

In another embodiment, the compounds of this invention and compositions as described herein are useful in promoting or speeding recovery following a surgical procedure.

In one embodiment, the present invention provides a use of a compound as described herein for reducing a fat mass in a subject. In another embodiment the invention provides such methods for use of the compound as described herein or its prodrug, analog, isomer, metabolite, derivative, pharmaceutically acceptable salt, pharmaceutical product, polymorph, crystal, impurity, N-oxide, hydrate or any combination thereof, or a composition comprising the same.

In one embodiment, the present invention provides a use of a compound as described herein for increasing a lean mass in a subject. In another embodiment such use comprises administration of a compound as described herein or its prodrug, analog, isomer, metabolite, derivative, pharmaceutically acceptable salt, pharmaceutical product, polymorph, crystal, impurity, N-oxide, hydrate or any combination thereof.

In one embodiment the subject has a hormonal imbalance, disorder, or disease. In another embodiment the subject has menopause.

Example 4 demonstrates that a compound of formula (S-II) is anabolic yet minimally androgenic, thus such compounds may be useful in treating patient groups in which androgens were contraindicated in the past. Compound of formula (S-II) was shown to stimulate muscle growth, whether in the presence or absence of testosterone while exerting anti-proliferative effects on the prostate, thus, in one embodiment, the methods of this invention provide for restoring lost muscle mass in patients with sarcopenia or cachexia.

In one embodiment, the compounds as herein described alter the levels of leptin in a subject. In another embodiment, the compounds as herein described decrease the levels of leptin. In another embodiment, the compounds as herein described increase the levels of leptin in a subject. Leptin is known to have an effect on appetite or weight loss in obese mice, and thus has been implicated in obesity.

The compounds as herein described, in one embodiment, affect circulating, or in another embodiment, tissue levels of leptin. In one embodiment, the term 'level/s of leptin' refers to the serum level of leptin. As contemplated herein, the compounds of the present invention have an effect on leptin in vitro and in vivo. Leptin levels can be measured by methods known to one skilled in the art, for example by commercially available ELISA kits. In addition, leptin levels may be determined in in vitro assays, or in in vivo assays, by any method known to a person skilled in the art.

Since leptin is implicated in controlling appetite, weight loss, food intake, and energy expenditure, modulating and/or controlling the levels of leptin is a useful therapeutic approach in treating, preventing, inhibiting or reducing the incidence of obesity in subjects suffering from obesity. Modulating the level of leptin can result in a loss of appetite, a reduction of food intake, and an increase in energy expenditure in the subject, and thus may contribute to the control and treatment of obesity.

The term "obesity" is defined, in one embodiment, as an increase in body weight beyond the limitation of skeletal and physical requirement, as the result of excessive accumulation of fat in the body.

The term "obesity-associated metabolic disorder" refers, in one embodiment, to a disorder which results from, is a consequence of, is exacerbated by or is secondary to obesity. Non-limiting examples of such a disorder are osteoarthritis, type II diabetes mellitus, increased blood pressure, stroke, and heart disease.

In addition, androgens have recently been shown to be involved in commitment of mesenchymal pluripotent cells into myogenic lineage and to block differentiation into adipogenic lineage (Singh et al., Endocrinology, 2003, Jul. 24). Accordingly, the compounds can be useful in methods of blocking adipogenesis, and/or altering stem cell differentiation, as described herein.

In another embodiment, this invention relates to a method of decreasing, suppressing, inhibiting or reducing appetite of a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to decrease, suppress, inhibit or reduce the appetite of the subject.

In another embodiment, this invention relates to a method of altering the body composition of a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to alter the body composition of the subject. In one embodiment, altering the body composition comprises altering the lean body mass, the fat free body mass of the subject, or a combination thereof.

In another embodiment, this invention relates to a method of altering lean body mass or fat free body mass of a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to alter the lean body mass or fat free body mass of the subject.

In another embodiment, this invention relates to a method of converting fat to lean muscle in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to convert fat to lean muscle in the subject. In another embodiment, this invention relates to a method of converting fat to lean muscle in a subject suffering from a wasting disorder. In another embodiment, this invention relates to a method of converting fat to lean muscle in a subject suffering from a wasting disorder wherein the wasting disorder is a muscular dystrophy. In another embodiment, this invention relates to a method of converting fat to lean muscle in a subject suffering from a wasting disorder wherein the wasting disorder is Duchenne muscular dystrophy.

It is to be understood that any use of any of the compounds as herein described may be used in the treatment of any disease, disorder or condition as described herein, and represents an embodiment of this invention.

The following examples are presented in order to more fully illustrate the preferred embodiments of the invention. They should in no way, however, be construed as limiting the broad scope of the invention.

EXAMPLES

Example 1

Synthesis of (S) Enantiomer of Compound of Formula II (S-II)

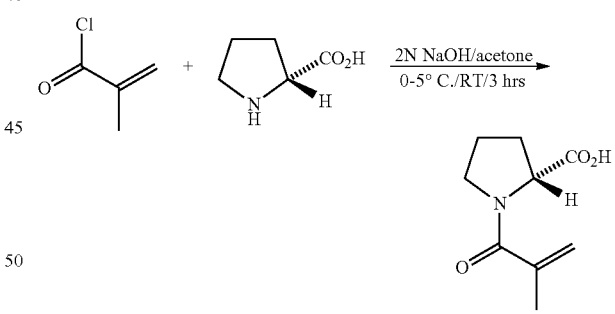

(2R)-1-Methacryloylpyrrolidin-2-carboxylic Acid

D-Proline, 14.93 g, 0.13 mol) was dissolved in 71 mL of 2 N NaOH and cooled in an ice bath; the resulting alkaline solution was diluted with acetone (71 mL). An acetone solution (71 mL) of methacryloyl chloride (13.56 g, 0.13 mol) and 2 N NaOH solution (71 mL) were simultaneously added over 40 min to the aqueous solution of D-proline in an ice bath. The pH of the mixture was kept at 10-11° C. during the addition of the methacryloyl chloride. After stirring (3 h, room temperature), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over $Na_2SO_4$, filtered through Celite®, and evaporated in vacuo to give the crude product as a colorless oil. Recrystallization of the oil from ethyl ether and hexanes afforded 16.2 g (68%) of the desired compound as colorless crystals: mp 102-103° C. (lit. mp 102.5-103.5° C.); the NMR spectrum of this compound demonstrated the existence of two rotamers of the title compound. $^1$H NMR (300 MHz, DMSO-$d_6$) δ 5.28 (s) and 5.15 (s) for the first rotamer, 5.15 (s) and 5.03 (s) for the second rotamer (totally 2H for both rotamers, vinyl $CH_2$), 4.48-4.44 for the first rotamer, 4.24-4.20 (m) for the second rotamer (totally 1H for both rotamers, CH at the chiral canter), 3.57-3.38 (m, 2H, $CH_2$), 2.27-2.12 (1H, CH), 1.97-1.72 (m, 6H, $CH_2$, CH, Me); $^{13}$C NMR (75 MHz, DMSO-$d_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 cm$^{-1}$; $[α]_D^{26}$ +80.8° (c=1, MeOH); Anal. Calcd. for $C_9H_{13}NO_3$: C, 59.00; H, 7.15; N, 7.65. Found: C, 59.13; H, 7.19; N, 7.61.

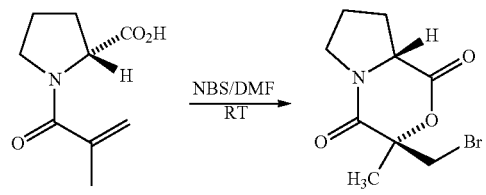

(3R,8aR)-3-Bromomethyl-3-methyl-tetrahydro-pyrrolo[2,1-c][1,4]oxazine-1,4-dione

A solution of NBS (23.5 g, 0.132 mol) in 100 mL of DMF was added dropwise to a stirred solution of the (methylacryloyl)-pyrrolidine (16.1 g, 88 mmol) in 70 mL of DMF under argon at room temperature, and the resulting mixture was stirred 3 days. The solvent was removed in vacuo, and a yellow solid was precipitated. The solid was suspended in water, stirred overnight at room temperature, filtered, and dried to give 18.6 g (81%) (smaller weight when dried ~34%) of the title compound as a yellow solid: mp 152-154° C.; $^1$H NMR (300 MHz, DMSO-$d_6$) δ 4.69 (dd, J=9.6 Hz, J=6.7 Hz, 1H, CH at the chiral center), 4.02 (d, J=11.4 Hz, 1H, $CHH_a$), 3.86 (d, J=11.4 Hz, 1H, $CHH_b$), 3.53-3.24 (m, 4H, $CH_2$), 2.30-2.20 (m, 1H, CH), 2.04-1.72 (m, 3H, $CH_2$ and CH), 1.56 (s, 2H, Me); $^{13}$C NMR (75 MHz, DMSO-$d_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; $[α]_D^{26}$ +124.5° (c=1.3, chloroform); Anal. Calcd. for $C_9H_{12}BrNO_3$: C, 41.24; H, 4.61; N, 5.34. Found: C, 41.46; H, 4.64; N, 5.32.

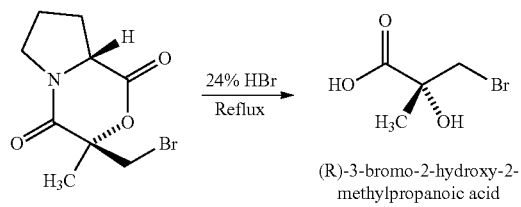

(2R)-3-Bromo-2-hydroxy-2-methylpropanoic Acid

A mixture of bromolactone (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated $NaHCO_3$ (100 mL×4). The aqueous solution was acidified with concentrated HCl to pH=1, which, in turn, was extracted with ethyl acetate (100 mL×4). The combined organic solution was dried over $Na_2SO_4$, filtered through Celite®, and evaporated in vacuo to dryness. Recrystallization from toluene afforded 10.2 g (86%) of the desired compound as colorless crystals: mp 107-109° C.; $^1$H NMR (300 MHz, DMSO-$d_6$) δ 3.63 (d, J=10.1 Hz, 1H, $CHH_a$), 3.52 (d, J=10.1 Hz, 1H, $CHH_b$), 1.35 (s, 3H, Me); IR (KBr) 3434 (OH), 3300-2500 (COOH), 1730 (C=O), 1449, 1421, 1380, 1292, 1193, 1085 cm$^{-1}$; $[α]_D^{26}$ +10.5° (c=2.6, MeOH); Anal. Calcd. for $C_4H_7BrO_3$: C, 26.25; H, 3.86. Found: C, 26.28; H, 3.75.

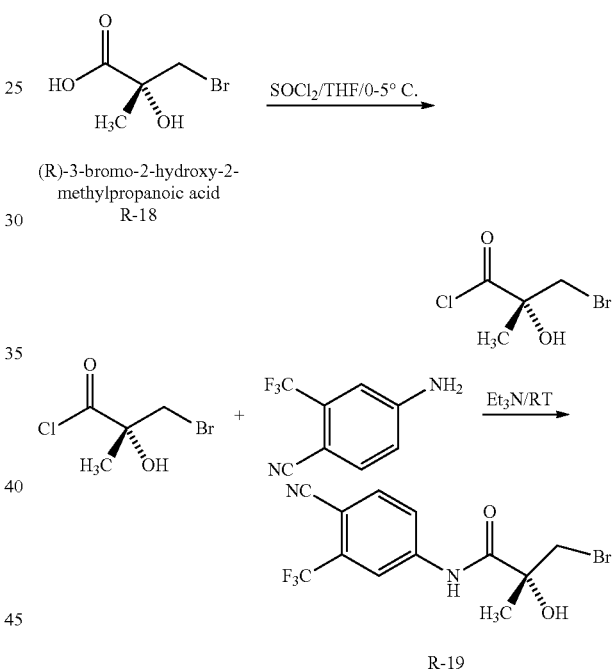

Synthesis of (2R)-3-Bromo-N-[4-cyano-3-(trifluoromethyl)phenyl]-2-hydroxy-2-methylpropanamide Thionyl chloride (46.02 g, 0.39 mol) was added dropwise to a cooled solution (less than 4° C.) of R-18 (51.13 g, 0.28 mol) in 300 mL of THF under an argon atmosphere. The resulting mixture was stirred for 3 h under the same condition. To this was added $Et_3N$ (39.14 g, 0.39 mol) and stirred for 20 min under the same condition. After 20 min, 5-amino-2-cyanobenzotrifluoride (40.0 g, 0.21 mol), 400 mL of THF were added and then the mixture was allowed to stir overnight at room temperature. The solvent was removed under reduced pressure to give a solid which was treated with 300 mL of $H_2O$, extracted with EtOAc (2×400 mL). The combined organic extracts were washed with saturated $NaHCO_3$ solution (2×300 mL) and brine (300 mL). The organic layer was dried over $MgSO_4$ and concentrated under reduced pressure to give a solid, which was purified from column chromatography using CH$_2$Cl$_2$/EtOAc (80:20) to give a solid. This solid was recrystallized from CH$_2$Cl$_2$/hexane to give 55.8 g (73.9%) of (2R)-3-bromo-N-[4-cyano-3-(trifluoromethyl)phenyl]-2-hydroxy-2-methylpropanamide (R-19) as a light-yellow solid.

$^1$H NMR (CDCl$_3$/TMS) δ 1.66 (s, 3H, CH$_3$), 3.11 (s, 1H, OH), 3.63 (d, J=10.8 Hz, 1H, CH$_2$), 4.05 (d, J=10.8 Hz, 1H, CH$_2$), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). Calculated Mass: 349.99, [M–H]$^-$ 349.0. M.p.: 124-126° C.

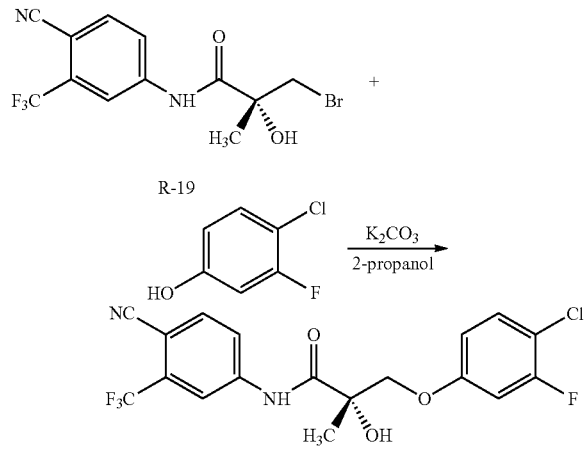

Synthesis of (S)-3-(4-chloro-3-fluorophenoxy)-N-(4-cyano-3-(trifluoromethyl)phenyl)-2-hydroxy-2-methylpropanamide A mixture of bromoamide ((2R)-3-bromo-N-[4-cyano-3-(trifluoromethyl)phenyl]-2-hydroxy-2-methylpropanamide, (R-19) 2.0 g, 5.70 mmol) and anhydrous K$_2$CO$_3$ (2.4 g, 17.1 mmol) was heated to reflux for 2 h and then concentrated under reduced pressure to give a solid. The resulting solid was treated with 4-chloro-3-fluorophenol (1.3 g, 8.5 mmol) and anhydrous K$_2$CO$_3$ (1.6 g, 11.4 mmol) in 50 mL of 2-propanol and was heated to reflux for 3 h, then concentrated under reduced pressure to give a solid. The residue was treated with 100 mL of H$_2$O and then extracted with EtOAc (2×100 mL). The combined EtOAc extracts were washed with 10% NaOH (4×100 mL) and brine, successively. The organic layer was dried over MgSO$_4$ and then concentrated under reduced pressure to give an oil which was purified by column chromatography using EtOAc/hexane (50:50) to give a solid which was recrystallized from CH$_2$Cl$_2$/hexane to give 1.7 g (70.5%) of (S)-3-(4-chloro-3-fluorophenoxy)-N-(4-cyano-3-(trifluoromethyl)phenyl)-2-hydroxy-2-methylpropanamide as a colorless solid.

$^1$H NMR (CDCl$_3$/TMS) δ 1.60 (s, 3H, CH$_3$), 3.28 (s, 1H, OH), 3.98 (d, J=9.05 Hz, 1H, CH), 6.64-6.76 (m, 2H, ArH), 7.30 (d, J=8.67 Hz, 1H, ArH), 7.81 (d, J=8.52 Hz, 1H, ArH), 7.96 (q, J=2.07, 8.52 Hz, 1H, ArH), 8.10 (d, J=2.07 Hz, 1H, ArH), 9.10 (s, 1H, NH). Calculated Mass: [M–H]$^+$ 414.9. Mp: 132-134° C.

Example 2

Metabolic Stability of the Compounds of this Invention

Metabolic stability assays were performed in order to assess the in vitro half-life of the S-isomer of the compound of formula II (S-II) when incubated with human liver microsomes. The data generated was transformed to determine intrinsic clearance values. In a separate experiment, permeability across human, intestinal epithelial monolayers (Caco-2 cells) was used as a measure of intestinal permeability as well as an indicator of efflux potential. Caco-2 cells are often used as an early screening surrogate for oral bioavailability. Microsomal half-life can be converted to in vitro clearance values as a means to predict hepatic intrinsic clearance. Intrinsic clearance is defined as the functional ability of the liver to metabolize a drug or other compound.

Materials and Methods:

Metabolic Stability Measured in Human Liver Microsomes:

Compound of formula S-II in this study was incubated at a final concentration of 0.6 μM. Microsome reactions were performed under either Phase I or "Phase I and II" conditions, where indicated. Compound stocks (10 mM ACN) were initially diluted to a concentration of 60 μM (in 60% ACN/H$_2$O) resulting in a "working stock" solution of 100×. Human liver microsomes were utilized at a final concentration of 0.6 mg/ml. Duplicate wells were used for each time point (0, 6, 10, 30, and 60 minutes). Reactions were carried out at 37° C. in a shaking water bath, and the final concentration of solvent was kept constant at 0.6%. The final volume for each reaction was 600 μl, comprised of 368 μl of 100 mM KPO$_4$ buffer, (pH 7.4); 12.6 μl of HLM (from a 20 mg/ml stock); 6 μl of 100× "working stock" drug compound, and 126 μl of NRS "master mix" solution. At each time point, 100 μl of reaction was removed and added to a sample well containing 100 μl of ice-cold, 100% ACN (plus internal standards), to stop the reaction. The NRS "master mix" is a solution of glucose-6-phosphate dehydrogenase, NADP$^+$, MgCl$_2$, and glucose-6-phosphate, prepared per manufacturer's instructions (BD Biosciences, Waltham, Mass.). Each 6.0 ml stock of NRS "master mix" solution contains 3.8 ml H$_2$O, 1.0 ml solution "A" (Cat. #461220), and 0.2 ml solution "B" (Cat. #461200). Human liver microsomes (lot #0610279, Xenotech Corp.) represented a pool of 60 donors.

Samples were centrifuged at 3,000 rpm for 10 minutes at 4° C. to remove debris and precipitate protein. Approximately 160 μl of supernatant was subsequently transferred to a new sample block for analysis. The concentration of parent drug remaining in each well (expressed as percent remaining versus Time '0', at the beginning of the reaction) was measured by LC/MS, as detailed below. The intrinsic clearance rates (CL$_{int}$) were calculated from 0-60 minutes based on first order decay kinetics as a function of microsomal protein concentration.

Permeability Across Human, Intestinal Epithelial Monolayers:

Permeability was measured in the Apical (pH 6.6) to Basolateral (pH 7.4) and Basolateral (pH 7.4) to Apical (pH 6.6) directions across polarized, Caco-2 epithelial monolayers. Compound stocks (10 mM acetonitrile) were tested in the study at a final concentration of 10 μM. The concentration of drug in the receiver well was measured by LC/MS/MS using a standard curve. The apparent permeability (P$_{app}$) for each compound was calculated, and values (A-B) were classified as: Poor (P$_{app}$: <1), Low (P$_{app}$ 1-2), Medium (P$_{app}$ 2-10) or High (P$_{app}$>10).

$$P_{app}(\times 10^{-6}\ cm/sec) = \text{Amount transported}/(\text{Area}*\text{Initial concentration}*\text{Time})$$

$$P_{app}(cm/s) = [V/(A*Ci)]*(Cf/T)$$

V=volume of the receptor chamber (ml, or cm$^3$)
A=area of the membrane insert (cm$^2$)

Ci=initial concentration of drug (µM)
Cf=final concentration of drug (µM)
T=assay time (seconds)
Analytical Methods:

All samples were analyzed on the MDS/Sciex API4000 Q Trap system with electrospray ionization (ESI) in the positive or negative SIM mode, depending on the compounds. The mobile phases were isocratic at 30% A (0.1% formic acid in water) and 70% B (0.1% formic acid in acetonitrile) with a flow rate of 0.4 mL/min. A Phenomenex Luna Phenyl-Hexyl column (60×2.0 mm ID, 6µ) was used. The injection volume was 10 µL. The total run time per sample was 1.6 to 3.0 minutes. Tamoxifen and diclofenac were used as internal standards for the positive and negative mode, respectively. The percentage of parent drug compound remaining after each time point was determined relative to the initial measured concentration at the beginning of the reaction ($T_0$ min).

Data Analysis:

For half-life determination, data was fitted using GraphPad Prism, v 4.03 with the non-linear regression equation "one phase exponential decay" defined as:

$$Y = Span*exp(-K*X) + Plateau \text{(decays to Plateau with a first-order rate constant, } K\text{)}.$$

"-K" is the slope of the curve. The half life (minutes), $T_{1/2}$, =ln 2/-K and is therefore defined as –0.693/K, a.k.a. –0.693/slope). Intrinsic Clearance (µl/min/mg protein) is defined as: $CL_{int} = 0.693*(1/T_{1/2})*(\text{ml incubation/mg protein})*1000$; This equation can also be expressed as (K*1000)/microsome concentration.

Results:

TABLE 1

Metabolic Stability Measured in Human Liver Microsomes:

| Compound having formula | Half Life (minutes) Phase I only | $CL_{int}$ (µl/min/mg) Phase I only | Half Life (minutes) Phase I + II | $CL_{int}$ (µl/min/mg) Phase I + II |
| --- | --- | --- | --- | --- |
| S-II | Stable | <1 | Stable | <1 |

The results had shown that in vitro half-life as determined from the microsomal assays demonstrated that compound of formula S-II under both phase I and phase I/II metabolic conditions. As shown in Table 1, the compound did not exhibit an intrinsic clearance ($CL_{int}$) value greater than 10 µl/min/mg. It is generally accepted that an in vitro $CL_{int}$ value of less than 10 µl/min/mg protein represents favorable metabolic stability of the test compound. Compound of formula S-II exhibited low clearance in human liver microsomes. In conclusion, based on the data reported herein, compound of formula S-II exhibited favorable metabolic stability profiles in vivo studies.

Example 3

Androgen Receptor Binding Affinity of SARMs

Materials and Methods:

The androgen receptor (AR) binding affinity of SARMs was determined by using an in vitro competitive radioligand binding assay with [17α-methyl-$^3$H]-mibolerone ([$^3$H]MIB, PerkinElmer), a high affinity AR ligand. Recombinant androgen receptor ligand binding domain (AR LBD) was combined with [$^3$H]MIB in buffer A (10 mM Tris, pH 7.4, 1.6 mM disodium EDTA, 0.26 M sucrose, 10 mM sodium molybdate, 1 mM PMSF) to determine the equilibrium dissociation constant ($K_d$) of [$^3$H]MIB. Protein was incubated with increasing concentrations of [$^3$H]MIB with and without a high concentration of unlabeled MIB in order to determine total and non-specific binding. Non-specific binding was then subtracted from total binding to determine specific binding and graphed using SigmaPlot and non-linear regression for ligand binding curve with one site saturation to determine the $K_d$ of MIB (1.84 nM). In addition, the concentration of [$^3$H]MIB required to saturate AR LBD was determined to be 4 nM.

Compound of formula S-II was tested in a range of concentrations from $10^{-11}$ to $10^{-6}$ M using the conditions described above. Following incubation, plates were harvested with GF/B filters on the Unifilter-96 Harvester (PerkinElmer) and washed three times with ice-cold buffer B (60 mM Tris, pH 7.2). The filter plates were dried at RT, then 36 µl Microscint-O cocktail was added to each well and sealed with TopSeal-A. The receptor bound radioligand was then determined with the TopCount® NXT Microplate Scintillation Counter (PerkinElmer).

The specific binding of [$^3$H]MIB at each concentration of SARM was determined by subtracting the nonspecific binding of [$^3$H]MIB (determined by incubating with $10^{-6}$ M unlabeled MIB), and expressed as a percentage of the specific binding in the absence of each SARM. The concentration of SARM required to decrease the [$^3$H]MIB binding by 60%, $IC_{60}$ value, was determined by computer-fitting the data with SigmaPlot and non-linear regression with the standard curve four parameter logistic curve. The equilibrium binding constant ($K_i$) of each compound was then determined with the following equation:

$$K_i = K_d \times IC_{60}/(K_d + L)$$

where $K_d$ is the equilibrium dissociation constant of [$^3$H]MIB (1.84 nM), and L is the concentration of [$^3$H]MIB (4 nM).

Results:

The binding affinity for compound of formula S-II was tested in the radioligand binding assay with AR LBD as the receptor with $K_i$ (nM)=8.1.

Example 4

Preclinical Anabolic and Androgenic Pharmacology of Compound of Formula S-II in Intact and Castrate Male Rats Anabolic and androgenic efficacy of compound of formula S-II administered by daily oral gavage was tested. The S-isomer of compound of formula II was synthesized and tested as described herein.

Materials and Methods:

Male Sprague-Dawley rats weighing approximately 200 g were purchased from Harlan Bioproducts for Science (Indianapolis, Ind.). The animals were maintained on a 12-h light/dark cycle with food (7012C LM-485 Mouse/Rat Sterilizable Diet, Harlan Teklad, Madison, Wis.) and water available ad libitum. The animal protocol was reviewed and approved. The anabolic and androgenic activity of the compound of formula S-II was studied in intact animals, acutely orchidectomized (ORX) animals and chronically (9 days) ORX rats.

The test article for this study was weighed and dissolved in 10% DMSO (Fisher) diluted with PEG 300 (Acros Organics, NJ) for preparation of the appropriate dosage concentrations. The animals were housed in groups of 2 to 3 animals per cage. Animals were randomly assigned to one of seven groups consisting of 4 to 5 animals per group. Control groups (intact and ORX) were administered vehicle daily. Compound of formula S-II was administered via oral gavage at doses of 0.01, 0.03, 0.1, 0.3, 0.75, and 1 mg/day to both intact and ORX groups. Where appropriate, animals were castrated on day one of the study. Treatment with compound of formula S-II began nine days post ORX and was administered daily via oral gavage for fourteen days.

The animals were sacrificed under anesthesia (ketamine/xyalzine, 87:13 mg/kg) and body weights were recorded. In addition, ventral prostate, seminal vesicles, and levator ani muscle were removed, individually weighed, normalized to body weight, and expressed as a percentage of intact control. Student's T-test was used to compare individual dose groups to the intact control group. Significance was defined a priori as a P-value<0.05. Ventral prostate and seminal vesicle weights were evaluated as a measure of androgenic activity, whereas levator ani muscle weight was evaluated as a measure of anabolic activity. Blood was collected from the abdominal aorta, centrifuged, and sera were frozen at −80° C. prior to determination of serum hormone levels. Serum luteinizing hormone (LH) and follicle stimulating hormone (FSH) concentrations were determined.

Results:

A series of dose-response studies in intact and castrated rats in order to evaluate the potency and efficacy of compound of formula S-II in both androgenic (prostate and seminal vesicles) and anabolic (levator ani muscle) tissue was conducted. In intact animals, compound of formula S-II treatment resulted in decreases in the weight of both prostate and seminal vesicles while the levator ani muscle weight was significantly increased. Levator ani muscle weight following compound of formula S-II treatment were 100%±10%, 98%±7%, 110%±5%, 110%±5%, 125%±10%, and 129%±10% of intact controls following doses of 0.01, 0.03, 0.1, 0.3, 0.75, and 1 mg/day, respectively. The prostate weights were 117%±20%, 98%±15%, 82%±20%, 62%±5%, 107%±30%, and 110%±14% of intact controls following doses of 0.01, 0.03, 0.1, 0.3, 0.75, and 1 mg/day, respectively. These results are significant since current androgen therapies are contraindicated in some patient populations due to the proliferative androgenic effects in prostate and breast tissues. However, many patients in these populations could benefit from the anabolic actions of androgens in muscle and bone. Since compound of formula (S-II) exhibited tissue selective anabolic effects, it may be possible to treat patient groups in which androgens were contraindicated in the past.

Figure 2:
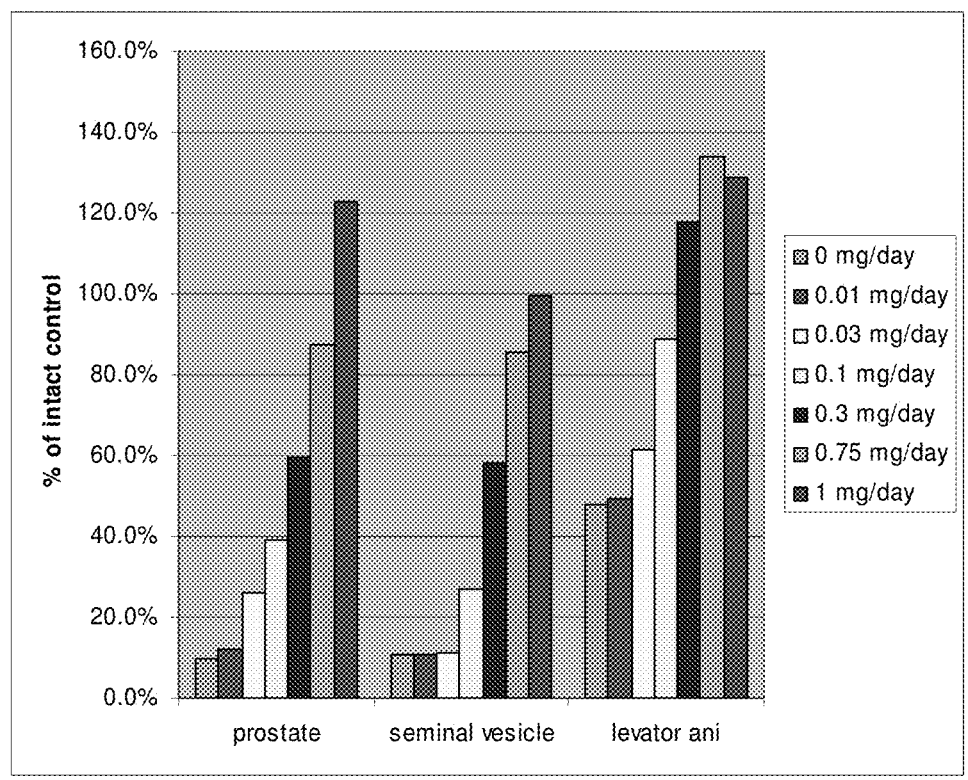
FIG. 2: Anabolic and androgenic pharmacology of compound of formula S-II in castrated rats (ORX).

In castrated, ORX animals, prostate weights following compound of formula S-II treatment were 10%±3%, 12%±3%, 26%±7%, 39%±6%, 60%±14%, 88%±16%, and 123%±22% of intact controls following doses of 0, 0.01, 0.03, 0.1, 0.3, 0.75, and 1 mg/day, respectively (FIG. 2). Similarly, seminal vesicle weights were 11%±1%, 11%±1%, 11%±1%, 27%±14%, 58%±18%, 86%±12%, and 100%±8% of intact controls following doses of 0, 0.01, 0.03, 0.1, 0.3, 0.75, and 1 mg/day, respectively (FIG. 2). Significant increases were seen in levator ani muscle weights in all dose groups, when compared to intact controls. The levator ani muscle weights were 48%±8%, 50%±5%, 62%±6%, 89%±10%, 118%±6%, 134%±8% and 129%±14% of intact controls corresponding to 0, 0.01, 0.03, 0.1, 0.3, 0.75, and 1.0 mg/day dose groups, respectively (FIG. 2).

Testosterone propionate (TP) and S-3-(4-acetylaminophenoxy)-2-hydroxy-2-methyl-N-(4-nitro-3-trifluoromethylphenyl)propionamide (S-4), maximally stimulated the levator ani muscle weight to 104% and 101%, respectively. These data show that compound of formula S-II exhibited significantly greater efficacy and potency than either TP or S-4. As a whole, these data show that compound of formula S-II is able to stimulate muscle growth in the presence or absence of testosterone while exerting anti-proliferative effects on the prostate. These data show that that compound of formula S-II restores lost muscle mass in patients with sarcopenia or cachexia. Additionally, the antiproliferative effects of compound of formula S-II on the prostate may allow some patient populations, in which androgens are currently contraindicated, access to anabolic agents.

Compound of formula S-II exhibited anabolic muscle/prostate ratio in castrated rats of 4.10, 2.39, 2.28, 1.97, 1.53, and 1.05 following doses of 0.01, 0.03, 0.1, 0.3, 0.75 and 1 mg/day, respectively.

Pharmacology results following 1 mg/day of compound of formula S-II exhibited that prostate weight was 110%±14% of intact control and levator ani muscle weight was 129%±10% of intact control. Compound of formula S-II maintained prostate weight following orchidectomy at 123±22% of intact controls and levator ani muscle weight at 129±14% of intact controls. A range of between 0.1 mg/day to 0.3 mg/day of compound of formula S-II restored 100% of levator ani muscle weight, while between 39 to 60% prostate weight was restored.

Example 5

In Vitro CYP Inhibition Assay

Materials and Methods:

P450 enzyme inhibition was measured using human cDNA-expressed CYP3A4, 2D6, 2C19, 2C9, and 1A2 recombinant enzymes and fluorogenic substrates (coumarin analogues) that are converted to fluorescent products. The analogues utilized for each isoenzyme are as follows: 7-benzyloxy-trifluoromethylcoumarin, (BFC) for 3A4; 3-[2-(N,N-diethyl-N-methyl amino)ethyl]-7-methoxy-4-methylcoumarin, (AMMC) for 2D6; 3-cyano-7-ethoxycoumarin, (CEC) for 2C19 and 1 A2; and 7-methoxy-4-trifluoromethylcoumarin, (MFC) for 2C9. These substrates were utilized at a single concentration (either 50 µM or 75 µM) at or near the apparent $K_m$ for each substrate. Fluorescence intensity was measured using a Wallac 1420 Victor$^3$ Multi-label Counter Model (Perkin-Elmer, Wellesley, Mass.), with an excitation wavelength filter of 405 nm, and an emission filter of 460 nm (535 nm for the 3A4 and 2C9 substrates). Compound stocks (10 mM in a 4:1 ratio of acetonitrile:DMSO) were tested in this study using an 8-point dose response curve in duplicate (ranging from 0.15 µM-20.0 µM). The concentration of acetonitrile was kept constant at 0.4%, and the reaction was carried out at 37° C. for 30 minutes. Averages (minus background) and $IC_{50}$ values were calculated.

Results:

The in vitro screening results for potential drug-drug interactions (DDI) of SARM compound of formula S-II is presented in Table 2:

TABLE 2

| Compound | CYP (P450) Inhibition, $IC_{50}$ (µM) | | | | |
|---|---|---|---|---|---|
| | 3A4 | 2D6 | 2C19 | 2C9 | 1A2 |
| S-II | >20 | 17.7 | 2.4 | 1.3 | >20 |

Example 6

Pharmacokinetics of Compound of Formula S-II in Dogs

In order to determine the pharmacokinetics of compound of formula S-II, the compound was administered to beagle dogs perorally, and circulating plasma levels, terminal elimination half-life ($t_{1/2}$), total body clearance (CL), terminal volume distribution (Vz) and absolute bioavailability (F %) (Table 3) were determined.

TABLE 3

|  | Compound S-II |
| --- | --- |
| $T_{1/2}$ (hr) | 37 ± 26.8 |
| CL (mL/min/kg) | 0.36 ± 0.12 |
| Vz (mL/kg) | 1266 ± 352 |
| F % | 72.5% |

Example 7

Figure 3:
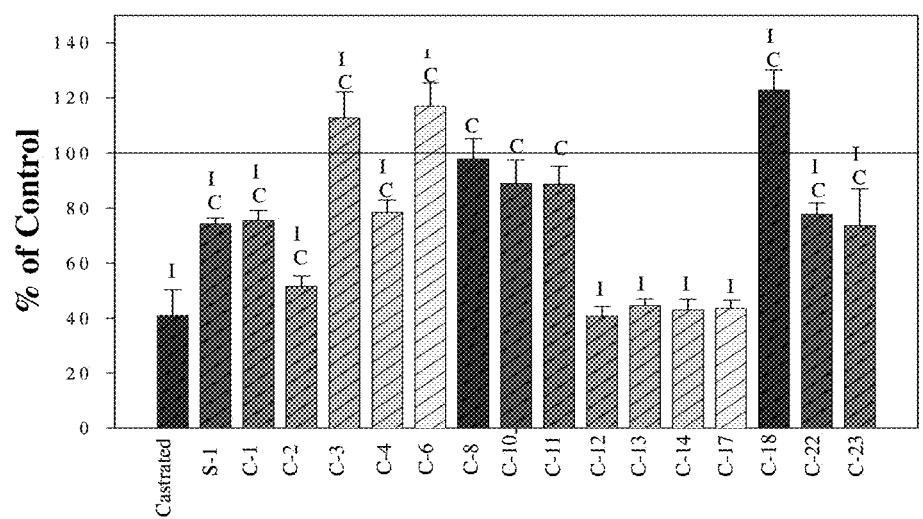
FIG. 3: Levator ani weight effects in castrated rats for a panel of compounds.
Figure 4:
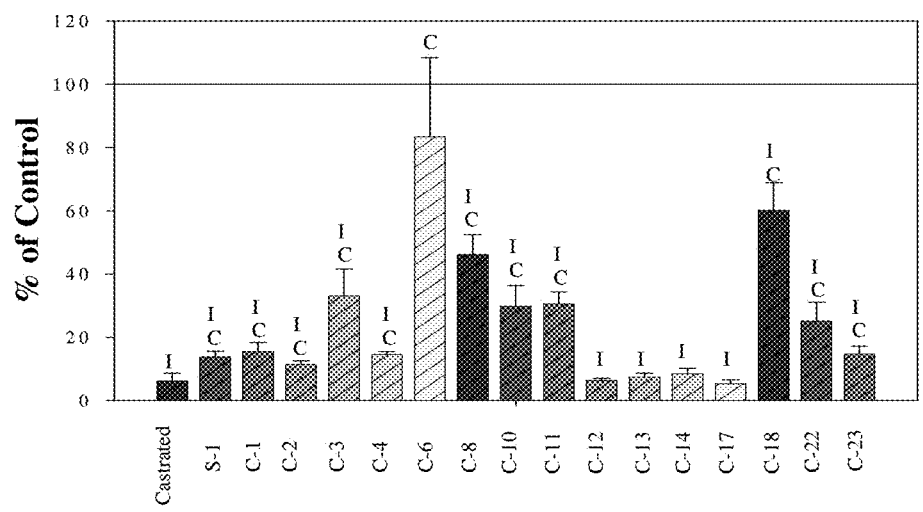
FIG. 4: Prostate weight effects in castrated rats for a panel of compounds.

Anabolic and Androgenic Activity of SARM Compounds in Intact and Castrated Male Rats The in vivo pharmacological activity of each synthetic AR ligand (listed in Table 4, below) was examined in five male Sprague-Dawley rats weighing approximately 200 g. Animals were castrated via a scrotal incision under anesthesia 24 h before drug treatments and received daily subcutaneous injections of the compound of interest at a dose rate of 1 mg/d for 14 d. All compounds of interest were freshly dissolved in vehicle containing dimethylsulfoxide (5%, vol/vol) in polyethylene glycol 300 before dose administration. An additional two groups of animals with or without castration received vehicle only and served as castrated or intact control groups, respectively. Animals were killed at the end of the treatment. Plasma samples were collected and stored at −80° C. for future use. The ventral prostate, seminal vesicles, and levator ani muscle were removed, cleared of extraneous tissue, and weighed. All organ weights were normalized to body weight and compared. The weights of prostate and seminal vesicles were used to evaluate androgenic activity, whereas the levator ani muscle weight was used as a measure of anabolic activity. Ventral prostate weights in SARM treated castrated rats were all (except C-6) statistically lowered than intact control (FIG. 4). Whereas levator ani weights in castrated rats treated with SARM: C-3, C-6, C-8, C-10, C-11, or C-18 demonstrated support of muscle weight same as or in excess of intact control (FIG. 3). Further S-1, C-1, C-4, C-22, and C-23 demonstrated levator ani agonism of >75% of intact control (FIG. 3) vs. <25% of intact control in all of these cases for ventral prostate (FIG. 4). This demonstrated tissue-selective anabolism for a variety of SARMs of this invention. The results are graphically depicted in FIGS. 3 and 4.

TABLE 4

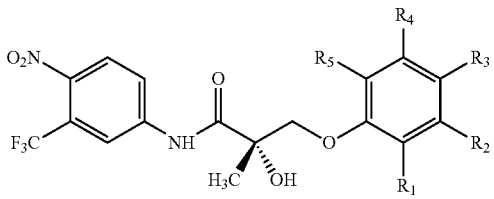

| Compound | $R_1$ | $R_2$ | $R_3$ | $R_4$ | $R_5$ |
| --- | --- | --- | --- | --- | --- |
| S-1 | H | H | F | H | H |
| C-1 | F | H | F | H | H |
| C-2 | $CH_3$ | H | F | H | H |
| C-3 | H | F | F | H | H |
| C-4 | H | Cl | F | H | H |
| C-6 | H | F | Cl | H | H |
| C-8 | F | H | Cl | H | H |
| C-10 | H | Cl | Cl | H | H |
| C-11 | H | F | $NO_2$ | H | H |
| C-12 | F | H | $NO_2$ | H | H |
| C-13 | F | F | F | H | H |
| C-14 | F | F | H | F | H |
| C-17 | F | H | F | H | F |
| C-18 | F | H | F | F | H |
| C-22 | Cl | H | Cl | Cl | H |
| C-23 | F | F | F | F | F |

Example 8

Effects of SARM Compounds on Growth Performance and Carcass Composition of Finishing Pigs Materials and Methods:

The effects of SARM as represented by compound of formula S-II on growth performance and carcass composition of finishing pigs was examined. Forty crossbred barrows, (TR4×C22) with an initial weight of 209.4 lb were used for this 28-d experiment. Pigs were blocked by weight and allotted to one of four treatments with ten replicate pens per treatment. Pigs were housed with one pig per pen in an environmentally controlled finishing barn with 4 ft×4 ft slatted pens.

All animals were fed a corn-soybean meal diet with 1% corn oil. For the treated groups, appropriate quantities of a compound of formula S-II (referred to as SARM in the text and figures/tables of this example) were dissolved in 100 mL of polysorbate (Tween®) 80 and diluted with 20 lbs of corn oil prior to incorporation into the test diet. Final SARM concentrations were 1, 3, and 10 ppm. All animals were fed their respective diets for the duration of the study. The test diets contained 1.07% TID lysine. Prior to being placed on study, all pigs were fed a common corn-soybean meal diet formulated to 0.75% TID lysine.

Pigs were allowed ad libitum access to feed and water. Pigs and feeders were weighed on day 7, 14, 21, and 28 to calculate average daily gain (ADG), average daily feed intake (ADFI), and feed-to-gain ratio (F/G or F:G). Each pen served as an experimental unit for all statistical analysis.

Pigs were slaughtered at the Kansas State University Meats Laboratory at the end of the study for collection of individual carcass data. At 24 hours postmortem, the right side of the carcass was frozen at −40° C. for approximately 1 h. After freezing, sides were ground once through a grinder equipped with a 19 mm die, then mixed and ground through a second grinder equipped with a 9.5 mm die. A sub sample of ground carcass was then chemically analyzed to determine percentages of crude protein, moisture/dry matter, lipid, and ash. Carcass measurements were done on the left side of the carcass, and a sample of lean and fat was taken from the longissimus at approximately the 10$^{th}$ rib.

The data were analyzed as a randomized complete-block design. Analysis of variance was performed by using the MIXED procedure of SAS. Linear and quadratic contrasts were used to evaluate the effects of increasing the level of the SARM on growth and carcass performance.

Figure 5B:
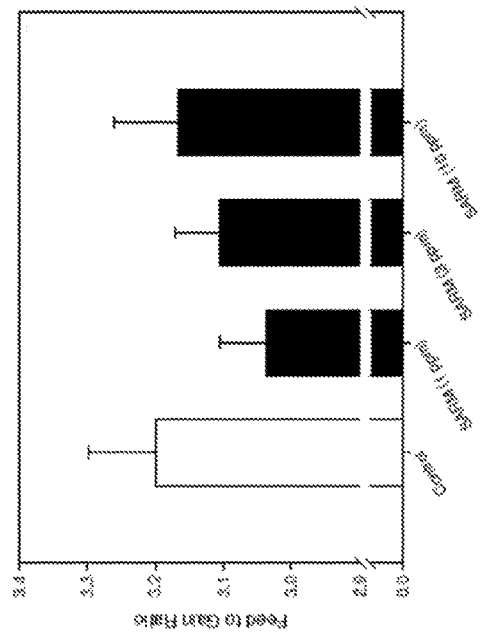
FIGS. 5A-5D: Effect of compound of formula S-II on the growth performance and carcass composition of finishing pigs.
Figure 5D:
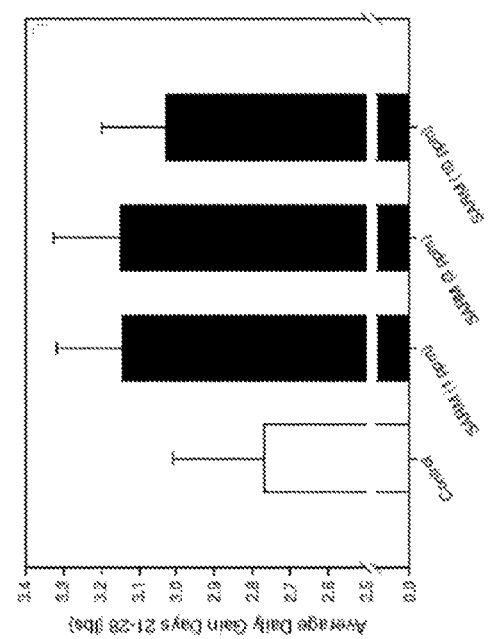
Figure 5A:
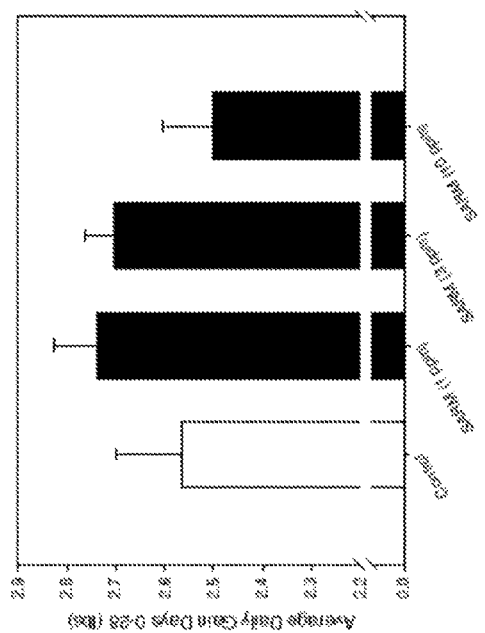
Figure 5C:
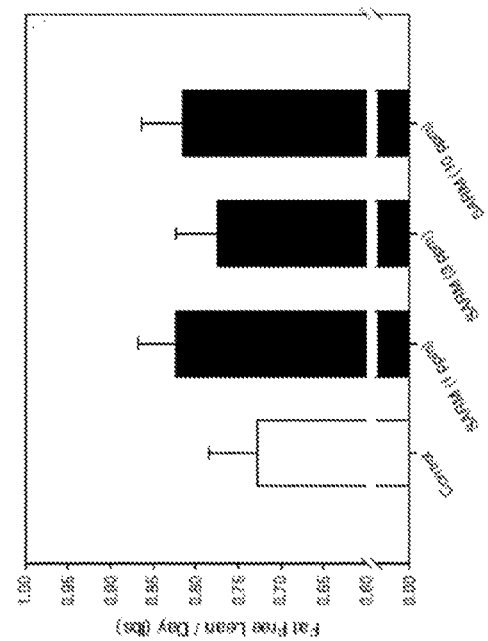

Results:

Although there were few statistical differences observed in the measured parameters due to the small group sizes and individual housing of experimental animals, we observed positive trends in several key parameters as shown in FIGS. 5A-5D. Raw data are also summarized below. SARM increased average daily gain (ADG) over the course of the study (FIG. 5A), decreased feed to gain ratio (F:G) (FIG. 5B), increased fat free lean gain per day (FIG. 5C), and dramatically increased ADG for days 21-28 (FIG. 5D).

Further, SARM treatment resulted in significantly increased Day 0-7 F:G and decreased Day 8-14 average daily feed intake (ADFI). Table 5 shows the weekly as well as the overall ADG, ADFI, and F:G data from the study.

TABLE 5

| Param-eter | | Vehicle Control | SARM, ppm | | | Probability, P< | |
|---|---|---|---|---|---|---|---|
| | | | 1 | 3 | 10 | Linear | Quadratic |
| Day 0-7 | ADG | 2.51 | 2.89 | 2.37 | 2.17 | 0.07 | 0.87 |
| | ADFI | 7.66 | 7.56 | 7.54 | 7.4 | 0.37 | 0.8 |
| | F:G | 3.24 | 2.67 | 3.27 | 3.85 | 0.05 | 0.62 |
| Day 8-14 | ADG | 2.74 | 2.59 | 2.65 | 2.37 | 0.14 | 0.94 |
| | ADFI | 8.55 | 8.74 | 8.5 | 7.89 | 0.04 | 0.67 |
| | F:G | 3.54 | 3.52 | 3.3 | 3.46 | 0.83 | 0.57 |
| Day 15-21 | ADG | 2.25 | 2.33 | 2.65 | 2.43 | 0.39 | 0.21 |
| | ADFI | 7.99 | 8.33 | 8.61 | 7.78 | 0.45 | 0.09 |
| | F:G | 3.7 | 3.88 | 3.4 | 3.33 | 0.19 | 0.71 |
| Day 22-28 | ADG | 2.77 | 3.15 | 3.15 | 3.03 | 0.92 | 0.19 |
| | ADFI | 8.19 | 8.51 | 8.89 | 8.33 | 0.79 | 0.26 |
| | F:G | 3.12 | 2.72 | 2.87 | 2.83 | 0.95 | 0.24 |
| Day 0-28 | ADG | 2.57 | 2.74 | 2.7 | 2.5 | 0.28 | 0.31 |
| | ADFI | 8.1 | 8.28 | 8.38 | 7.85 | 0.29 | 0.27 |
| | F:G | 3.2 | 3.04 | 3.11 | 3.17 | 0.56 | 0.45 |

At the time of sacrifice, a carcass composition analysis was performed. The data from this analysis are presented in Table 6. Trends towards increased lean mass and decreased fat were observed. SARM-treated pigs showed a 7 to 10% decrease in first rib fat, 3 to 8% decrease in last rib fat, 2 to 11% decrease in last lumbar fat, 6 to 14% decrease in 10$^{th}$ rib fat, and up to a 4% increase in loin eye area (LEA). Treated animals also demonstrated up to a 2% improvement in lean percent and pounds of fat free lean. However, due to the variability in this study, none of these measurements reached significance.

TABLE 6

| Parameter | Vehicle Control | SARM, ppm | | | Probability, P< | |
|---|---|---|---|---|---|---|
| | | 1 | 3 | 10 | Linear | Quadratic |
| Heart Wt, lb | 0.99 | 1.04 | 1.07 | 1.01 | 0.92 | 0.08 |
| Liver Wt, lb | 4.19 | 4.58 | 4.95 | 4.84 | 0.05 | 0.02 |
| Kidney Wt, lb | 1.08 | 1.2 | 1.18 | 1.16 | 0.38 | 0.3 |
| Dress, % | 70.3 | 69.6 | 69.3 | 70 | 0.52 | 0.23 |
| 1$^{st}$ rib fat, in | 1.59 | 1.47 | 1.48 | 1.43 | 0.21 | 0.31 |
| Last rib fat, in | 0.94 | 0.9 | 0.91 | 0.86 | 0.57 | 0.79 |
| in | 0.84 | 0.77 | 0.82 | 0.74 | 0.16 | 0.75 |
| 10$^{th}$ rib fat, in | 0.86 | 0.78 | 0.8 | 0.74 | 0.35 | 0.7 |
| LEA, in$^2$ | 7.27 | 7.26 | 7.22 | 7.59 | 0.09 | 0.41 |
| Lean, % | 52.4 | 53.2 | 52.9 | 54.3 | 0.16 | 1 |
| Fat free lean, lb | 104.2 | 106.9 | 105.5 | 106.7 | 0.46 | 0.79 |

$^a$ A total of 40 barrows were used (carcass weight of 199 lb)

Table 7 shows the complete data set for all parameters which were collected in this Example.

TABLE 7

| | Control | SARM (1 PPM) | SARM (3 PPM) | SARM (10 PPM) |
|---|---|---|---|---|
| ADG (Days 0-7) | 2.51 | 2.89 | 2.37 | 2.17 |
| ADG (Days 8-14) | 2.74 | 2.59 | 2.65 | 2.37 |
| ADG (Days 15-21) | 2.25 | 2.33 | 2.65 | 2.43 |
| ADG (Days 22-28) | 2.77 | 3.15 | 3.15 | 3.03 |
| ADG Total | 2.57 | 2.74 | 2.70 | 2.50 |
| ADFI (Days 0-7) | 7.66 | 7.56 | 7.54 | 7.40 |
| ADFI (Days 8-14) | 8.55 | 8.74 | 8.50 | 7.89 |
| ADFI (Days 15-21) | 7.99 | 8.33 | 8.61 | 7.78 |
| ADFI (Days 22-28) | 8.19 | 8.51 | 8.89 | 8.33 |
| F/G (Days 0-7) | 3.24 | 2.67 | 3.27 | 3.85 |
| F/G (Days 8-14) | 3.54 | 3.52 | 3.30 | 3.46 |
| F/G (Days 15-21) | 3.70 | 3.88 | 3.40 | 3.33 |
| F/G (Days 22-28) | 3.12 | 2.72 | 2.87 | 2.83 |
| F/G Total | 3.20 | 3.04 | 3.11 | 3.17 |
| Gain (Days 0-7) | 17.5 | 20.3 | 16.6 | 15.2 |
| Gain (Days 8-14) | 19.2 | 18.2 | 18.6 | 16.6 |
| Gain (Days 15-21) | 15.7 | 16.3 | 18.5 | 17.0 |
| Gain (Days 22-28) | 19.4 | 22.0 | 22.0 | 21.2 |
| Initial Wt | 209 | 209 | 209 | 209 |
| Live Wt | 284 | 289 | 288 | 281 |
| L side | 97.6 | 98.0 | 97.7 | 96.8 |
| R side | 101 | 103 | 102 | 99.8 |
| Carcass Wt | 199 | 201 | 200 | 197 |
| Dress % | 70% | 70% | 69% | 70% |
| 1st rib fat | 1.59 | 1.47 | 1.48 | 1.43 |
| Last rib fat | 0.935 | 0.900 | 0.905 | 0.855 |
| Last lumbar fat | 0.835 | 0.770 | 0.815 | 0.740 |
| 10th rib fat | 0.855 | 0.780 | 0.800 | 0.735 |
| LEA | 7.27 | 7.26 | 7.22 | 7.59 |
| lb FFL | 104 | 107 | 106 | 107 |
| lbs FFL/D | 0.727 | 0.822 | 0.774 | 0.814 |
| Heart Wt | 0.988 | 1.04 | 1.07 | 1.01 |
| Liver Wt | 4.19 | 4.58 | 4.95 | 4.84 |
| Kidney Wt | 1.08 | 1.20 | 1.18 | 1.16 |

The potential for using SARM (compound of formula S-II) to improve finishing characteristics in food-animals was demonstrated. Feeding the SARM greatly improved ADG and F:G while reducing carcass crude fat. Some of the greatest improvements in these parameters were noted as the lowest dose (1 ppm). Lesser effects at high dose have been observed with other SARMs. Taken as a whole, these data support that SARM treatment would improve carcass composition and growth performance which are key factors in the economics of swine production.

Example 9

Effects of SARM Compounds on Growth Performance and Carcass Composition of Finishing Pigs Compared with Paylean®

Further studies with lower doses, larger group sizes and a direct comparison to ractopamine are conducted. As a direct competitor to ractopamine, the SARM treated animals demonstrate the highest ADGs in the fourth week of treatment. By the fourth week of treatment with ractopamine the animals are desensitized to the beta-agonist and the producers are seeing diminished returns in lean mass gain. Therefore, longer treatment periods (>28 days) may be advantageous to the producers when feeding a SARM than when feeding ractopamine.

Example 10

Figure 6:
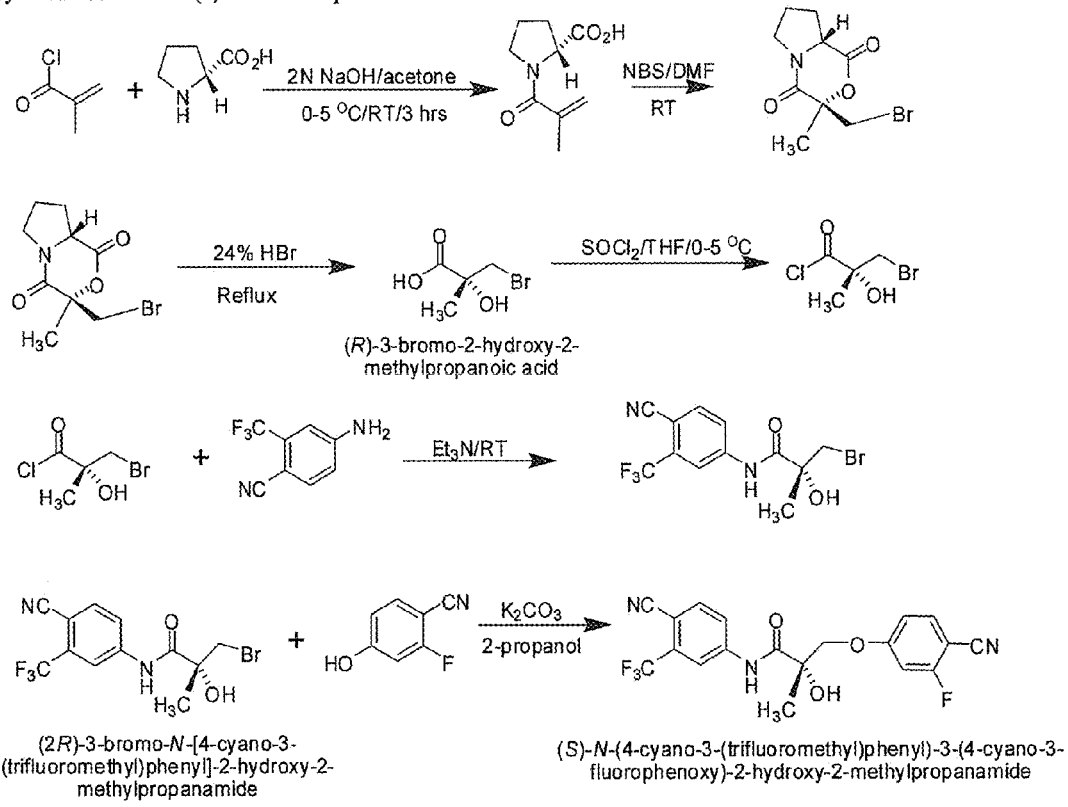
FIG. 6: Depicts a synthetic scheme for the preparation of an (S) enantiomer of a compound of formula XXIII (S-XXIII).

Synthesis of Compound of Formula S-XXIII (FIG. 6)

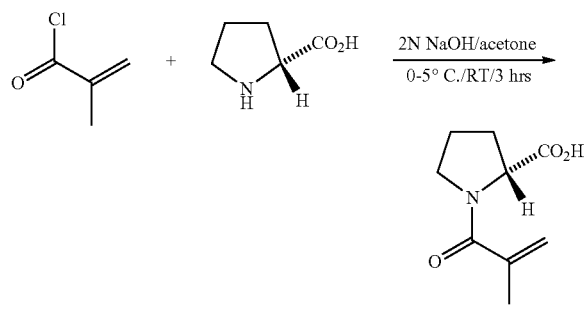

(2R)-1-Methacryloylpyrrolidin-2-carboxylic Acid

D-Proline, 14.93 g, 0.13 mol) was dissolved in 71 mL of 2 N NaOH and cooled in an ice bath; the resulting alkaline solution was diluted with acetone (71 mL). An acetone solution (71 mL) of methacryloyl chloride (13.56 g, 0.13 mol) and 2 N NaOH solution (71 mL) were simultaneously added over 40 min to the aqueous solution of D-proline in an ice bath. The pH of the mixture was kept at 10-11° C. during the addition of the methacryloyl chloride. After stirring (3 h, room temperature), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over $Na_2SO_4$, filtered through Celite®, and evaporated in vacuo to give the crude product as a colorless oil. Recrystallization of the oil from ethyl ether and hexanes afforded 16.2 g (68%) of the desired compound as colorless crystals: mp 102-103° C. (lit. mp 102.5-103.5° C.); the NMR spectrum of this compound demonstrated the existence of two rotamers of the title compound. $^1$H NMR (300 MHz, DMSO-$d_6$) δ 5.28 (s) and 5.15 (s) for the first rotamer, 5.15 (s) and 5.03 (s) for the second rotamer (totally 2H for both rotamers, vinyl $CH_2$), 4.48-4.44 for the first rotamer, 4.24-4.20 (m) for the second rotamer (totally 1H for both rotamers, CH at the chiral center), 3.57-3.38 (m, 2H, $CH_2$), 2.27-2.12 (1H, CH), 1.97-1.72 (m, 6H, $CH_2$, CH, Me); $^{13}$C NMR (75 MHz, DMSO-$d_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 cm$^{-1}$; $[α]_D^{26}$ +80.8° (c=1, MeOH); Anal. Calcd. for $C_9H_{13}NO_3$: C, 59.00; H, 7.15; N, 7.65. Found: C, 59.13; H, 7.19; N, 7.61.

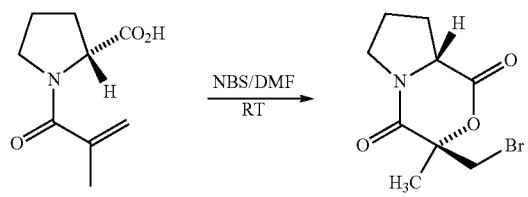

(3R,8aR)-3-Bromomethyl-3-methyl-tetrahydro-pyrrolo[2,1-c][1,4]oxazine-1,4-dione

A solution of NBS (23.5 g, 0.132 mol) in 100 mL of DMF was added dropwise to a stirred solution of the (methylacryloyl)-pyrrolidine (16.1 g, 88 mmol) in 70 mL of DMF under argon at room temperature, and the resulting mixture was stirred 3 days. The solvent was removed in vacuo, and a yellow solid was precipitated. The solid was suspended in water, stirred overnight at room temperature, filtered, and dried to give 18.6 g (81%) (smaller weight when dried~34%) of the title compound as a yellow solid: mp 152-154° C.; $^1$H NMR (300 MHz, DMSO-$d_6$) δ 4.69 (dd, J=9.6 Hz, J=6.7 Hz, 1H, CH at the chiral center), 4.02 (d, J=11.4 Hz, 1H, $CHH_a$), 3.86 (d, J=11.4 Hz, 1H, $CHH_b$), 3.53-3.24 (m, 4H, $CH_2$), 2.30-2.20 (m, 1H, CH), 2.04-1.72 (m, 3H, $CH_2$ and CH), 1.56 (s, 2H, Me); $^{13}$C NMR (75 MHz, DMSO-$d_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; $[α]_D^{26}$ +124.5° (c=1.3, chloroform); Anal. Calcd. for $C_9H_{12}BrNO_3$: C, 41.24; H, 4.61; N, 5.34. Found: C, 41.46; H, 4.64; N, 5.32.

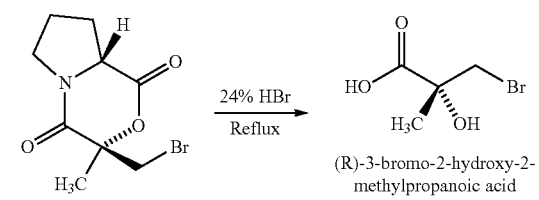

(2R)-3-Bromo-2-hydroxy-2-methylpropanoic Acid

A mixture of bromolactone (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated $NaHCO_3$ (100 mL×4). The aqueous solution was acidified with concentrated HCl to pH=1, which, in turn, was extracted with ethyl acetate (100 mL×4). The combined organic solution was dried over $Na_2SO_4$, filtered through Celite®, and evaporated in vacuo to dryness. Recrystallization from toluene afforded 10.2 g (86%) of the desired compound as colorless crystals: mp 107-109° C.; $^1$H NMR (300 MHz, DMSO-$d_6$) δ 3.63 (d, J=10.1 Hz, 1H, $CHH_a$), 3.52 (d, J=10.1 Hz, 1H, $CHH_b$), 1.35 (s, 3H, Me); IR (KBr) 3434 (OH), 3300-2500 (COOH), 1730 (C=O), 1449, 1421, 1380, 1292, 1193, 1085 cm$^{-1}$; $[α]_D^{26}$+ 10.5° (c=2.6, MeOH); Anal. Calcd. for $C_4H_7BrO_3$: C, 26.25; H, 3.86. Found: C, 26.28; H, 3.75.

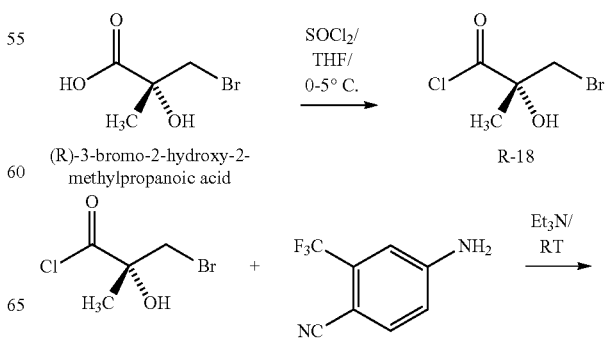

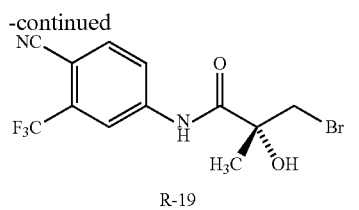

R-19

Synthesis of (2R)-3-Bromo-N-[4-cyano-3-(trifluoromethyl)phenyl]-2-hydroxy-2-methylpropanamide Thionyl chloride (46.02 g, 0.39 mol) was added dropwise to a cooled solution (less than 4° C.) of R-18 (51.13 g, 0.28 mol) in 300 mL of THF under an argon atmosphere. The resulting mixture was stirred for 3 h under the same condition. To this was added Et$_3$N (39.14 g, 0.39 mol) and stirred for 20 min under the same condition. After 20 min, 5-amino-2-cyanobenzotrifluoride (40.0 g, 0.21 mol), 400 mL of THF were added and then the mixture was allowed to stir overnight at room temperature. The solvent was removed under reduced pressure to give a solid which was treated with 300 mL of H$_2$O, extracted with EtOAc (2×400 mL). The combined organic extracts were washed with saturated NaHCO$_3$ solution (2×300 mL) and brine (300 mL). The organic layer was dried over MgSO$_4$ and concentrated under reduced pressure to give a solid which was purified from column chromatography using CH$_2$Cl$_2$/EtOAc (80:20) to give a solid. This solid was recrystallized from CH$_2$Cl$_2$/hexane to give 55.8 g (73.9%) of (2R)-3-bromo-N-[4-cyano-3-(trifluoromethyl)phenyl]-2-hydroxy-2-methylpropanamide (R-19) as a light-yellow solid.

$^1$H NMR (CDCl$_3$/TMS) δ 1.66 (s, 3H, CH$_3$), 3.11 (s, 1H, OH), 3.63 (d, J=10.8 Hz, 1H, CH$_2$), 4.05 (d, J=10.8 Hz, 1H, CH$_2$), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). Calculated Mass: 349.99, [M−H]$^−$ 349.0. M.p.: 124-126° C.

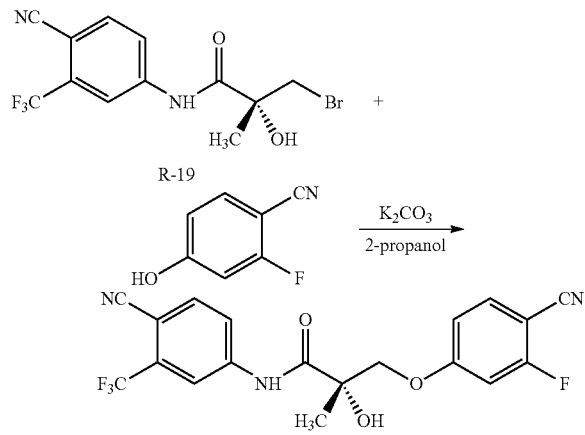

Synthesis of (S)—N-(4-cyano-3-(trifluoromethyl)phenyl)-3-(4-cyano-3-fluorophenoxy)-2-hydroxy-2-methylpropanamide A mixture of bromoamide ((2R)-3-bromo-N-[4-cyano-3-(trifluoromethyl)phenyl]-2-hydroxy-2-methylpropanamide, R-19 (2.0 g, 5.70 mmol) and anhydrous K$_2$CO$_3$ (2.4 g, 17.1 mmol) in 50 mL of acetone was heated to reflux for 2 h and then concentrated under reduced pressure to give a solid. The resulting solid was treated with 2-fluoro-4-hydroxybenzonitrile (1.2 g, 8.5 mmol) and anhydrous K$_2$CO$_3$ (1.6 g, 11.4 mmol) in 50 mL of 2-propanol and was heated to reflux for 3 h, then concentrated under reduced pressure to give a solid. The residue was treated with 100 mL of H$_2$O and then extracted with EtOAc (2×100 mL). The combined EtOAc extracts were washed with 10% NaOH (4×100 mL) and brine, successively. The organic layer was dried over MgSO$_4$ and then concentrated under reduced pressure to give an oil which was crystallized from CH$_2$Cl$_2$/hexane to give 0.5 g (23%) of (S)—N-(4-cyano-3-(trifluoromethyl)phenyl)-3-(4-cyano-3-fluorophenoxy)-2-hydroxy-2-methylpropanamide as a colorless solid.

$^1$H NMR (CDCl$_3$/TMS) δ 1.63 (s, 3H, CH$_3$), 3.34 (bs, 1H, OH), 4.08 (d, J=9.17 Hz, 1H, CH), 4.50 (d, J=9.17 Hz, 1H, CH), 6.74-6.82 (m, 2H, ArH), 7.50-7.55 (m, 1H, ArH), 7.81 (d, J=8.50 Hz, 1H, ArH), 7.97 (q, J=2.03, 8.50 Hz, 1H, ArH), 8.11 (d, J=2.03 Hz, 1H, ArH), 9.12 (s, 1H, NH). Calculated Mass: 407.1, [M+Na]$^+$ 430.0. Mp: 124-125° C.

FIG. 6 schematically depicts some embodiments of synthetic processes to obtain compound of formula S-XXIII.

Example 11

Preclinical Anabolic and Androgenic Pharmacology of Compound for Formula S-XXIII in Intact and Castrate Male Rats Anabolic and androgenic efficacy of compound of formula S-XXIII administered by daily oral gavage was tested. The S-isomer of compound (XXIII) was synthesized and tested as described herein.

Materials and Methods:

Male Sprague-Dawley rats weighing approximately 200 g were purchased from Harlan Bioproducts for Science (Indianapolis, Ind.). The animals were maintained on a 12-h light/dark cycle with food (7012C LM-485 Mouse/Rat Sterilizable Diet, Harlan Teklad, Madison, Wis.) and water available ad libitum. The animal protocol was reviewed and approved.

The test article for this study was weighed and dissolved in 10% DMSO (Fischer) diluted with PEG 300 (Acros Organics, NJ) for preparation of the appropriate dosage concentrations. The animals were housed in groups of 2 to 3 animals per cage. Animals were randomly assigned to one of seven groups consisting of 4 to 5 animals per group. Control groups (intact and ORX) were administered vehicle daily. Compound of formula S-XXIII was administered via oral gavage at doses of 0.01, 0.03, 0.1, 0.3, 0.75, and 1 mg/day to both intact and ORX groups. Where appropriate, animals were castrated on day one of the study. Treatment with compound of formula S-XXIII began nine days post ORX and was administered daily via oral gavage for fourteen days.

The animals were sacrificed under anesthesia (ketamine/xyalzine, 87:13 mg/kg) and body weights were recorded. In addition, ventral prostate, seminal vesicles, and levator ani muscle were removed, individually weighed, normalized to body weight, and expressed as a percentage of intact control. Student's T-test was used to compare individual dose groups to the intact control group. Significance was defined a priori as a P-value<0.05. Ventral prostate and seminal vesicle weights were evaluated as a measure of androgenic activity, whereas levator ani muscle weight was evaluated as a measure of anabolic activity. Blood was collected from the abdominal aorta, centrifuged, and sera were frozen at −80°

C. prior to determination of serum hormone levels. Serum luteinizing hormone (LH) and follicle stimulating hormone (FSH) concentrations were determined.

Figure 7:
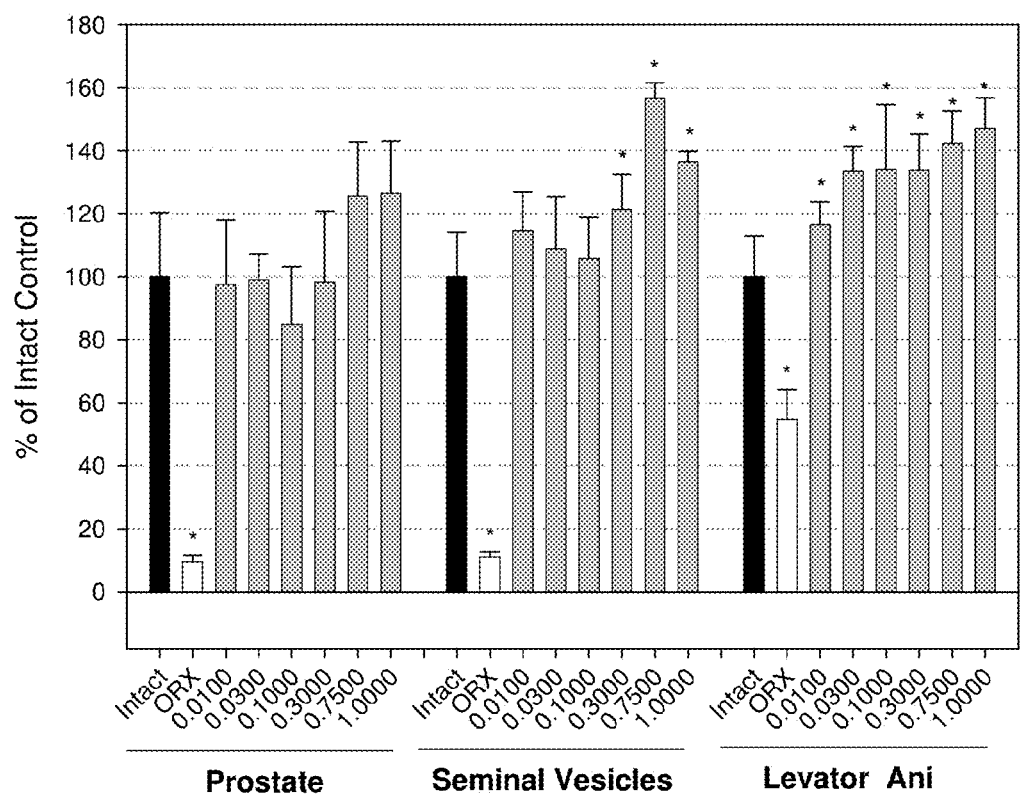
FIG. 7: Pharmacology of a compound of formula S-XXIII in intact rats. Asterisks represent statistically significant differences between the weight of the organ in the indicated group and that observed in intact animals treated with vehicle ($P<0.05$).

Results:

A series of dose-response studies in intact and castrated rats in order to evaluate the potency and efficacy of compound of formula S-XXIII in both androgenic (prostate and seminal vesicles) and anabolic (levator ani muscle) tissue was conducted. In intact animals, compound of formula S-XXIII treatment resulted in decreases in the weight of both prostate and seminal vesicles while the levator ani muscle weight was significantly increased. Levator ani muscle weight following compound of formula S-XXIII treatment were 116%±7%, 134%±8%, 134%±21%, 134%±11%, 142%±10%, and 147%±10% of intact controls, following treatment with 0.01, 0.03, 0.1, 0.3, 0.75, and 1.0 mg/day dose groups, respectively. The prostate weights were 98%±21%, 99%±8%, 85%±18%, 98%±22%, 126%±17%, and 126%±17% of intact controls, following treatment with 0.01, 0.03, 0.1, 0.3, 0.75, and 1 mg/day, respectively. Similarly seminal vesicle weight was 115%±12%, 109%±17%, 106%±13%, 121%±11%, 157%±5%, and 136%±3% of intact controls following treatment with 0.01, 0.03, 0.1, 0.3, 0.75, and 1 mg/day, respectively. The results are graphically presented in FIG. 7. These results are significant since current androgen therapies are contraindicated in some patient populations due to the proliferative androgenic effects in prostate and breast tissues. However, many patients in these populations could benefit from the anabolic actions of androgens in muscle and bone. Since compound of formula S-XXIII exhibited tissue selective anabolic effects, it may be possible to treat patient groups in which androgens were contraindicated in the past.

Figure 8:
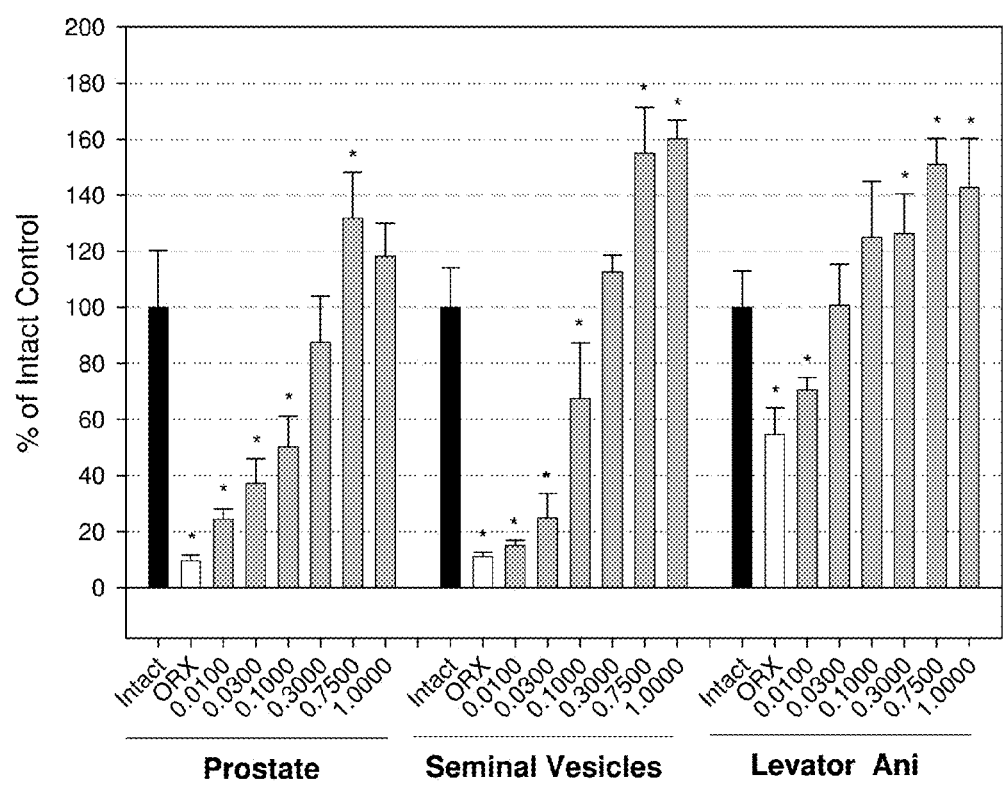
FIG. 8: Organ weights from castrated, compound of formula S-XXIII-treated rats presented as a percentage of intact control. *P-value$<0.05$ versus intact controls.

In castrated (ORX) animals, prostate weights following compound of formula S-XXIII treatment were 24%±4%, 37%±9%, 50%±11%, 88%±16%, 132%±16%, and 118±12% of intact controls following doses of 0, 0.01, 0.03, 0.1, 0.3, 0.75, and 1 mg/day, respectively. Similarly, seminal vesicle weights were 15%±2%, 25%±9%, 67%±20%, 113%±6%, 155%±16%, and 160%±7% of intact controls, following doses of 0, 0.01, 0.03, 0.1, 0.3, 0.75, and 1 mg/day, respectively. Significant increases were seen in levator ani muscle weights in all dose groups, when compared to intact controls. The levator ani muscle weights were 71%±4%, 101%±15%, 125%±20%, 126%±14%, 151±9%, and 143±17% of intact controls corresponding to 0, 0.01, 0.03, 0.1, 0.3, 0.75, and 1.0 mg/day dose groups, respectively. The results are graphically presented in FIG. 8.

One unexpected finding was that administration of only 0.03 mg/day was able to fully restore levator ani muscle weight.

Figure 9:
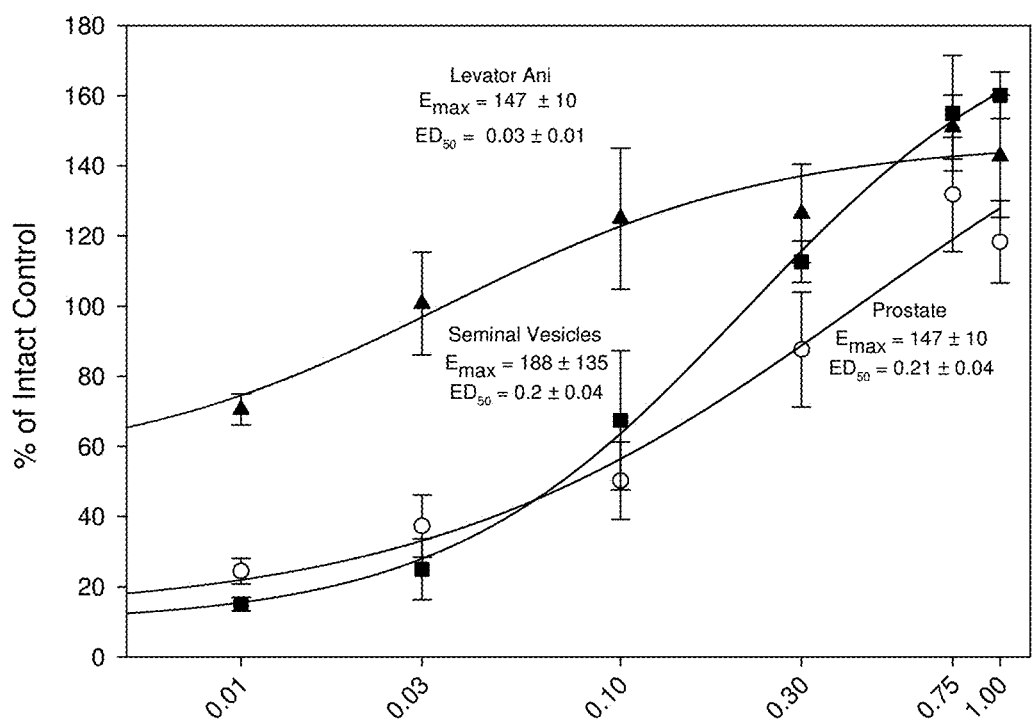
FIG. 9: Organ weight maintenance dose-response curves for a compound of formula S-XXIII and seminal vesicles (closed squares) were obtained by nonlinear regression analysis using the sigmoid $E_{max}$ model in WinNonlin®.

Comparable administration of testosterone propionate (TP) and S-3-(4-acetylaminophenoxy)-2-hydroxy-2-methyl-N-(4-nitro-3-trifluoromethylphenyl)propionamide, maximally stimulated the levator ani muscle weight to 104% and 101%, respectively, indicating the significantly enhanced efficacy and potency of compound of formula S-XXIII. Taken together, these data show that compound of formula S-XXIII restores lost muscle mass, which in some embodiments, finds valuable application in patients with sarcopenia or cachexia, or other wasting diseases or disorders. Additionally, the antiproliferative effects of compound of formula S-XXIII on the prostate may allow some patient populations, in which androgens are currently contraindicated, access to anabolic agents. $E_{max}$ values were obtained and were 147%±10%, 188%±135%, and 147%±10% for prostate, seminal vesicles, and levator ani, respectively. The $ED_{50}$ in prostate, seminal vesicles, and levator ani was 0.21±0.04, 0.2±0.04, and 0.03±0.01 mg/day, respectively. These results are graphically depicted in FIG. 9.

Example 12

Figure 10:
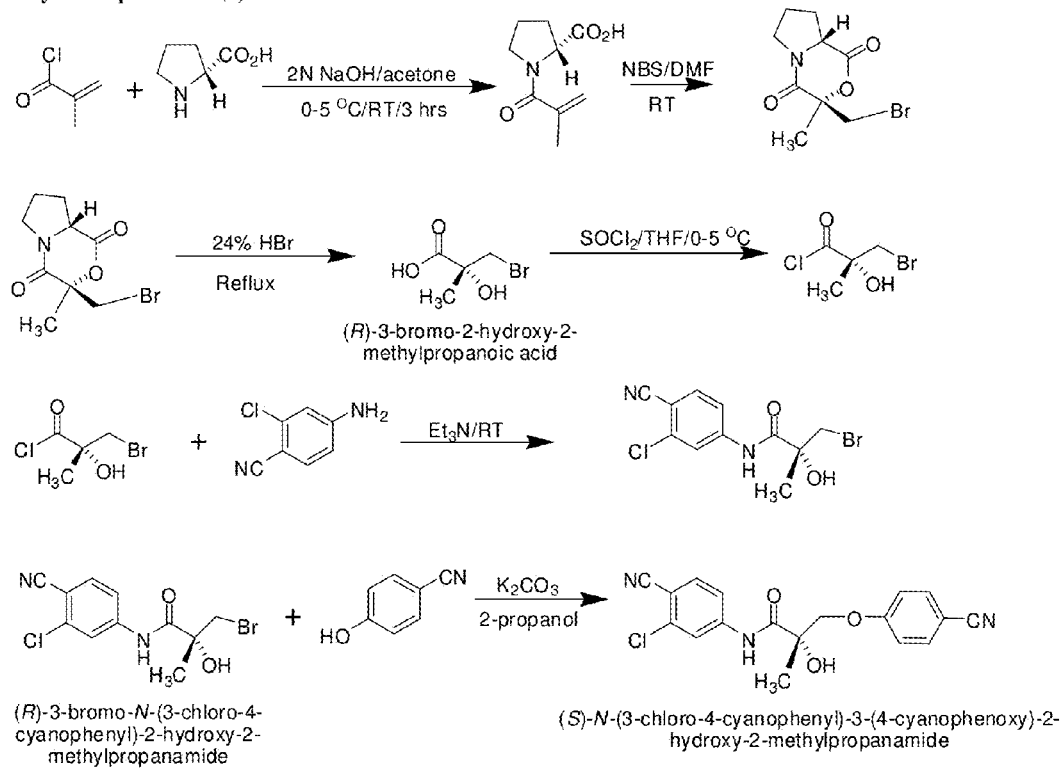
FIG. 10: Depicts a synthetic scheme for the preparation of an (S) enantiomer of a compound of formula XXIV (S-XXIV).

Synthesis of Compound of Formula S-XXIV) (FIG. 10)

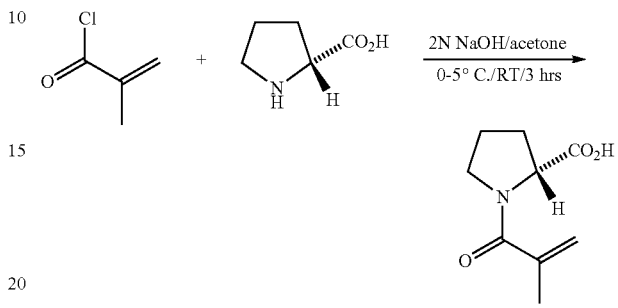

(2R)-1-Methacryloylpyrrolidin-2-carboxylic Acid

D-Proline, 14.93 g, 0.13 mol) was dissolved in 71 mL of 2 N NaOH and cooled in an ice bath; the resulting alkaline solution was diluted with acetone (71 mL). An acetone solution (71 mL) of methacryloyl chloride (13.56 g, 0.13 mol) and 2 N NaOH solution (71 mL) were simultaneously added over 40 min to the aqueous solution of D-proline in an ice bath. The pH of the mixture was kept at 10-11° C. during the addition of the methacryloyl chloride. After stirring (3 h, room temperature), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over $Na_2SO_4$, filtered through Celite®, and evaporated in vacuo to give the crude product as a colorless oil. Recrystallization of the oil from ethyl ether and hexanes afforded 16.2 g (68%) of the desired compound as colorless crystals: mp 102-103° C. (lit. mp 102.5-103.5° C.); the NMR spectrum of this compound demonstrated the existence of two rotamers of the title compound. $^1$H NMR (300 MHz, DMSO-$d_6$) δ 5.28 (s) and 5.15 (s) for the first rotamer, 5.15 (s) and 5.03 (s) for the second rotamer (totally 2H for both rotamers, vinyl $CH_2$), 4.48-4.44 for the first rotamer, 4.24-4.20 (m) for the second rotamer (totally 1H for both rotamers, CH at the chiral canter), 3.57-3.38 (m, 2H, $CH_2$), 2.27-2.12 (1H, CH), 1.97-1.72 (m, 6H, $CH_2$, CH, Me); $^{13}$C NMR (75 MHz, DMSO-$d_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C═O), 1647 (CO, COOH), 1584, 1508, 1459, 1369, 1348, 1178 cm$^{-1}$; $[\alpha]_D^{26}$ +80.8° (c=1, MeOH); Anal. Calcd. for $C_9H_{13}NO_3$: C, 59.00; H, 7.15; N, 7.65. Found: C, 59.13; H, 7.19; N, 7.61.

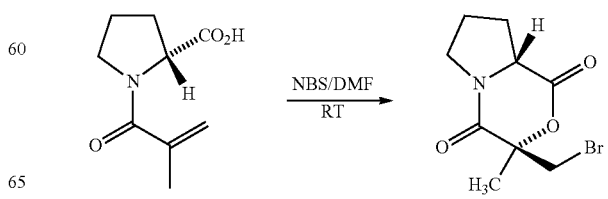

(3R,8aR)-3-Bromomethyl-3-methyl-tetrahydro-pyrrolo[2,1-c][1,4]oxazine-1,4-dione A solution of NBS (23.5 g, 0.132 mol) in 100 mL of DMF was added dropwise to a stirred solution of the (methylacryloyl)-pyrrolidine (16.1 g, 88 mmol) in 70 mL of DMF under argon at room temperature, and the resulting mixture was stirred 3 days. The solvent was removed in vacuo, and a yellow solid was precipitated. The solid was suspended in water, stirred overnight at room temperature, filtered, and dried to give 18.6 g (81%) (smaller weight when dried~34%) of the title compound as a yellow solid: mp 152-154° C.; $^1$H NMR (300 MHz, DMSO-$d_6$) δ 4.69 (dd, J=9.6 Hz, J=6.7 Hz, 1H, CH at the chiral center), 4.02 (d, J=11.4 Hz, 1H, CHH$_a$), 3.86 (d, J=11.4 Hz, 1H, CHH$_b$), 3.53-3.24 (m, 4H, CH$_2$), 2.30-2.20 (m, 1H, CH), 2.04-1.72 (m, 3H, CH$_2$ and CH), 1.56 (s, 2H, Me); $^{13}$C NMR (75 MHz, DMSO-$d_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; $[\alpha]_D^{26}$ +124.5° (c=1.3, chloroform); Anal. Calcd. for C$_9$H$_{12}$BrNO$_3$: C, 41.24; H, 4.61; N, 5.34. Found: C, 41.46; H, 4.64; N, 5.32.

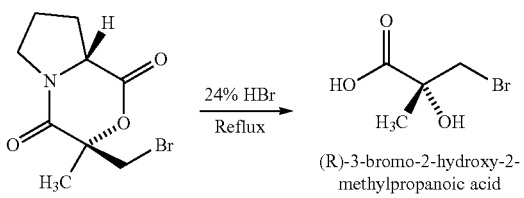

(2R)-3-Bromo-2-hydroxy-2-methylpropanoic Acid

A mixture of bromolactone (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated NaHCO$_3$ (100 mL×4). The aqueous solution was acidified with concentrated HCl to pH=1, which, in turn, was extracted with ethyl acetate (100 mL×4). The combined organic solution was dried over Na$_2$SO$_4$, filtered through Celite®, and evaporated in vacuo to dryness. Recrystallization from toluene afforded 10.2 g (86%) of the desired compound as colorless crystals: mp 107-109° C.; $^1$H NMR (300 MHz, DMSO-$d_6$) δ 3.63 (d, J=10.1 Hz, 1H, CHH$_a$), 3.52 (d, J=10.1 Hz, 1H, CHH$_b$), 1.35 (s, 3H, Me); IR (KBr) 3434 (OH), 3300-2500 (COOH), 1730 (C=O), 1449, 1421, 1380, 1292, 1193, 1085 cm$^{-1}$; $[\alpha]_D^{26}$ +10.5° (c=2.6, MeOH); Anal. Calcd. for C$_4$H$_7$BrO$_3$: C, 26.25; H, 3.86. Found: C, 26.28; H, 3.75.

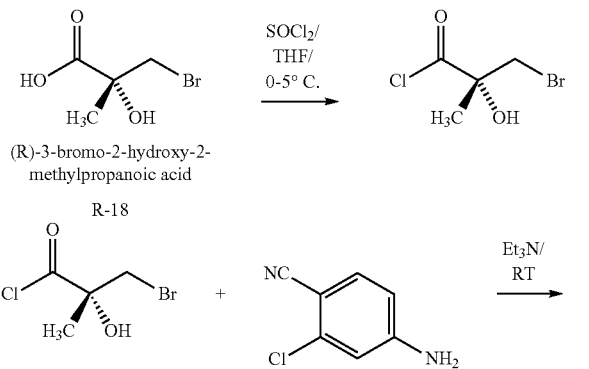

Synthesis of (2R)-3-bromo-N-(3-chloro-4-cyanophenyl)-2-hydroxy-2-methylpropanamide

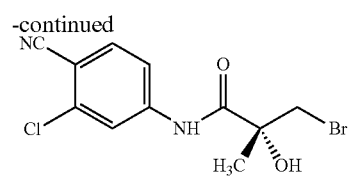

Thionyl chloride (7.8 g, 65.5 mmol) was added dropwise to a cooled solution (less than 4° C.) of (R)-3-bromo-2-hydroxy-2-methylpropanoic acid (9.0 g, 49.2 mol) in 50 mL of THF under an argon atmosphere. The resulting mixture was stirred for 3 h under the same condition. To this was added Et$_3$N (6.6 g, 65.5 mol) and stirred for 20 min under the same condition. After 20 min, 4-amino-2-chlorobenzonitrile (5.0 g, 32.8 mmol) and 100 mL of THF were added and then the mixture was allowed to stir overnight at room temperature. The solvent was removed under reduced pressure to give a solid which was treated with 100 mL of H$_2$O, extracted with EtOAc (2×150 mL). The combined organic extracts were washed with saturated NaHCO$_3$ solution (2×100 mL) and brine (300 mL), successively. The organic layer was dried over MgSO$_4$ and concentrated under reduced pressure to give a solid which was purified from column chromatography using EtOAc/hexane (50:50) to give 7.7 g (49.4%) of target compound as a brown solid.

$^1$H NMR (CDCl$_3$/TMS) δ 1.7 (s, 3H, CH$_3$), 3.0 (s, 1H, OH), 3.7 (d, 1H, CH), 4.0 (d, 1H, CH), 7.5 (d, 1H, ArH), 7.7 (d, 1H, ArH), 8.0 (s, 1H, ArH), 8.8 (s, 1H, NH). MS: 342.1 (M+23). Mp 129° C.

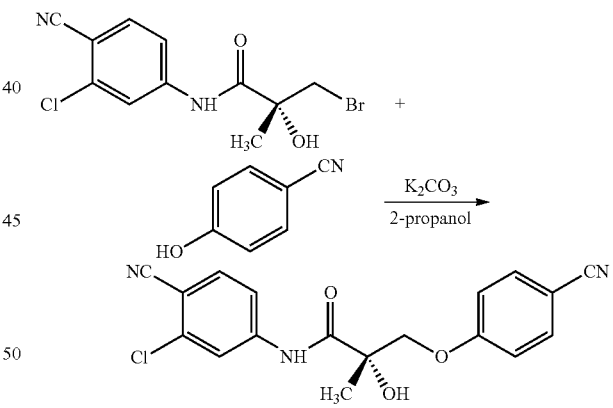

Synthesis of (S)—N-(3-chloro-4-cyanophenyl)-3-(4-cyanophenoxy)-2-hydroxy-2-methylpropanamide A mixture of bromoamide (2.0 g, 6.3 mmol), anhydrous K$_2$CO$_3$ (2.6 g, 18.9 mmol) in 50 mL of acetone was heated to reflux for 2 h and then concentrated under reduced pressure to give a solid. The resulting solid was treated with 4-cyanophenol (1.1 g, 9.5 mmol) and anhydrous K$_2$CO$_3$ (1.7 g, 12.6 mmol) in 50 mL of 2-propanol was heated to reflux for 3 h and then concentrated under reduced pressure to give a solid. The residue was treated with 100 mL of H$_2$O and then extracted with EtOAc (2×100 mL). The combined EtOAc extracts were washed with 10% NaOH (4×100 mL)

and brine, successively. The organic layer was dried over MgSO$_4$ and then concentrated under reduced pressure to give an oil which was purified by column chromatography using EtOAc/hexane (50:50) to give a solid. The solid was recrystallized from CH$_2$Cl$_2$/hexane to give 1.4 g (61.6%) of (S)—N-(3-chloro-4-cyanophenyl)-3-(4-cyanophenoxy)-2-hydroxy-2-methylpropanamide as a colorless solid.

$^1$H NMR (CDCl$_3$/TMS) δ 1.61 (s, 3H, CH$_3$), 3.25 (s, 1H, OH), 4.06 (d, J=9.15 Hz, 1H, CH), 4.50 (d, J=9.15 Hz, 1H, CH), 6.97-6.99 (m, 2H, ArH), 7.53-7.59 (m, 4H, ArH), 7.97 (d, J=2.01 Hz, 1H, ArH), 8.96 (s, 1H, NH). Calculated Mass: 355.1, [M+Na]$^+$ 378.0. Mp: 103-105° C.

Example 13

Preclinical Anabolic and Androgenic Pharmacology of S-XXIV in Intact and Castrate Male Rats Anabolic and androgenic efficacy of compound of formula S-XXIV administered by daily oral gavage was tested. The S-isomer of compound S-XXIV was synthesized and tested as described herein.

Materials and Methods:

Male Sprague-Dawley rats weighing approximately 200 g were purchased from Harlan Bioproducts for Science (Indianapolis, Ind.). The animals were maintained on a 12-h light/dark cycle with food (7012C LM-485 Mouse/Rat Sterilizable Diet, Harlan Teklad, Madison, Wis.) and water available ad libitum. The animal protocol was reviewed and approved. The anabolic and androgenic activity of compound of formula S-XXIV in intact animals was tested, as well as a dose response evaluation in acutely orchidectomized (ORX) animals. Regenerative effects of the compound of formula S-XXIV in chronically (9 days) ORX rats were similarly evaluated.

The test article for this study was weighed and dissolved in 10% DMSO (Fischer) diluted with PEG 300 (Acros Organics, NJ) for preparation of the appropriate dosage concentrations. The animals were housed in groups of 2 to 3 animals per cage. Animals were randomly assigned to one of seven groups consisting of 4 to 5 animals per group. Control groups (intact and ORX) were administered vehicle daily. Compound of formula S-XXIV was administered via oral gavage at doses of 0.01, 0.03, 0.1, 0.3, 0.75, and 1 mg/day to both intact and ORX groups. Where appropriate, animals were castrated on day one of the study. Treatment with compound of formula S-XXIV began nine days post ORX and was administered daily via oral gavage for fourteen days.

The animals were sacrificed under anesthesia (ketamine/xyalzine, 87:13 mg/kg) and body weights were recorded. In addition, ventral prostate, seminal vesicles, and levator ani muscle were removed, individually weighed, normalized to body weight, and expressed as a percentage of intact control. Student's T-test was used to compare individual dose groups to the intact control group. Significance was defined a priori as a P-value<0.05. Ventral prostate and seminal vesicle weights were evaluated as a measure of androgenic activity, whereas levator ani muscle weight was evaluated as a measure of anabolic activity. Blood was collected from the abdominal aorta, centrifuged, and sera were frozen at −80° C. prior to determination of serum hormone levels. Serum luteinizing hormone (LH) and follicle stimulating hormone (FSH) concentrations were determined.

Results:

A series of dose-response studies in intact and castrated rats in order to evaluate the potency and efficacy of compound of formula S-XXIV in both androgenic (prostate and seminal vesicles) and anabolic (levator ani muscle) tissue was conducted. In intact animals, compound of formula S-XXIV treatment resulted in decreases in the weight of both prostate and seminal vesicles while the levator ani muscle weight was significantly increased. Levator ani muscle weight following compound of formula S-XXIV treatment were 107%±5%, 103%±7%, 97%±7%, 103%±5%, 118%±7%, and 118%±7% of intact controls following doses of 0.01, 0.03, 0.1, 0.3, 0.75, and 1 mg/day, respectively. The prostate weights were 103%±10%, 99%±10%, 58%±10%, 58%±15%, 65%±20%, and 77%±23% of intact controls following doses of 0.01, 0.03, 0.1, 0.3, 0.75, and 1 mg/day, respectively. These results are significant since current androgen therapies are contraindicated in some patient populations due to the proliferative androgenic effects in prostate and breast tissues. However, many patients in these populations could benefit from the anabolic actions of androgens in muscle and bone. Since compound of formula S-XXIV exhibited tissue selective anabolic effects, it may be possible to treat patient groups in which androgens were contraindicated in the past.

Figure 11:
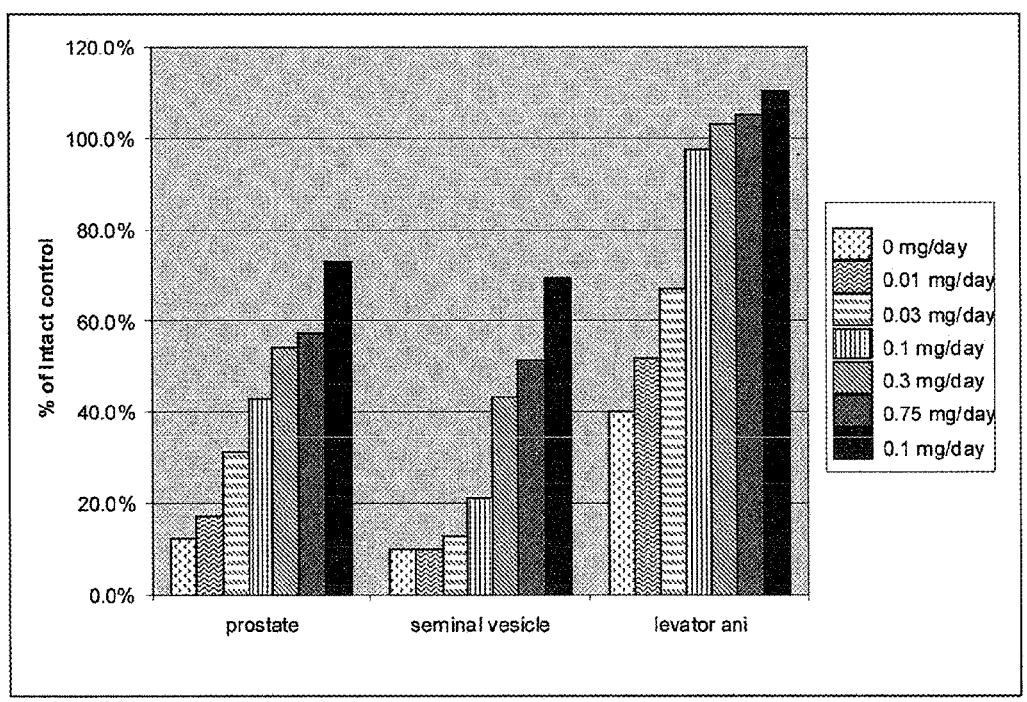
FIG. 11: Anabolic and androgenic activity of a compound of formula S-XXIV in ORX rats.

In castrated, ORX animals, prostate weights following compound of formula S-XXIV treatment were 12%±2%, 17%±6%, 31%±3%, 43%±15%, 54%±17%, 58%±10%, and 73%±12% of intact controls following doses of 0, 0.01, 0.03, 0.1, 0.3, 0.75, and 1 mg/day, respectively (FIG. 11). Similarly, seminal vesicle weights were 10%±2%, 10%±3%, 13%±4%, 21%±6%, 43%±8%, 51%±9%, and 69%±14% of intact controls following doses of 0, 0.01, 0.03, 0.1, 0.3, 0.75, and 1 mg/day, respectively (FIG. 11). Significant increases were seen in levator ani muscle weights in all dose groups, when compared to intact controls. The levator ani muscle weights were 40%±5%, 52%±8%, 67%±9%, 98%±10%, 103%±12%, 105%±12% and 110%±17% of intact controls corresponding to 0, 0.01, 0.03, 0.1, 0.3, 0.75, and 1.0 mg/day dose groups, respectively (FIG. 11).

Testosterone propionate (TP) and S-3-(4-acetylaminophenoxy)-2-hydroxy-2-methyl-N-(4-nitro-3-trifluoromethyl-phenyl)propionamide (S-4), maximally stimulated the levator ani muscle weight to 104% and 101%, respectively. These data show that compound of formula S-XXIV exhibited significantly greater efficacy and potency than either TP or S-4. As a whole, these data show that compound of formula S-XXIV is able to stimulate muscle growth in the presence or absence of testosterone while exerting antiproliferative effects on the prostate. These data show that the compound of formula S-XXIV restores lost muscle mass in patients with sarcopenia or cachexia. Additionally, the antiproliferative effects of the compound of formula S-XXIV on the prostate may allow some patient populations, in which androgens are currently contraindicated, access to anabolic agents.

Anabolic ratios were derived comparing muscle/prostate weight in castrated rats. Values obtained were 3.02, 2.13, 2.27, 1.90, 1.83 and 1.51 following doses of 0.01, 0.03, 0.1, 0.3, 0.75 and 1 mg/day, respectively.

Animals receiving 1 mg/day of compound of formula S-XXIV exhibited a prostate weight of 77%±23% and levator ani muscle weight of 118%±7% of intact control values, respectively. Compound of formula S-XXIV maintained prostate weight following orchidectomy at 73±12% of intact controls and levator ani muscle weight at 110±17% of intact controls. A derived dose of 0.1 mg/day of compound of formula S-XXIV would restore levator ani muscle weight to 100%, while such dose would only restore 43±15% prostate weight.

Example 14

Figure 12:
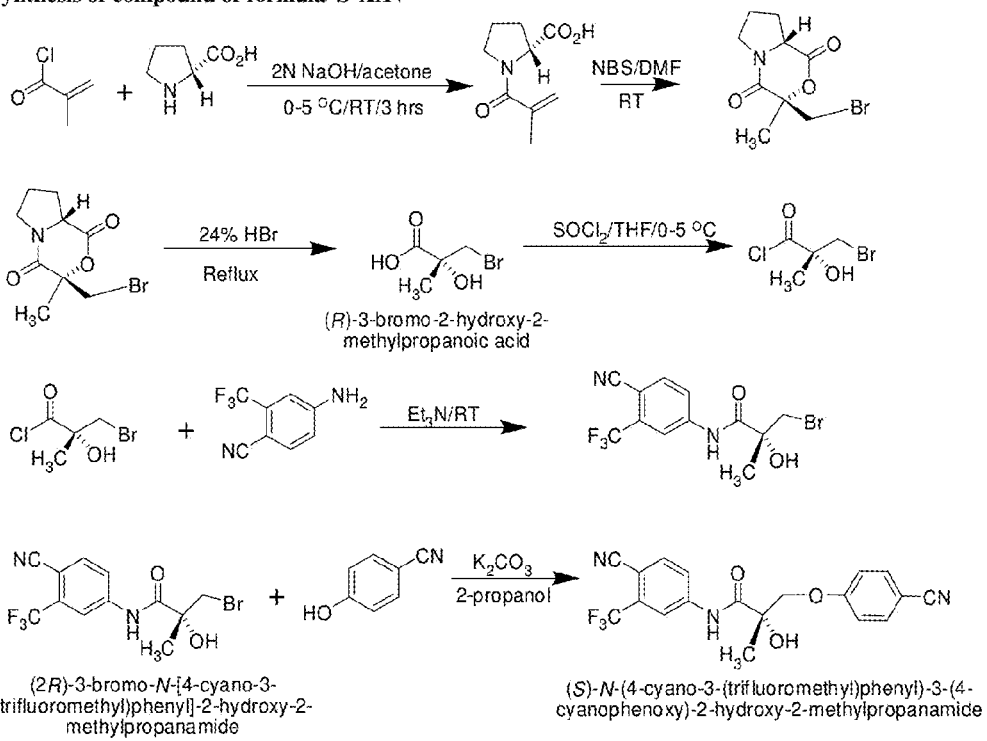
FIG. 12: Depicts a synthetic scheme for the preparation of an (S) enantiomer of a compound of formula XXV (S-XXV).

Synthesis of Compound of Formula S-XXV (FIG. 12)

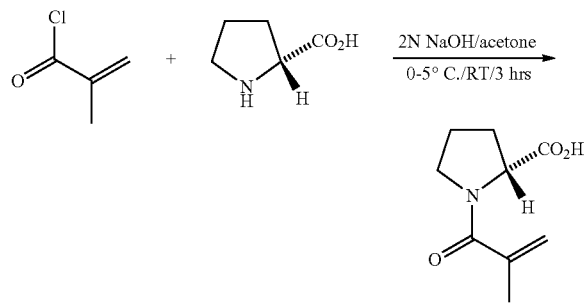

(2R)-1-Methacryloylpyrrolidin-2-carboxylic Acid

D-Proline, 14.93 g, 0.13 mol) was dissolved in 71 mL of 2 N NaOH and cooled in an ice bath; the resulting alkaline solution was diluted with acetone (71 mL). An acetone solution (71 mL) of methacryloyl chloride (13.56 g, 0.13 mol) and 2 N NaOH solution (71 mL) were simultaneously added over 40 min to the aqueous solution of D-proline in an ice bath. The pH of the mixture was kept at 10-11° C. during the addition of the methacryloyl chloride. After stirring (3 h, room temperature), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over $Na_2SO_4$, filtered through Celite®, and evaporated in vacuo to give the crude product as a colorless oil. Recrystallization of the oil from ethyl ether and hexanes afforded 16.2 g (68%) of the desired compound as colorless crystals: mp 102-103° C. (lit. mp 102.5-103.5° C.); the NMR spectrum of this compound demonstrated the existence of two rotamers of the title compound. $^1$H NMR (300 MHz, DMSO-$d_6$) δ 5.28 (s) and 5.15 (s) for the first rotamer, 5.15 (s) and 5.03 (s) for the second rotamer (totally 2H for both rotamers, vinyl $CH_2$), 4.48-4.44 for the first rotamer, 4.24-4.20 (m) for the second rotamer (totally 1H for both rotamers, CH at the chiral canter), 3.57-3.38 (m, 2H, $CH_2$), 2.27-2.12 (1H, CH), 1.97-1.72 (m, 6H, $CH_2$, CH, Me); $^{13}$C NMR (75 MHz, DMSO-$d_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 cm$^{-1}$; $[α]_D^{26}$ +80.8° (c=1, MeOH); Anal. Calcd. for $C_9H_{13}NO_3$: C, 59.00; H, 7.15; N, 7.65. Found: C, 59.13; H, 7.19; N, 7.61.

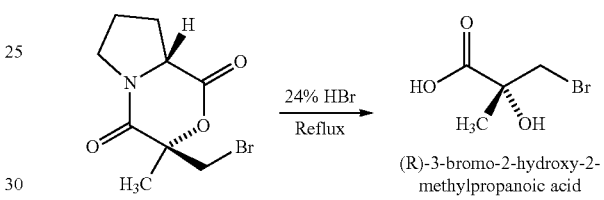

(3R,8aR)-3-Bromomethyl-3-methyl-tetrahydro-pyrrolo[2,1-c][1,4]oxazine-1,4-dione A solution of NBS (23.5 g, 0.132 mol) in 100 mL of DMF was added dropwise to a stirred solution of the (methylacryloyl)-pyrrolidine (16.1 g, 88 mmol) in 70 mL of DMF under argon at room temperature, and the resulting mixture was stirred 3 days. The solvent was removed in vacuo, and a yellow solid was precipitated. The solid was suspended in water, stirred overnight at room temperature, filtered, and dried to give 18.6 g (81%) (smaller weight when dried~34%) of the title compound as a yellow solid: mp 152-154° C.; $^1$H NMR (300 MHz, DMSO-$d_6$) δ 4.69 (dd, J=9.6 Hz, J=6.7 Hz, 1H, CH at the chiral center), 4.02 (d, J=11.4 Hz, 1H, $CHH_a$), 3.86 (d, J=11.4 Hz, 1H, $CHH_b$), 3.53-3.24 (m, 4H, $CH_2$), 2.30-2.20 (m, 1H, CH), 2.04-1.72 (m, 3H, $CH_2$ and CH), 1.56 (s, 2H, Me); $^{13}$C NMR (75 MHz, DMSO-$d_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; $[α]_D^{26}$ +124.5° (c=1.3, chloroform); Anal. Calcd. for $C_9H_{12}BrNO_3$: C, 41.24; H, 4.61; N, 5.34. Found: C, 41.46; H, 4.64; N, 5.32.

(2R)-3-Bromo-2-hydroxy-2-methylpropanoic Acid

A mixture of bromolactone (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated $NaHCO_3$ (100 mL×4). The aqueous solution was acidified with concentrated HCl to pH=1, which, in turn, was extracted with ethyl acetate (100 mL×4). The combined organic solution was dried over $Na_2SO_4$, filtered through Celite®, and evaporated in vacuo to dryness. Recrystallization from toluene afforded 10.2 g (86%) of the desired compound as colorless crystals: mp 107-109° C.; $^1$H NMR (300 MHz, DMSO-$d_6$) δ 3.63 (d, J=10.1 Hz, 1H, $CHH_a$), 3.52 (d, J=10.1 Hz, 1H, $CHH_b$), 1.35 (s, 3H, Me); IR (KBr) 3434 (OH), 3300-2500 (COOH), 1730 (C=O), 1449, 1421, 1380, 1292, 1193, 1085 cm$^{-1}$; $[α]_D^{26}$ +10.5° (c=2.6, MeOH); Anal. Calcd. for $C_4H_7BrO_3$: C, 26.25; H, 3.86. Found: C, 26.28; H, 3.75.

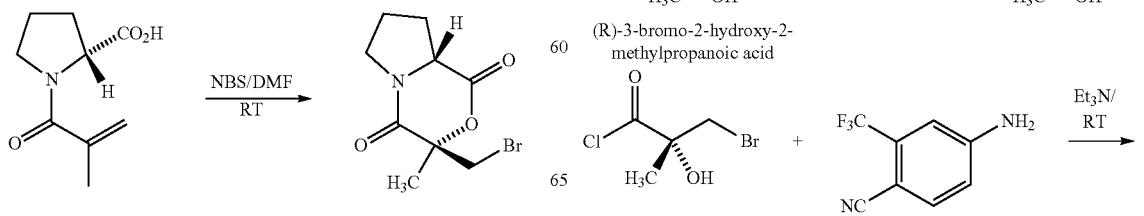

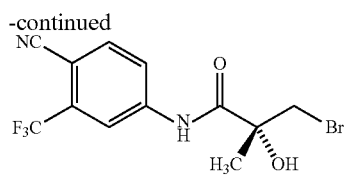

Synthesis of (2R)-3-Bromo-N-[4-cyano-3-(trifluoromethyl)phenyl]-2-hydroxy-2-methylpropanamide Thionyl chloride (46.02 g, 0.39 mol) was added dropwise to a cooled solution (less than 4° C.) of (R)-3-bromo-2-hydroxy-2-methylpropanoic acid (51.13 g, 0.28 mol) in 300 mL of THF under an argon atmosphere. The resulting mixture was stirred for 3 h under the same condition. To this was added Et$_3$N (39.14 g, 0.39 mol) and stirred for 20 min under the same condition. After 20 min, 5-amino-2-cyanobenzotrifluoride (40.0 g, 0.21 mol), 400 mL of THF were added and then the mixture was allowed to stir overnight at room temperature. The solvent was removed under reduced pressure to give a solid which was treated with 300 mL of H$_2$O, extracted with EtOAc (2×400 mL). The combined organic extracts were washed with saturated NaHCO$_3$ solution (2×300 mL) and brine (300 mL). The organic layer was dried over MgSO$_4$ and concentrated under reduced pressure to give a solid which was purified from column chromatography using CH$_2$Cl$_2$/EtOAc (80:20) to give a solid. This solid was recrystallized from CH$_2$Cl$_2$/hexane to give 55.8 g (73.9%) of (2R)-3-bromo-N-[4-cyano-3-(trifluoromethyl)phenyl]-2-hydroxy-2-methylpropanamide as a light-yellow solid.

$^1$H NMR (CDCl$_3$/TMS) δ 1.66 (s, 3H, CH$_3$), 3.11 (s, 1H, OH), 3.63 (d, J=10.8 Hz, 1H, CH$_2$), 4.05 (d, J=10.8 Hz, 1H, CH$_2$), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). Calculated Mass: 349.99, [M−H]⁻ 349.0. M.p.: 124-126° C.

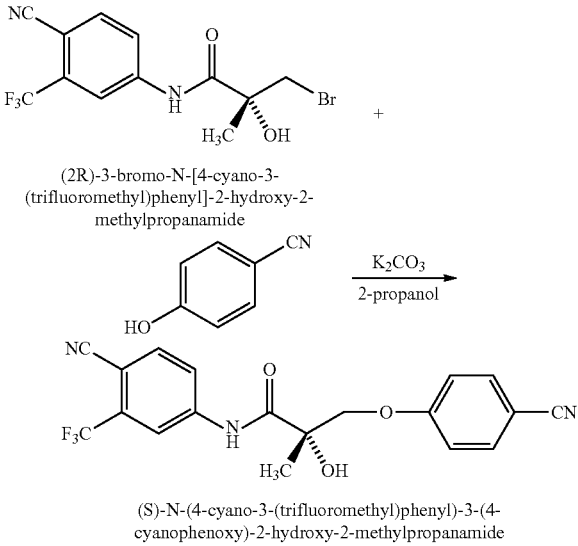

Synthesis of (S)—N-(4-Cyano-3-(trifluoromethyl)phenyl)-3-(4-cyanophenoxy)-2-hydroxy-2-methylpropanamide A mixture of bromoamide ((2R)-3-bromo-N-[4-cyano-3-(trifluoromethyl)phenyl]-2-hydroxy-2-methylpropanamide, 50 g, 0.14 mol), anhydrous K$_2$CO$_3$ (59.04 g, 0.43 mol), 4-cyanophenol (25.44 g, 0.21 mol) in 500 mL of 2-propanol was heated to reflux for 3 h and then concentrated under reduced pressure to give a solid. The resulting residue was treated with 500 mL of H$_2$O and then extracted with EtOAc (2×300 mL). The combined EtOAc extracts were washed with 10% NaOH (4×200 mL) and brine. The organic layer was dried over MgSO$_4$ and then concentrated under reduced pressure to give an oil which was treated with 300 mL of ethanol and an activated carbon. The reaction mixture was heated to reflux for 1 h and then the hot mixture was filtered through Celite®. The filtrate was concentrated under reduced pressure to give an oil. This oil was purified by column chromatography using CH$_2$Cl$_2$/EtOAc (80:20) to give an oil which was crystallized from CH$_2$Cl$_2$/hexane to give 33.2 g (59.9%) of (S)—N-(4-cyano-3-(trifluoromethyl)phenyl)-3-(4-cyanophenoxy)-2-hydroxy-2-methylpropanamide as a colorless solid (a cotton type).

$^1$H NMR (CDCl$_3$/TMS) δ 1.63 (s, 3H, CH$_3$), 3.35 (s, 1H, OH), 4.07 (d, J=9.04 Hz, 1H, CH), 4.51 (d, J=9.04 Hz, 1H, CH), 6.97-6.99 (m, 2H, ArH), 7.57-7.60 (m, 2H, ArH), 7.81 (d, J=8.55 Hz, 1H, ArH), 7.97 (dd, J=1.95, 8.55 Hz, 1H, ArH), 8.12 (d, J=1.95 Hz, 1H, ArH), 9.13 (bs, 1H, NH). Calculated Mass: 389.10, [M−H]⁻ 388.1. Mp: 92-94° C.

Example 15

Androgenic & Anabolic Activity in Intact and ORX Rats of Compound of Formula S-XXV

Materials and Methods

Male Sprague-Dawley rats weighing approximately 200 g were purchased from Harlan Bioproducts for Science (Indianapolis, Ind.). The animals were maintained on a 12-h light/dark cycle with food (7012C LM-485 Mouse/Rat Sterilizable Diet, Harlan Teklad, Madison, Wis.) and water available ad libitum. The animal protocol was reviewed and approved. Anabolic and androgenic activity of compound of formula S-XXV in intact animals was evaluated, and the dose response in acutely orchidectomized (ORX) animals was evaluated as well. Regenerative effects of compound for formula S-XXV in chronically (9 days) ORX rats were also assessed.

The compound was weighed and dissolved in 10% DMSO (Fischer) diluted with PEG 300 (Acros Organics, NJ) for preparation of the appropriate dosage concentrations. The animals were housed in groups of 2 to 3 animals per cage. Intact and ORX animals were randomly assigned to one of seven groups consisting of 4 to 5 animals per group. Control groups (intact and ORX) were administered vehicle daily. Compound of formula S-XXV was administered via oral gavage at doses of 0.01, 0.03, 0.1, 0.3, 0.75, and 1 mg/day to both intact and ORX groups.

Castrated animals (on day one of the study) were randomly assigned to dose groups (4-5 animals/group) of 0.01, 0.03, 0.1, 0.3, 0.75, and 1 mg/day, for dose-response evaluation. Dosing began nine days post ORX and was administered daily via oral gavage for fourteen days. The animals were sacrificed under anesthesia (ketamine/xyalzine, 87:13 mg/kg) after a 14-day dosing regimen, and body weights were recorded. In addition, ventral prostate, seminal vesicles, and levator ani muscle were removed, individually weighed, normalized to body weight, and expressed as a percentage of intact control. Student's T-test was used to compare individual dose groups to the intact control group. Significance was defined a priori as a P-value<0.05. As a measure of androgenic activity, ventral prostate and seminal vesicle weights were evaluated, whereas levator ani muscle weight was evaluated as a measure of anabolic activity. Blood was collected from the abdominal aorta, centrifuged, and sera were frozen at −80° C. prior to determination of serum hormone levels. Serum lutenizing hormone (LH) and follicle stimulating hormone (FSH) concentrations were determined.

Results

Prostate weights following compound of formula S-XXV treatment were 111%±21%, 88%±15%, 77%±17%, 71%±16%, 71%±10%, and 87%±13% of intact controls following doses of 0.01, 0.03, 0.1, 0.3, 0.75, and 1 mg/day, respectively. Similarly, seminal vesicle weights decreased to 94%±9%, 77%±11%, 80%±9%, 73%±12%, 77%±10%, and 88%±14% of intact controls following doses of 0.01, 0.03, 0.1, 0.3, 0.75, and 1 mg/day, respectively. Significant increases were seen in levator ani muscle weights of sham animals, however, in all dose groups, when compared to intact controls. The levator ani muscle weights were 120%±12%, 116%±7%, 128%±7%, 134%±7%, 125%±9%, and 146%±17% of intact controls corresponding to 0.01, 0.03, 0.1, 0.3, 0.75, and 1.0 mg/day dose groups, respectively.

Figure 13:
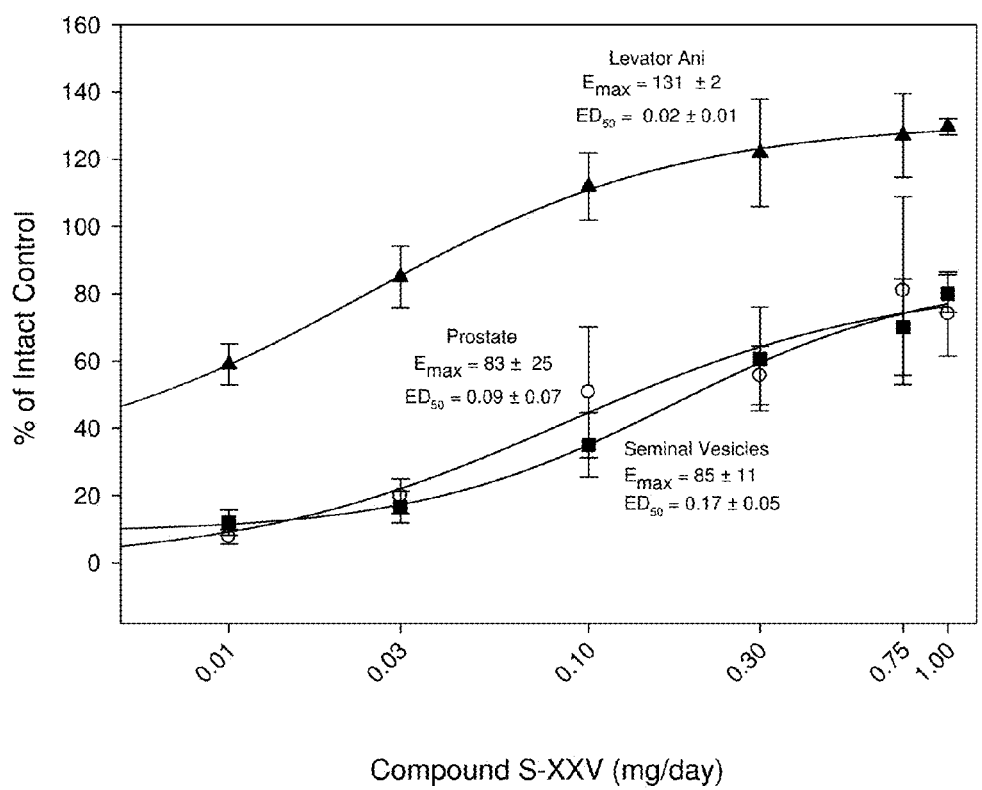
FIG. 13: Anabolic and androgenic activity of a compound of formula S-XXV in ORX rats.

Compound of formula S-XXV partially maintained prostate weight following orchidectomy. Prostate weight in vehicle treated ORX controls decreased to 5%±1% of intact controls. At doses of 0.01, 0.03, 0.1, 0.3, 0.75, and 1.0 mg/day, compound of formula S-XXV maintained prostate weights at 8%±2%, 20%±5%, 51%±19%, 56%±9%, 80%±28%, and 74±12.5% of intact controls, respectively. In castrated controls, seminal vesicle weight decreased to 13%±2% of intact controls. Compound of formula S-XXV partially maintained seminal vesicle weights in ORX animals. Seminal vesicle weights from drug treated animals were 12%±4%, 17%±5%, 35%±10%, 61%±15%, 70%±14%, and 80%±6% of intact controls, following doses of 0.01, 0.03, 0.1, 0.3, 0.75, and 1.0 mg/day, respectively. In ORX controls the levator ani muscle weight decreased to 55%±7% of intact controls. We observed an anabolic effect in the levator ani muscle of compound of formula S-XXV treated animals. Compound of formula S-XXV fully maintained levator ani muscle weights at doses >0.1 mg/day. Doses >0.1 mg/day resulted in significant increases in levator ani weight compared to that observed in intact controls. Levator ani muscle weights as a percentage of intact controls were 59%±6%, 85%±9%, 112%±10%, 122%±16%, 127±12%, and 129.66±2% for the 0.01, 0.03, 0.1, 0.3, 0.75, and 1.0 mg/day dose groups, respectively. $E_{max}$ and $ED_{50}$ values were determined in each tissue by nonlinear regression analysis in WinNonlin® and presented in FIG. 13. $E_{max}$ values were 83%±25%, 85%±11%, and 131%±2% for prostate, seminal vesicles, and levator ani, respectively. The $ED_{50}$ in prostate, seminal vesicles, and levator ani was 0.09±0.07, 0.17±0.05, and 0.02±0.01 mg/day, respectively.

Example 16

Studies of Compound of Formula S-XXIII on Knockout Mice

Dystrophin (DMD) homozygous null nice (−/−) and utrophin (UTRN) heterozygous mice (+/−) were obtained from JAX labs. The animals were used to breed DMD (−/−) UTRN (+/+) and DMD (−/−) UTRN (−/−) mice.

When mice attained 4-6 weeks of age, male mice were castrated and treated as indicated in Table 8.

TABLE 8

Study Design

| Group No. | Mice | Treatment | Duration | N |
|---|---|---|---|---|
| 1 | DMD (−/−) UTRN (−/−) | Vehicle | 12 weeks | 8 |
| 2 | DMD (−/−) UTRN (−/−) | 10 mg/kg/day S-XXV | 12 weeks | 8 |
| 3 | DMD (−/−) UTRN (−/−) | 10 mg/kg/day S-XXIII | 12 weeks | 8 |
| 4 | DMD (−/−) UTRN (−/−) | 10 mg/kg/day S-XXIV | 12 weeks | 8 |
| 5 | Wildtype | Vehicle | 12 weeks | 8 |
| 6 | Wildtype | 10 mg/kg/day S-XXV | 12 weeks | 8 |
| 7 | Wildtype | 10 mg/kg/day S-XXIII | 12 weeks | 8 |
| 8 | Wildtype | 10 mg/kg/day S-XXIV | 12 weeks | 8 |
| 9 | DMD (−/−) UTRN (−/−) | Vehicle | till death (~20 weeks) | 8 |
| 10 | DMD (−/−) UTRN (−/−) | 10 mg/kg/day S-XXV | till death (~20 weeks) | 8 |
| 11 | DMD (−/−) UTRN (−/−) | 10 mg/kg/day S-XXIII | till death (~20 weeks) | 8 |
| 12 | DMD (−/−) UTRN (−/−) | 10 mg/kg/day S-XXIV | till death (~20 weeks) | 8 |
| 13 | DMD (−/−) UTRN (+/+) | Vehicle | 12 weeks | 8 |
| 14 | DMD (−/−) UTRN (+/+) | 10 mg/kg/day S-XXV | 12 weeks | 8 |
| 15 | DMD (−/−) UTRN (+/+) | 10 mg/kg/day S-XXIII | 12 weeks | 8 |
| 16 | DMD (−/−) UTRN (+/+) | 10 mg/kg/day S-XXIV | 12 weeks | 8 |

Figure 15A:
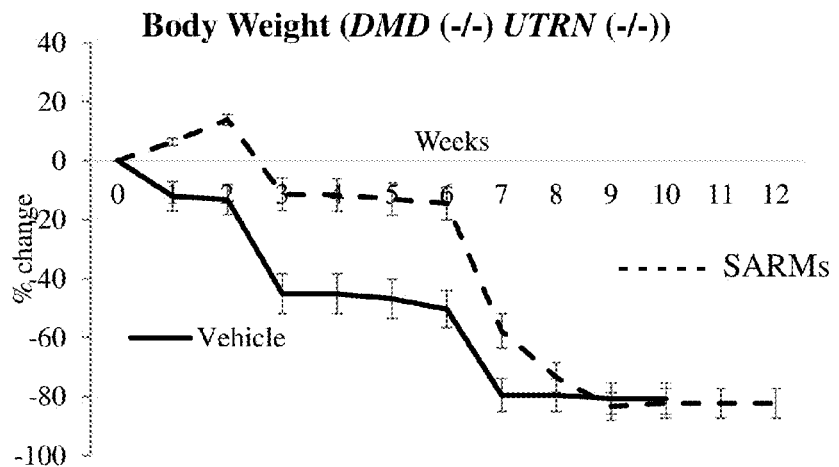
FIGS. 15A-15C show that 'SARMs' (cumulatively S-XXIII, S-XXIV, and S-XXV (combined data for groups 2-4 in Example 16)) delayed the deterioration of body weight, lean mass, and grip strength of DMD (−/−) UTRN (−/−) double knockout mice.
Figure 15B:
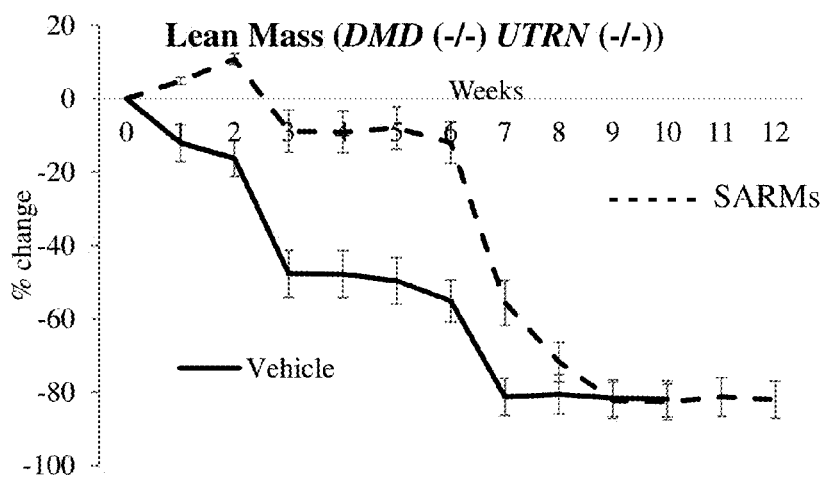
Figure 15C:
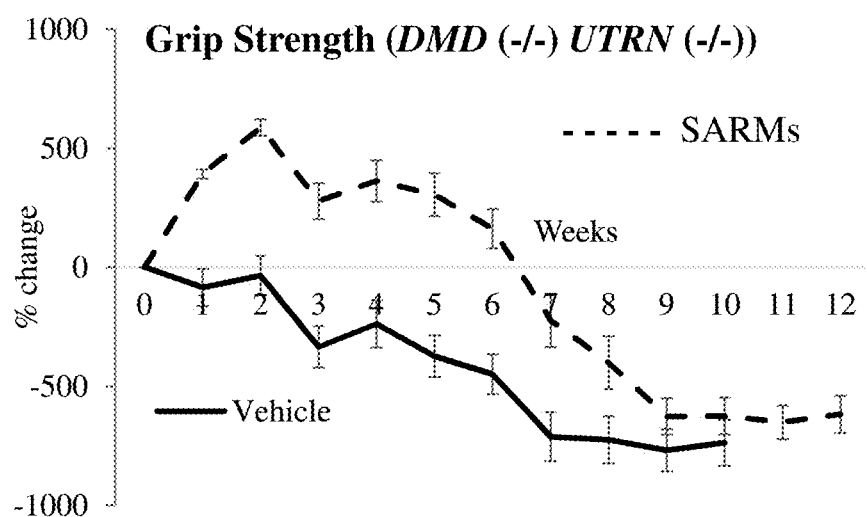

Compounds of formulas S-XXV, S-XXIII, and S-XXIV were used at 10 mpk/day administered subcutaneously. In FIGS. 15A-15C, the labeling as 'SARM' or 'SARMs' indicates cumulative data across groups 2, 3 and 4. One set of UTRN wildtype mice (i.e., the mdx model or DMD (−/−) UTRN (+/+) mice) were also used (i.e., groups 13-16) to evaluate the effect of compound of formula S-XXIII (and other SARMs) on Duchenne muscular dystrophy through UTRN up-regulation.

Weekly body weight, MRI measurements, and grip strengths were measured (body weight: biweekly; MRI scan: once every 2 weeks or once every week; and grip strength: Once every 2 weeks or once every week).

Groups 1-8 and 13-16 were sacrificed after 12 weeks of treatment and various tissues were excised, weighed, and stored appropriately for further analysis. At sacrifice, blood was collected for serum biochemical markers (ALT, AST, glucose, cholesterol, creatinine, creatine kinase, pyruvate, and others). Echocardiogram was performed in one set of knockout mice. As inflammation is considered as one of the primary pathogenic mechanisms, a serum inflammatory markers panel was evaluated. Organs (prostate, seminal vesicles, levator ani, soleus, gastrocnemious, heart, lungs, and liver) were weighed and stored for gene expression studies and histology. Levator ani, soleus, extensor digitorum longus (EDL), and gastrocnemious muscles were processed to measure the tension (if possible), histology and gene expression.

Figure 14A:
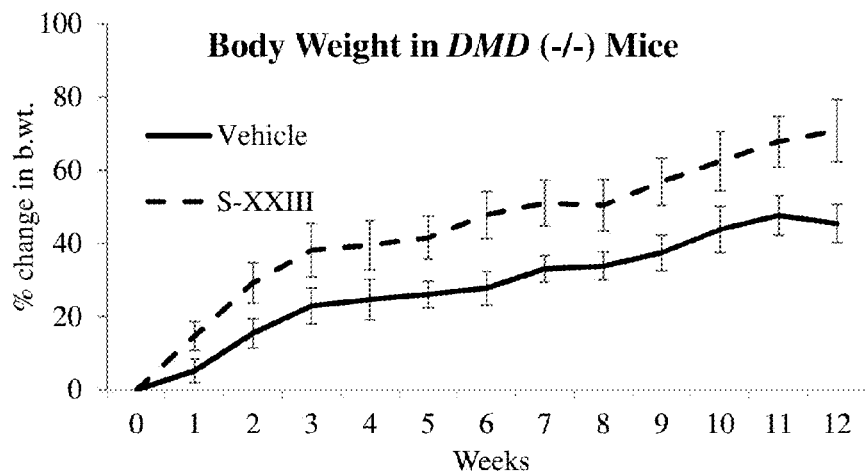
FIGS. 14A-14D show that compound of formula S-XXIII in the DMD single knockout or mdx mouse model (DMD (−/−) UTRN (+/+)), e.g., increased body weight and lean mass.
Figure 14B:
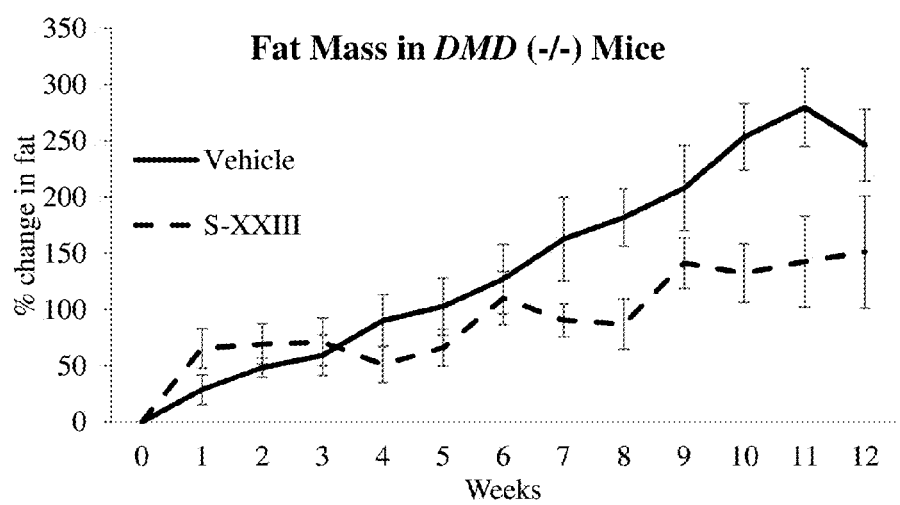
Figure 14C:
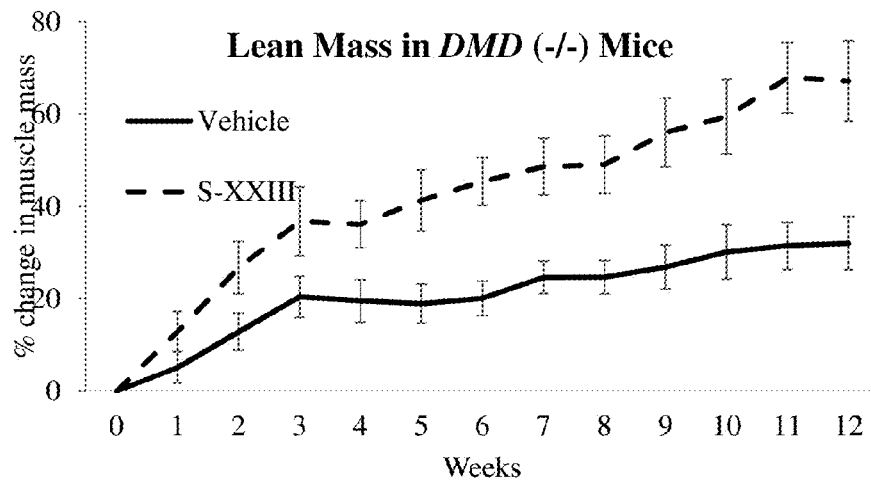
Figure 14D:
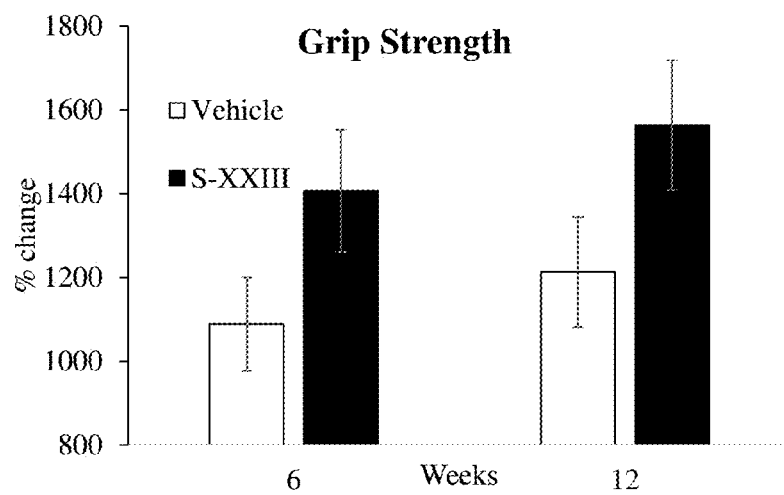

FIGS. 14A-14D show that DMD (−/−) UTRN (+/+) mice when treated with compound of formula S-XXIII demonstrated a significant increase in body weight (FIG. 14A), lean [muscle] mass (FIG. 14C), and grip strength (FIG. 14D), and also a decrease in fat mass (FIG. 14B).

FIGS. 15A-15C show that double knock out mice when treated with vehicle significantly and rapidly lost their body weight, lean [muscle] mass, and grip strength. However, 'SARMs' (compounds of formulas S-XXV, S-XXIII, and S-XXIV; data shown is cumulative across groups 2-4) delayed the deterioration of these measurements significantly. Further, 'SARMs' enhanced the ability of these mice to be ambulatory.

Figure 16A:
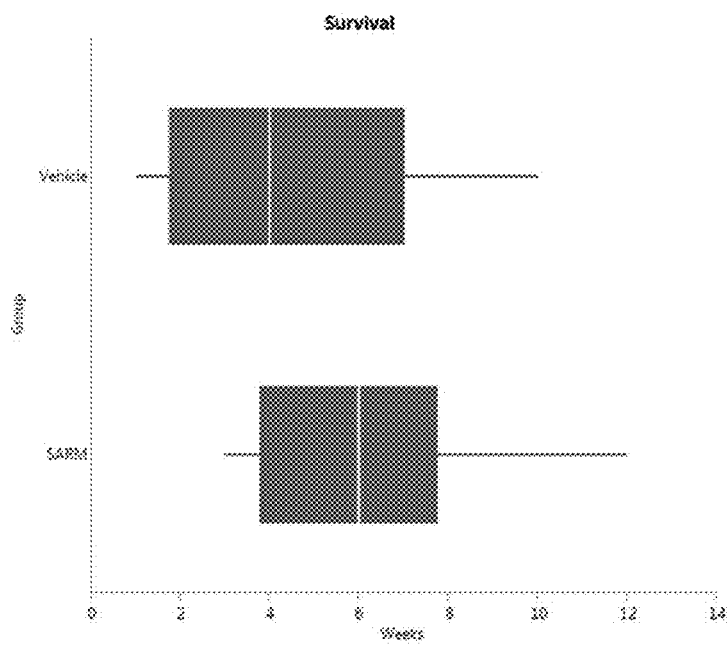
FIGS. 16A and 16B show that compounds of formulas S-XXIII or S-XXV (combined data labeled as 'SARM') and S-XXIII, respectively, increased the survival by 50-70% in DMD (−/−) UTRN (−/−) double knockout mice.
Figure 16B:
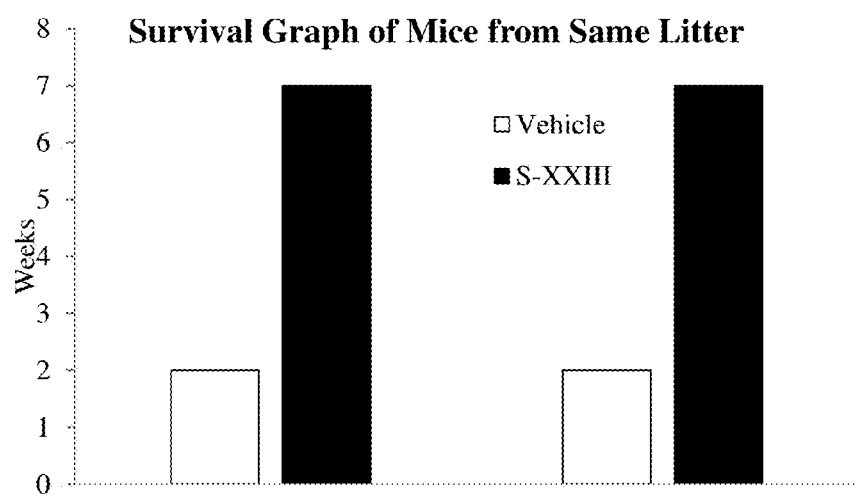

DMD (−/−) UTRN (−/−) male mice were castrated and treated with vehicle or a compound of this invention at 10 mpk s.c. The number of weeks the mice survived was recorded and expressed. The 'SARM' treated group combines the data for S-XXIII and S-XXV treated animals together. Animals from same litter are shown in FIGS. 16A and 16B. FIG. 16A (cumulative data for S-XXIII and S-XXV) and 16B (S-XXIII) show that due to enhancement in body weight and lean [muscle] mass, the [castrated] DMD (−/−) UTRN (−/−) mice treated with the indicated compounds of the invention lived longer by approximately 40-50% compared to [castrated] vehicle-treated control mice from the same litter, suggesting the result is not due to genetic variation but drug efficacy. Cumulatively, this suggests that patients with Duchenne muscular dystrophy treated with S-XXIII (or another SARM of this invention) are expected to not only benefit from improved growth and strength (e.g., improved physical function and quality of life such as longer ambulation) but also may live longer lives. A possible explanation for the survival benefit may be seen in Example 17 below, as the compounds of this invention also improve cardiac function in model of Duchenne muscular dystrophy. FIGS. 19A and 19B and FIGS. 20A and 20B show that intact and castrated mdx mice, i.e., DMD (−/−) UTRN (+/+), were both effected by S-XXIII treatment. The effects of S-XXIII reported above for castrated mdx mice were also seen in intact mdx mice. E.g., S-XXIII increased body weight (FIG. 19A-19B) and lean mass (FIG. 20A-20B) in castrated and intact mdx mice. This suggests that the therapeutic effects for Duchenne muscular dystrophy were not an artifact of the use of castrated animals to model the disease.

Example 17

Echocardiography Test in mdx Mice

Figure 17A:
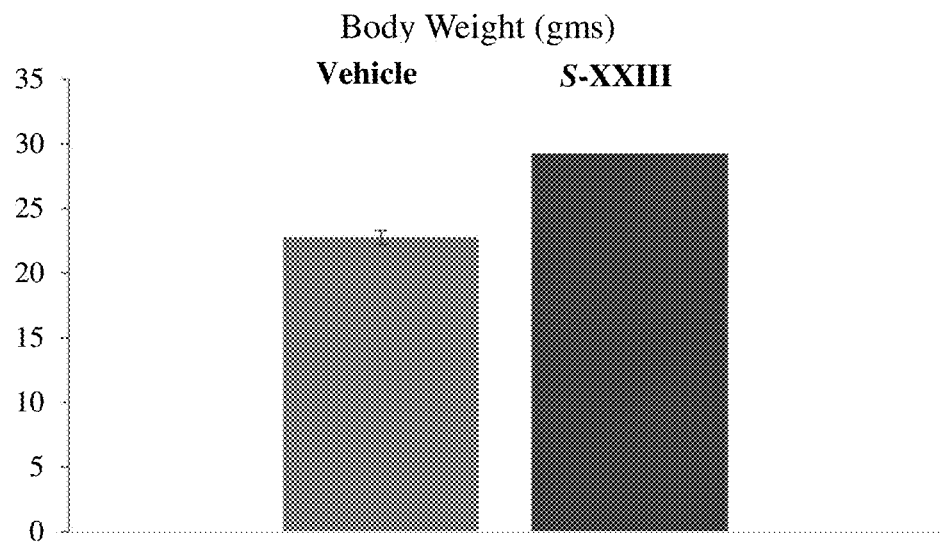
FIGS. 17A-17C show magnetic resonance imaging (MRI) data that compound of formula S-XXIII increased body weight, lean mass, and grip strength in DMD (−/−) UTRN (+/+) mice (separate experiment from mice in Example 16) which were further characterized by echocardiography in FIGS. 18A-18D.
Figure 17B:
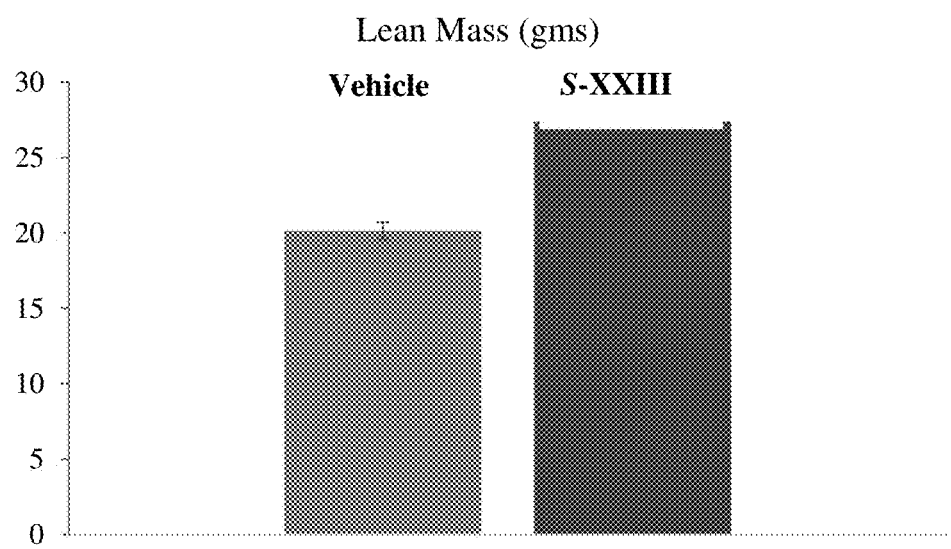
Figure 17C:
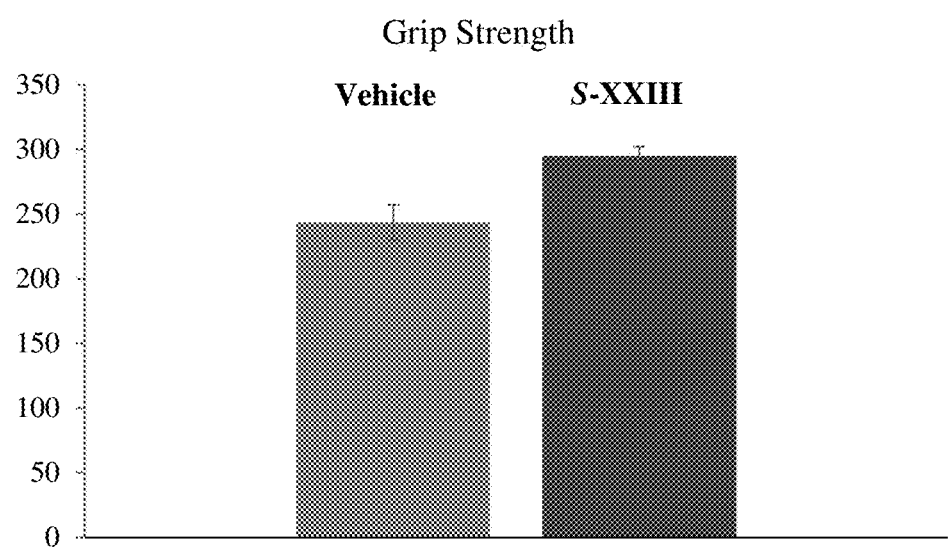

FIGS. 17A-17C: DMD (−/−) UTRN (+/+) (mdx mice; separate experiment from Example 16) male mice were castrated and treated with vehicle or S-XXIII (10 mg/kg/day s.c.) for 10 weeks. Body weight, lean mass, and grip strength were measured at the end of treatment period. Echocardiogram was performed on all mice (n=4/group). Echo results are represented as bar graphs in FIGS. 18A-18D.

Consistent with Example 16 and the scientific literature, mdx mice experienced decreases in growth and strength. However, mice treated with compound of formula S-XXIII had increased body weight, lean [muscle] mass, and grip strength, demonstrating the global therapeutic effects of compounds of this invention. Further, the mdx mice suffered from aortic stenosis and aortic valvular dysfunction. However, this disorder was shown to be completely reversed by treatment with compound of formula S-XXIII (FIGS. 18A-18D).

Figure 18A:
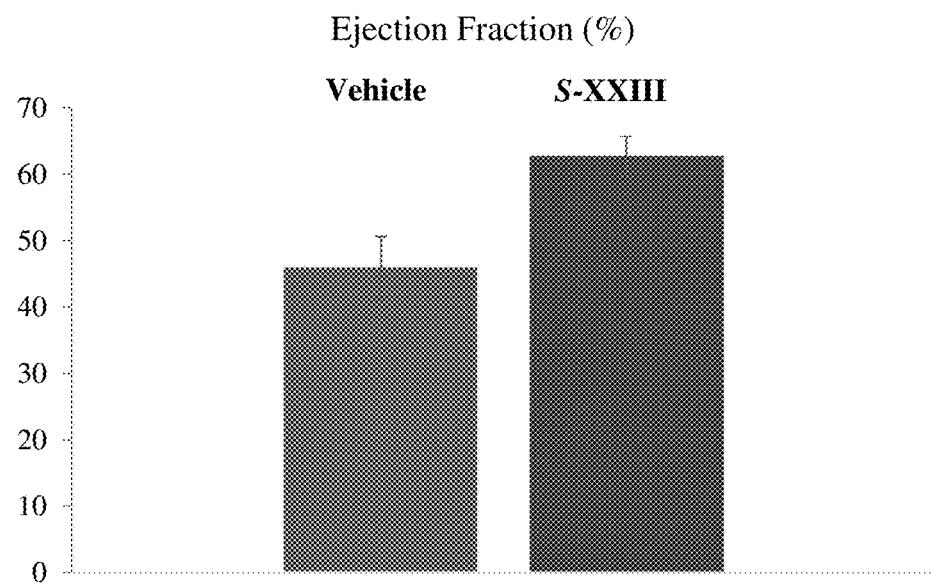
Figure 18B:
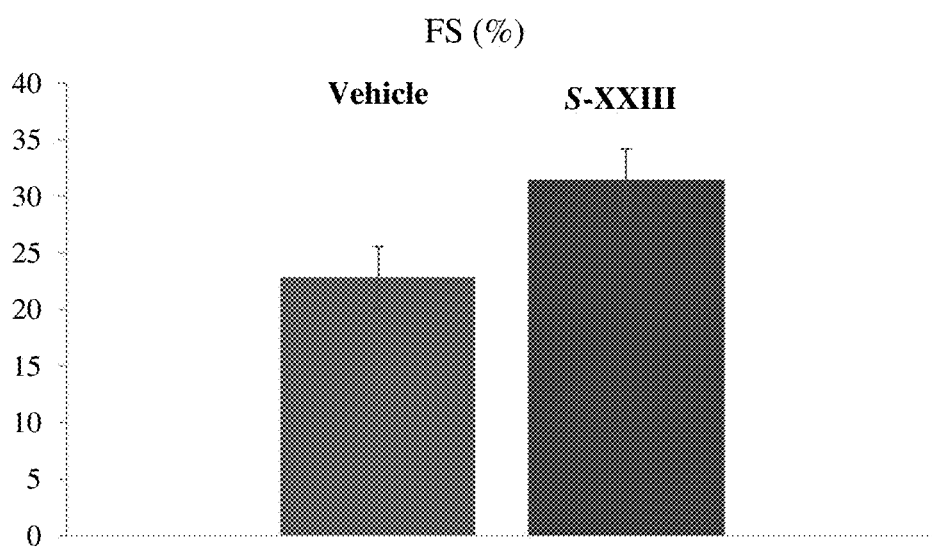
FIG. 18B shows the effects of S-XXIII on fractional shortening (FS) (%).
Figure 18C:
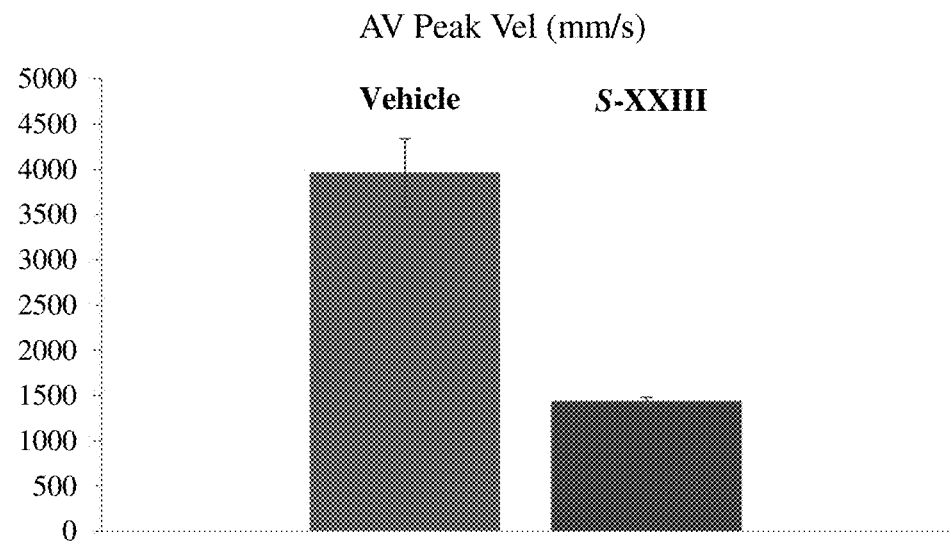
FIG. 18C shows the effects of S-XXIII on AV peak velocity (aortic valve peak velocity) (mm/s).
Figure 18D:
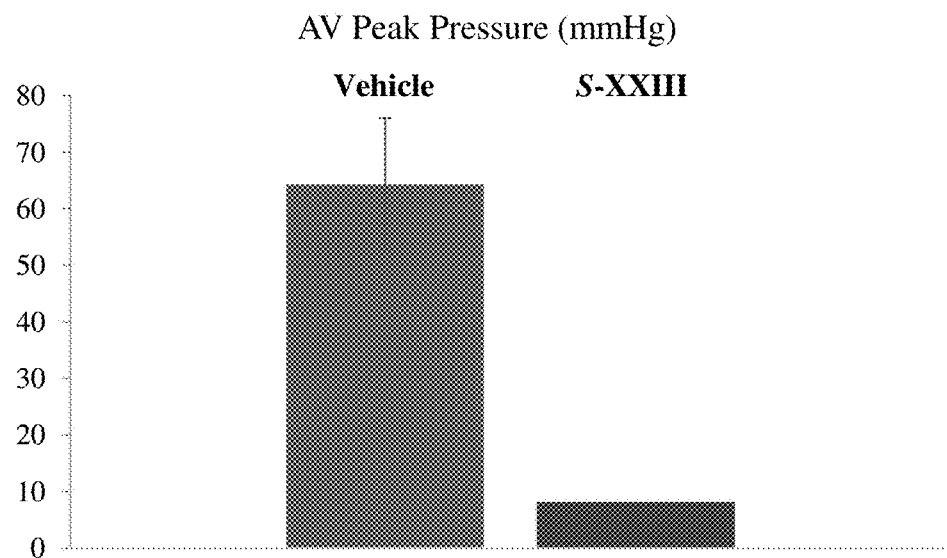
FIG. 18D shows the effects of S-XXIII on AV peak pressure (mmHg).
Figure 19A:
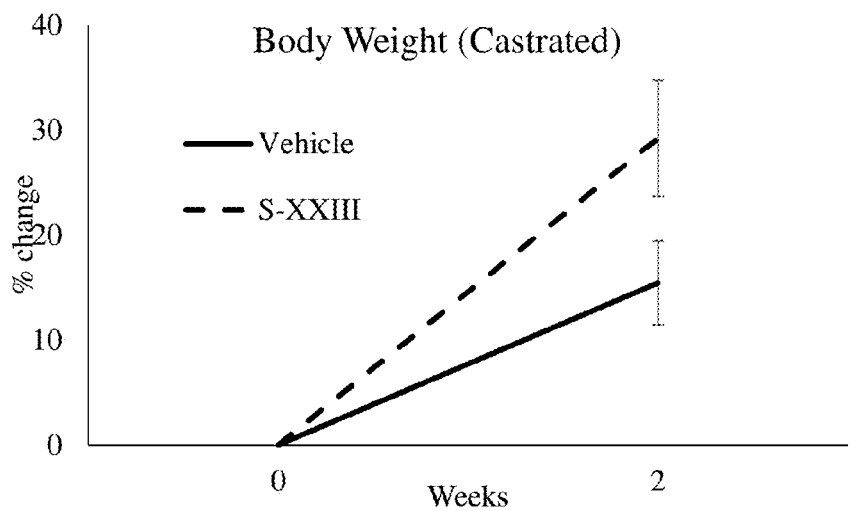
FIGS. 19A and 19B depict the effect of S-XXIII on body weight of intact DMD (−/−) UTRN (+/+) mice in comparison with castrated mice.
Figure 19B:
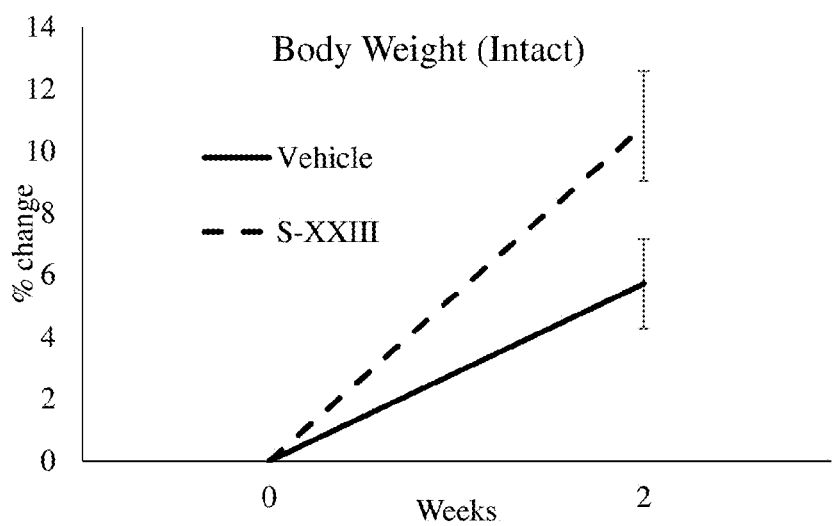
Figure 20A:
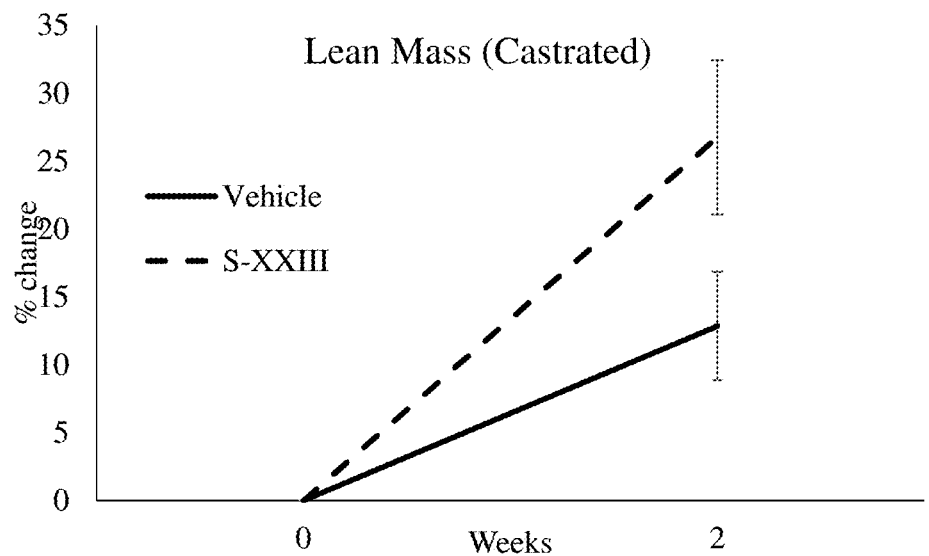
FIGS. 20A and 20B depict the effect of S-XXIII on lean mass of intact DMD (−/−) UTRN (+/+) mice in comparison with castrated mice.
Figure 20B:
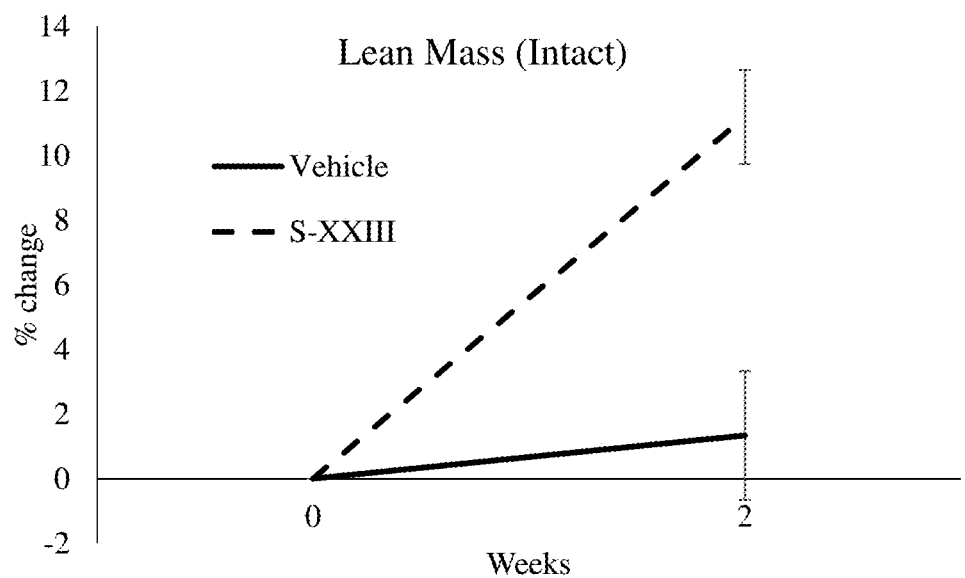

FIG. 18A also shows that the cardiac function was highly compromised in mdx mice (ejection fraction (EF; %)). However, the compromised cardiac function was reversed by compound of formula S-XXIII. Ejection fraction less than 55% is considered as cardiac failure. The mdx mice have EF of 45%, while the treated mice have EF of 63%. The data show that compound of formula S-XXIII strengthens cardiac muscle. FIG. 18B shows the effects of S-XXIII on fractional shortening (FS) (%). Fractional shortening is used as an estimate of myocardial contractility. However, this is only a guide and is very dependant on the loading factors which affect the contraction of the heart. If the ventricle does not fill normally during diastole the FS % will be reduced. FS % is particularly sensitive to changes in afterload. An increase in systemic blood pressure or an increase in myocardial stiffness will therefore reduce FS %. FS % can also be influenced by the heart rate. Excitement may result in an increased FS % as a result of catecholamine release. Valvular heart disease will affect ventricular function before any change in myocardial contractility occurs. For example, mitral regurgitation will result in a decreased afterload because it acts as a let-off valve during systole. In addition, if the valvular disease is severe enough to have resulted in volume overload, preload may be increased. These factors increase FS % by decreasing systolic dimensions and increasing diastolic dimensions respectively. Once myocardial failure develops, FS % will fall. FIG. 18B demonstrates that mdx mice have decreased FS % consistent with heart failure which is reversed by S-XXIII administration. FIG. 18C shows the effects of S-XXIII on AV peak velocity (aortic valve peak velocity) (mm/s). FIG. 18D shows the effects of S-XXIII on AV peak pressure (mmHg). The dramatically increased AV peak velocity and AV peak pressure indicates stenosis (narrowing or constriction) of the aortic valve which was reversed by S-XXIII administration.

It will be appreciated by a person skilled in the art that the present invention is not limited by what has been particularly shown and described hereinabove. Rather, the scope of the invention is defined by the claims that follow:

What is claimed is:
1. A method of treating, reducing the severity, reducing the incidence, delaying the onset, or reducing the pathogenesis of Duchenne muscular dystrophy in a subject in need thereof, comprising administering to said subject a selective androgen receptor modulator (SARM) compound represented by the structure of formula S-XXIII:

S-XXIII

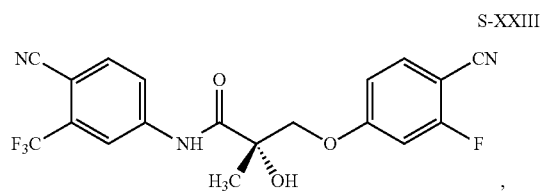 [SMILES: C[C@](O)(COc1ccc(C#N)c(F)c1)C(=O)Nc1ccc(C#N)c(C(F)(F)F)c1]

or its optical isomer, pharmaceutically acceptable salt or any combination thereof.

2. The method of claim 1, wherein said administering comprises administering a pharmaceutical composition comprising said compound and/or its optical isomer, pharmaceutically acceptable salt or any combination thereof; and a pharmaceutically acceptable carrier.

3. The method of claim 1, wherein said method further increases the physical function of said subject.

4. The method of claim 1, wherein said method further increases the quality of life of said subject.

5. The method of claim 1, wherein said method increases the survival of said subject.

6. The method of claim 1, wherein said method further delays onset or improves symptoms of cardiomyopathy.

7. A method of increasing the physical function of a subject suffering from Duchenne muscular dystrophy, comprising administering to said subject a selective androgen receptor modulator (SARM) compound represented by the structure of formula S-XXIII:

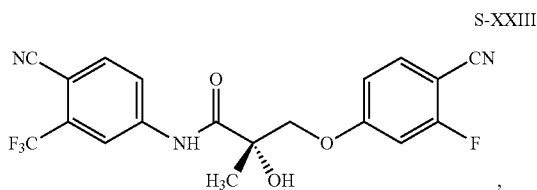 [SMILES: C[C@](O)(COc1ccc(C#N)c(F)c1)C(=O)Nc1ccc(C#N)c(C(F)(F)F)c1]

or its optical isomer, pharmaceutically acceptable salt or any combination thereof.

8. A method of increasing the quality of life of a subject suffering from Duchenne muscular dystrophy, comprising administering to said subject a selective androgen receptor modulator (SARM) compound represented by the structure of formula S-XXIII:

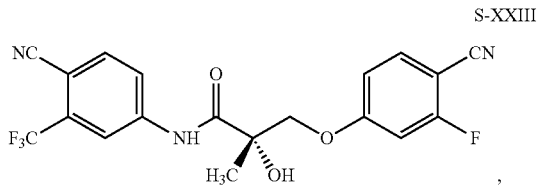 [SMILES: C[C@](O)(COc1ccc(C#N)c(F)c1)C(=O)Nc1ccc(C#N)c(C(F)(F)F)c1]

or its optical isomer, pharmaceutically acceptable salt or any combination thereof.

9. A method of increasing the survival of a subject suffering from Duchenne muscular dystrophy, comprising administering to said subject a selective androgen receptor modulator (SARM) compound represented by the structure of formula S-XXIII:

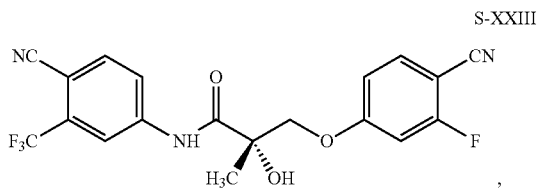 [SMILES: C[C@](O)(COc1ccc(C#N)c(F)c1)C(=O)Nc1ccc(C#N)c(C(F)(F)F)c1]

or its optical isomer, pharmaceutically acceptable salt or any combination thereof.

10. A method of treating, reducing the severity, reducing the incidence, delaying the onset, or reducing the pathogenesis of cardiomyopathy in a subject suffering from Duchenne muscular dystrophy, comprising administering to said subject a selective androgen receptor modulator (SARM) compound represented by the structure of formula S-XXIII:

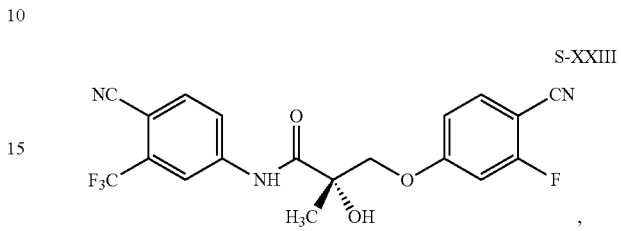

or its optical isomer, pharmaceutically acceptable salt or any combination thereof.

11. A method of treating, reducing the severity, reducing the incidence, delaying the onset, or reducing the pathogenesis of Becker muscular dystrophy in a subject in need thereof, comprising administering to said subject a selective androgen receptor modulator (SARM) compound represented by the structure of formula S-XXIII:

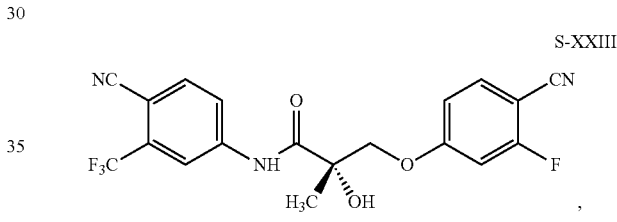

or its optical isomer, pharmaceutically acceptable salt or any combination thereof.

12. The method of claim 11, wherein said administering comprises administering a pharmaceutical composition comprising said compound and/or its optical isomer, pharmaceutically acceptable salt or any combination thereof; and a pharmaceutically acceptable carrier.

13. The method of claim 11, wherein said method further increases the physical function of said subject.

14. The method of claim 11, wherein said method further increases the quality of life of said subject.

15. The method of claim 11, wherein said method further delays onset or improves symptoms of cardiomyopathy.

* * * * *

UNITED STATES PATENT AND TRADEMARK OFFICE
CERTIFICATE OF CORRECTION

PATENT NO. : 9,730,908 B2  
APPLICATION NO. : 14/963054  
DATED : August 15, 2017  
INVENTOR(S) : James T. Dalton et al.

Page 1 of 1

It is certified that error appears in the above-identified patent and that said Letters Patent is hereby corrected as shown below:

Inventors should read:   James T. Dalton, Ann Arbor, MI (US)  
Thamarai Ponnuaamy, Memphis, TN (US)  
Ramesh Narayanan, Cordove, TN (US)

Signed and Sealed this  
Seventh Day of November, 2017

Joseph Matal  
*Performing the Functions and Duties of the*  
*Under Secretary of Commerce for Intellectual Property and*  
*Director of the United States Patent and Trademark Office*